US012637659B2

(12) United States Patent
Hayday et al.

(10) Patent No.: US 12,637,659 B2
(45) Date of Patent: ***May 26, 2026

(54) EXPANSION OF NON-HAEMATOPOIETIC TISSUE-RESIDENT GAMMA DELTA T CELLS AND USES OF THESE CELLS

(71) Applicants:CANCER RESEARCH TECHNOLOGY LIMITED, London (GB); KING'S COLLEGE LONDON, London (GB); THE FRANCIS CRICK INSTITUTE LIMITED, London (GB)

(72) Inventors: Adrian Hayday, Kent (GB); Oliver Nussbaumer, London (GB); Richard Woolf, London (GB)

(73) Assignees: CANCER RESEARCH TECHNOLOGY LIMITED, London (GB); KING'S COLLEGE LONDON, London (GB); THE FRANCIS CRICK INSTITUTE LIMITED, London (GB)

( * ) Notice: Subject to any disclaimer, the term of this patent is extended or adjusted under 35 U.S.C. 154(b) by 442 days.

This patent is subject to a terminal disclaimer.

(21) Appl. No.: 17/936,811

(22) Filed: Sep. 29, 2022

(65) Prior Publication Data

US 2023/0099491 A1     Mar. 30, 2023

Related U.S. Application Data

(63) Continuation of application No. 15/771,875, filed as application No. PCT/EP2016/076264 on Oct. 31, 2016, now Pat. No. 11,618,885.

(30) Foreign Application Priority Data

Oct. 30, 2015    (GB) ...................................... 1519198
Jul. 22, 2016    (GB) ...................................... 1612731

(51) Int. Cl.
*C12N 5/0783*     (2010.01)
*A61K 35/17*      (2025.01)
*A61K 40/11*      (2025.01)
*A61K 40/42*      (2025.01)

(52) U.S. Cl.
CPC ............ *C12N 5/0638* (2013.01); *A61K 40/11* (2025.01); *A61K 40/42* (2025.01); *C12N 2501/2302* (2013.01); *C12N 2501/2315* (2013.01)

(58) Field of Classification Search
None
See application file for complete search history.

(56) References Cited

U.S. PATENT DOCUMENTS 7,078,034 B2    7/2006    Lamb et al.
8,012,466 B2    9/2011    Morita et al.

9,499,788 B2    11/2016    De Carvalho E Silva Santos et al.
11,618,885 B2    4/2023    Hayday et al.
2006/0246520 A1    11/2006    Champagne et al.
2014/0046026 A1    2/2014    Garcia et al.
2017/0107490 A1    4/2017    Maeurer

FOREIGN PATENT DOCUMENTS

CN    103635573 A    3/2014
CN    104293734 A    1/2015
CN    104711224 A    6/2015
WO    WO-0026347 A1    5/2000
WO    WO-2007046006 A2    4/2007
WO    WO-2012156958 A2    11/2012
WO    WO-2015061694 A2    4/2015
WO    WO-2016198480 A1    12/2016
WO    WO-2017072367 A1    5/2017

OTHER PUBLICATIONS

Almeida, A.R., et al., "Delta One T Cells for Immunotherapy of Chronic Lymphocytic Leukemia: Clinical-Grade Expansion/ Differentiation and Preclinical Proof-of-Concept," Clin. Cancer Res. 22(23):5795-804, American Association for Cancer Research, United States (Dec. 2016).

Bendersky, A., et al., "Cellular Interactions of Synovial Fluid (gamma)(delta) T Cells in Juvenile Idiopathic Arthritis," J. Immunol. 188(9):4349-59, American Association of Immunologists, United States (May 2012).

Bennouna, J., et al., "Phase-I study of Innacell gammadelta, an autologous cell-therapy product highly enriched in gamma9delta2 T lymphocytes, in combination with IL-2, in patients with metastatic renal cell carcinoma," Cancer Immunol. Immunother. 57(11):1599-609, Springer, Germany (Nov. 2008).

Choudhary, A., et al., "Selective lysis of autologous tumor cells by recurrent gamma delta tumor-infiltrating lymphocytes from renal carcinoma," J. Immunol. 154(8):3932-40, American Association of Immunologists, United States (Apr. 1995).

Clark, R.A., et al., "A Novel Method for the Isolation of Skin Resident T Cells from Normal and Diseased Human Skin," J. Invest. Dermatol. 126(5):1059-70, Elsevier, Netherlands (May 2006).

Das, H., et al., "Mechanisms of Vδ1 γδ T cell activation by microbial components," J. Immunol. 172(11):6578-86, American Association of Immunologists, United States (Jun. 2004).

Deniger, D.C., at al., "Clinical Applications of Gamma Delta T Cells with Multivalent Immunity," Front. Immunol. 5:636, Frontiers Media S.A., United States (Dec. 2014).

(Continued)

*Primary Examiner* — Michail A Belyavskyi
(74) *Attorney, Agent, or Firm* — Sterne, Kessler, Goldstein & Fox P.L.L.C.

(57) ABSTRACT

This invention relates to the expansion of non-haematopoietic tissue-resident γδ T cells in vitro by culturing lymphocytes obtained from non-haematopoietic tissue of humans or non-human animals in the presence of interleukin-2 (IL-2) and/or interleukin-15 (IL-15) and the absence of TCR activation or co-stimulation signals, without any direct contact with stromal or epithelial cells. Methods of non-haematopoietic tissue-resident γδ T cell expansion are provided, as well as populations of non-haematopoietic tissue-resident γδ T cells and uses thereof.

14 Claims, 40 Drawing Sheets

(56)                    References Cited

OTHER PUBLICATIONS

Deniger, D.C., et al., "Activating and Propagating Polyclonal Gamma Delta T Cells with Broad Specificity for Malignancies," Clin. Cancer Res. 20(22):5708-5719, American Association for Cancer Research, United States (Nov. 2014).

Forrester, J.M., et al., "Clonal Expansion of Lung V delta 1 + T Cells in Pulmonary Sarcoidosis," J Clin. Invest. 91(1):292-300, American Society for Clinical Investigation, United States (Jan. 1993).

Gustafsson, K., et al., "Regeneration of stalled immune responses to transformed and infected cells using δγ T cells," Drug Discov. Today 19(6): 787-793, Taylor & Francis, United Kingdom (Jun. 2014).

International Search Report and Written Opinion for International Patent Application No. PCT/EP2016/076264, mailed Mar. 24, 2017, European Patent Office, Netherlands, 14 pages.

Kim, K., et al., "Comparative Analysis of Human Epidermal and Peripheral Blood Gamma Delta T Cell Cytokine Profiles," Ann. Dermatol. 26(3):308-13, Korean Dermatological Association, Korea (Jun. 2014).

Li, J., et al., "Distinct Pattern of Human Vdelta1 GammaDelta T Cells Recognizing MICA," Cell Mol. Immunol. 2(4):253-8, The Chinese Society of Immunology, China (Aug. 2005).

Nakajima, J., et al., "A Phase I Study of Adoptive Immunotherapy for Recurrent Non-Small Cell Lung Cancer Patients with Autologous GammaDelta T Cells, " Eur. J. Cardiothorac. Surg. 37(5):1191-1197, Elsevier, Netherlands (May 2010).

Nanno, M., et al., "Gamma/delta T cell antigen receptors expressed on tumor-infiltrating lymphocytes from patients with solid tumors," Eur. J. Immunol. 22(3):679-87, Wiley, United States (Mar. 1992).

Qi, J., et al., "Immobilized MICA could expand human Vdelta1 gammadelta T cells in vitro that displayed major histocompatibility complex class I chain-related A-dependent cytotoxicity to human epithelial carcinomas," Scand. J. Immunol. 58(2):211-20, Wiley, United States (Aug. 2003).

Ribot, J.C., et al., "Human δγ thymocytes are functionally immature and differentiate into cytotoxic type 1 effector T cells upon IL-2/IL-15 signaling," J. Immunol. 192(5):2237-43, American Association of Immunologists, United States (Mar. 2014).

Sakamoto, M., et al., "Adoptive Immunotherapy for Advanced Non-Small Cell Lung Cancer Using Zoledronate-Expanded GammaDelta T Cells: A Phase I Clinical Study," J. Immunother. 34(2):202-11, American Association of Immunologists, United States (Mar. 2011).

Silva-Santos, B., et al., "δγ T cells in cancer," Nat. Rev. Immunol. 15(11):683-91, Nature Publishing Group, United Kingdom (Nov. 2015).

Vantourout, P., et al., "Six-of-the-Best: Unique Contributions of GammaDelta T Cells to Immunology," Nat. Rev Immunol. 13(2):88-100, Nature Publishing Group, United Kingdom (Feb. 2013).

Woolf, R., et al., "Cutaneous V(delta)1 + cells provide evidence for human innate-like T- cells," Immunol. 143(Suppl. 2):51, Wiley, United States (Dec. 2014) (Abstract Only).

Woolf, R., et al., "464 Healthy Human skin harbours a resident T cell subset with rapid, innate-like responsiveness: a new perspective on tissue immune-surveillance," J. Invest. Dermatol. 136(5 Suppl1):S82, Elsevier, Netherlands (May 2016) (Abstract Only).

Woolf, R., et al., "V(delta)1 + T cells in human skin provide evidence for innate-like T cells with implications for tissue lymphoid stress surveillance," Brit. J. Dermatol. 172(Suppl 5):e48, Wiley, United States (May 2015) (Abstract Only).

Wu, Y.L., et al., "GammaDelta T Cells and Their Potential for Immunotherapy," Int. J. Biol. Sci. 10(2):119-35, Ivyspring International Publisher, Australia (Jan. 2014).

Garcia, V.E., et al., "IL-15 enhances the response of human gamma delta T cells to nonpeptide [correction of nonpetide] microbial antigens," J. Immunol. 160(9):4322-4329, American Association of Immunologists, United States (May 1998).

Menzerov, A.G., et al., [The Necessity of Cell Banks], Vavilovsky Journal of Genetics and Breeding 20(6):945-948, Vavilov Society for Geneticists and Breeding Scientists, Russia (2016).

Van Acker, H.H., et al., "Interleukin-15 enhances the proliferation, stimulatory phenotype, and antitumor effector functions of human gamma delta T cells," J. Hematol. Oncol. 9(1):101, BioMed Central Ltd., United Kingdom (Sep. 2016).

International Search Report for International Patent Application No. PCT/EP2016/076264, mailed Mar. 13, 2020, European Patent Office, Netherlands, 2 pages.

Inagaki-Ohara, K., et al., "Interleukin-15 preferentially promotes the growth of intestinal intraepithelial lymphocytes bearing gamma delta T cell receptor in mice," Eur. J. Immunol. 27:2885-2891, Wiley, United States (Nov. 1997).

Vechkanov, E.M., et al., "Fundamentals of Cell Engineering: A Study Guide," pp. 15-16, Rostov-na-Donu, Russia (2012).

Novokhatsky, A.S., et al., "[Problem of cell contamination and new approaches to control of transplanted lines]," Problems of Virology 4:396-408, Russian Academy of Sciences, Russia (1977).

Zhdanov, V.M., et al., "The Mystery of the Third Kingdom," pp. 124-125, M., "Znanie" (1975).

Yangulov, S.U., et al., "[The Effect of Different Cryoprotective Media on the Viability of Freeze-Thawed Lymphoblastoid Cell Lines H-9 and U-9," Problems of Cryobiology 3:46-39, Order of the Red Banner of Labour Antiplaque Research Institute of Rosov-on-Don, Russia (1991).

Search Report Russian Patent Application No. 2018119684, mailed Mar. 3, 2020, Federal Service for Intellectual Property, Russia, 5 pages.

Seo, W., et al., "Toll-like Receptor 3 Accelerates Liver Fibrosis by Enhancing IL-17 Production in Mice," Hepatology 60:575A, Abstract 776, American Association for the Study of Liver Diseases, United States (Oct. 2014).

Office Action for Japanese Patent Application 2018-541524, mailed May 11, 2021, Japan Patent Office, Japan, 5 pages.

Dong, J., et al., "[In vitro expansion of T cells stimulated by combination of IL-2, IL-7 and IL-15]," J. Exp. Hematology 18(6):1590-1594, Haidian-qu, China (Dec. 2010).

Payne, K.K., et al., "Peripheral blood mononuclear cells of patients with breast cancer can be reprogrammed to enhance anti-HER-2/neu reactivity and overcome myeloid-derived suppressor cells," Breast Cancer Res. Treat. 142(1):45-57, SpringerLink, United Kingdom (Nov. 2013).

Office Action for Malaysian Patent Application PI2018000604, mailed on May 22, 2021, Intellectual Property Corporation of Malaysia, Malaysia, 3 pages.

Agostini, C., et al., "Role of IL-15, IL-2, and their receptors in the development of T cell alveolitis in pulmonary sarcoidosis," J. Immunol. 157(2):910-918, American Association of Immunologists, United States (Jul. 1996).

Office Action for Israel Patent Application 258985, mailed on Apr. 25, 2021, Israel Patent Office, Israel, 7 pages.

Zhang, W., "[Introduction of δγT cell,]" Foreign Medical Sciences Section of Immunology 24(1):47-50, China (2001).

Petrini, I., et al., "Mesenchymal cells inhibit expansion but not cytotoxicity exerted by gamma-delta T cells," Eur J Clin Invest 39(9):813-818, Wiley-Blackwell Publishing Ltd., United Kingdom (Sep. 2009).

Siegers, G., et al., "Extensive expansion of primary human gamma delta T cells generates cytotoxic effector memory cells that can be labeled with Feraheme for cellular MRI," Cancer Immunol Immunother 62(3):571-583, Springer Science and Business Media, Germany (Mar. 2013).

Brahmer, J. R., et al., "Safety and Activity of Anti-PD-L1 Antibody in Patients with Advanced Cancer," The New England Journal of Medicine 366(26):2455-2465, Massachusetts Medical Society, United States (Jun. 2012).

Carrasco, A., et al., "Comparison of Lymphocyte Isolation Methods for Endoscopic Biopsy Specimens From the Colonic Mucosa," Journal of Immunological Methods 389(1-2):29-37, Elsevier, Netherlands (Mar. 2013).

Couzi, L., et al., "Cytomegalovirus-induced Gammadelta T Cells Associate With Reduced Cancer Risk After Kidney Transplantation," Journal of the American Society of Nephrology 21(1):181-188, Wolters Kluwer Health, United States (Jan. 2010).

(56) References Cited

OTHER PUBLICATIONS

Curran, K.J., and Brentjens, R.J., "Chimeric Antigen Receptor T Cells for Cancer Immunotherapy," Journal of Clinical Oncology 33(15):1703-1706, American Society of Clinical Oncology, United States (May 2015).

Deniger, D.C., et al., "Bispecific T-cells Expressing Polyclonal Repertoire of Endogenous Gd T-cell Receptors and Introduced CD19-specific Chimeric Antigen Receptor," Molecular Therapy : The Journal of the American Society of Gene Therapy 21(3):638-647, Academic Press, United States (Mar. 2013).

Echchakir, H., et al., "A Point Mutation in the Alpha-Actinin-4 Gene Generates an Antigenic Peptide Recognized by Autologous Cytolytic T Lymphocytes on a Human Lung Carcinoma," Cancer Research 61(10):4078-4083, American Association for Cancer Research, United States (May 2001).

Fecher, L.A., et al., "Ipilimumab and Its Toxicities: A Multidisciplinary Approach," The Oncologist 18(6):733-743, Oxford University Press, United Kingdom (Jun. 2013).

Fournie, J.J., et al., "What Lessons Can Be Learned From Gd T Cell-based Cancer Immunotherapy Trials?," Cellular & Molecular Immunology 10(1):35-41, Chinese Society of Immunology, China (Jan. 2013).

Freed-Pastor, W.A., et al., "Mutant p53 Disrupts Mammary Tissue Architecture via the Mevalonate Pathway," Cell 148(1):244-258, (Jan. 2012).

Fujita, T., et al., "Structure of the Human Interleukin 2 Gene, " Proceedings of the National Academy of Sciences of the United States of America 80(24):7437-7441, National Academy of Sciences, United States (Dec. 1983).

Gaudin, C., et al., "A HSP70-2 Mutation Recognized by CTL on a Human Renal Cell Carcinoma," Journal of Immunology (Baltimore, Md. : 1950) 162(3):1730-1738, Oxford University Press, United Kingdom (Feb. 1999).

Gertner-Dardenne, J., et al., "Human V?9Vd2 T Cells Specifically Recognize and Kill Acute Myeloid Leukemic Blasts," Journal of Immunology 188(9):4701-4708, Oxford University Press, United Kingdom (May 2012).

Gillis, S., and Smith, K,A., "Long Term Culture of Tumour-specific Cytotoxic T Cells," Nature Nature Publishing Group 268(5616):154-156 United kingdom (Jul. 1977).

Godder, K.T., et al., "Long Term Disease-free Survival in Acute Leukemia Patients Recovering With Increased Gammadelta T Cells After Partially Mismatched Related Donor Bone Marrow Transplantation," Bone Marrow Transplantation 39(12):751-757, Nature Publishing Group, United Kingdom (Jun. 2007).

Grabstein, K.H., et al., "Cloning of a T Cell Growth Factor That Interacts With the Beta Chain of the Interleukin-2 Receptor," Science 264(5161):965-968, American Association for the Advancement of Science, United States (May 1994).

Gruenbacherm F., et al., "CD56+ Human Blood Dendritic Cells Effectively Promote TH1-type Gammadelta T-cell Responses," Blood 114(20):4422-4431, Elsevier, United States (Nov. 2009).

Hillerdal, V., and Essand, M., "Chimeric Antigen Receptor-engineered T Cells for the Treatment of Metastatic Prostate Cancer," BioDrugs 29(2):75-89, Springer International, New Zealand (Apr. 2015).

Hintz, M., et al., "Identification of (E)-4-hydroxy-3-methyl-but-2-enyl Pyrophosphate as a Major Activator for Human Gammadelta T Cells in *Escherichia coli*," FEBS Letters 509(2):317-322, John Wiley & Sons Ltd, United Kingdom (Dec. 2001).

Ho, W.Y., et al., "In Vitro Methods for Generating CD8+ T-cell Clones for Immunotherapy From the Naïve Repertoire," Journal of Immunological Methods 310(1-2):40-52, Elsevier, Netherlands (Mar. 2006).

Hodi, F.S., et al., "Improved Survival with Ipilimumab in Patients with Metastatic Melanoma," The New England Journal of Medicine 363(8):711-723, Massachusetts Medical Society, United States (Aug. 2010).

Karanikas, V., et al., "High Frequency of Cytolytic T Lymphocytes Directed Against a Tumor-specific Mutated Antigen Detectable With HLA Tetramers in the Blood of a Lung Carcinoma Patient With Long Survival," Cancer Research 61(9):3718-3724, American Association for Cancer Research, United States (May 2001).

Pardoll, D.M., "The Blockade of Immune Checkpoints in Cancer Immunotherapy," Nature Reviews. Cancer 12(4):252-264, Nature Publishing Group, United Kingdom (Mar. 2012).

Pieper, R., et al., "Biochemical Identification of a Mutated Human Melanoma Antigen Recognized by CD4(+) T Cells," The Journal of Experimental Medicine 189(5):757-765, Rockefeller University Press, United States (Mar. 1999).

Ribas, A., "Tumor Immunotherapy Directed at PD-1," The New England Journal of Medicine 366(26):2517-2519, Massachusetts Medical Society, United States (Jun. 2012).

Robert, C., et al., "Ipilimumab Plus Dacarbazine for Previously Untreated Metastatic Melanoma," The New England Journal of Medicine 364:2517-2526, Massachusetts Medical Society, Boston (Jun. 2011).

Sensi, M., et al., "Immunogenicity Without Immunoselection: A Mutant but Functional Antioxidant Enzyme Retained in a Human Metastatic Melanoma and Targeted by CD8(+) T Cells With a Memory Phenotype," Cancer Research 65(2):632-640, American Association for Cancer Research, United States (Jan. 2005).

Todaro, M., et al., "Efficient Killing of Human Colon Cancer Stem Cells by Gammadelta T Lymphocytes," Journal of Immunology 182(11):7287-7296, Oxford University Press, United Kingdom (Jun. 2009).

Tokuyama, H., et al., "V Gamma 9 V Delta 2 T Cell Cytotoxicity Against Tumor Cells is Enhanced by Monoclonal Antibody Drugs—rituximab and Trastuzumab," International Journal of Cancer 122(11):2526-2534, Wiley-Liss, United States (Jun. 2008).

Topalian, S.L., et al., "Safety, Activity, and Immune Correlates of Anti-PD-1 Antibody in Cancer," The New England Journal of Medicine 366(26):2443-2454, Massachusetts Medical Society, United States (Jun. 2012).

Vantourout, P., et al., "Immunological Visibility: Posttranscriptional Regulation of Human NKG2D Ligands by the EGF Receptor Pathway," Science Translational Medicine 6(231):231ra49, pp. 1-14, American Association for the Advancement of Science, United States (Apr. 2014).

Wang, R.F., et al., "Cloning Genes Encoding MHC Class II-restricted Antigens: Mutated CDC27 as a Tumor Antigen," Science 284(5418):1351-1354, American Association for the Advancement of Science, United States (May 1999).

Willcox, C.R., et al., "Cytomegalovirus and Tumor Stress Surveillance by Binding of a Human ?d T Cell Antigen Receptor to Endothelial Protein C Receptor," Nature Immunology 13(9):872-879, Nature America Inc, United States (Sep. 2012).

Wrobel, P., et al., "Lysis of a Broad Range of Epithelial Tumour Cells by Human Gamma Delta T Cells: Involvement of NKG2D Ligands and T-cell Receptor- Versus NKG2D-dependent Recognition," Scandinavian Journal of Immunology 66(2-3):320-328, Blackwell Scientific Publications, United Kingdom (Aug.-Sep. 2007).

Zheng, J., et al., "?d-T Cells: An Unpolished Sword in Human Anti-infection Immunity," Cellular & Molecular Immunology 10(1):50-57, Nature Pub. Group, China (Jan. 2013).

Wu, D., et al., "Ex vivo expanded human circulating V[delta]1 [gamma] [delta]T cells exhibit favorable therapeutic potential for colon cancer", Oncoimmunology 4(3):e992749, Taylor & Francis, United Kingdom (Mar. 2015).

Zadionchenko E.V., "Gamma delta T-oriented immunotherapy for atopic dermatitis," Abstract of dissertation, Moscow, 2005, 48 pages.

Mao, C., et al., "Tumor-Activated TCRγδ+ T Cells from Gastric Cancer Patients Induce the Antitumor Immune Response of TCRαβ+ T Cells via Their Antigen-Presenting Cell-Like Effects," Journal of Immunol Research, 2014:593562, Hindawi Publishing, United Kingdom (Mar. 2014).

Genbank, "interleukin-2 precursor [*Homo sapiens*]," Accession No. NP_000577.2, accessed at https://www.ncbi.nlm.nih.gov/protein/NP_000577.2/, accessed on Jun. 18, 2025, 3 pages.

Genbank, "interleukin-15 preproprotein [*Mus musculus*]," Accession No. NP 001241676.1, accessed at https://www.ncbi.nlm.nih.gov/protein/NP_001241676.1/, accessed on Jun. 18, 2025, 3 pages.

(56)     References Cited

OTHER PUBLICATIONS

Genbank, "interleukin-2 precursor [*Mus musculus*]," Accession No. NP_032392.1, accessed at https://www.ncbi.nlm.nih.gov/protein/NP_032392.1/, accessed on Jun. 18, 2025, 3 pages.

Genbank, "interleukin-15 isoform 1 preproprotein [*Homo sapiens*]," Accession No. NP_000576.1, accessed at https://www.ncbi.nlm.nih.gov/protein/NP_000576.1/, accessed on Jun. 18, 2025, 3 pages.

Genbank, "interleukin-15 isoform 2 preproprotein [*Homo sapiens*]," Accession No. NP_751915.1, accessed at https://www.ncbi.nlm.nih.gov/protein/NP_751915.1/, accessed on Jun. 18, 2025, 3 pages.

Von Lilienfeld-Toal, M., et al., "Activated γδ T cells express the natural cytotoxicity receptor natural killer p44 and show cytotoxic activity against myeloma cells," Clinical and Experimental Immunology 144(3):528-533, British Society of Immunology, United Kingdom (Jun. 2006).

EXPANSION OF NON-HAEMATOPOIETIC TISSUE-RESIDENT GAMMA DELTA T CELLS AND USES OF THESE CELLS

The present invention relates to a method for expanding non-haematopoietic tissue-resident γ6 T cells ex vivo. The term "non-haematopoietic tissue-resident γ6 T cells" refers to subsets of T lymphocytes that reside within non-haematopoietic tissues, rather than within lymphoid organs and blood. Such cells include non-Vδ2 cells, e.g. Vδ1, Vδ3 and Vδ5 cells. The invention also relates to the use of these cells in adoptive T cell therapy and in chimeric antigen receptor therapy, as well as their use in a method of screening for checkpoint modulators. The invention also relates to the cells produced as a result of ex vivo expansion of non-haematopoietic tissue-resident γ6 T cells.

CROSS-REFERENCE TO RELATED APPLICATIONS

This application is a continuation of U.S. application Ser. No. 15/771,875, now U.S. Pat. No. 11,618,885, filed Apr. 27, 2018, which is a 371(c) of PCT/EP2016/076264, filed Oct. 31, 2016, each of which is hereby incorporated by reference in its entirety.

BACKGROUND TO THE INVENTION

The growing interest in T cell immunotherapy for cancer has focused on the evident capacity of subsets of CD8+(1-4) and CD4+αβ (5, 6) T cells to recognise cancer cells and to mediate host-protective functional potentials, particularly when de-repressed by clinically mediated antagonism of inhibitory pathways exerted by PD1(7, 8), CTLA4 (9, 10) and other receptors (11). Nonetheless, many questions remain. For example, there seem to be many major clinical scenarios in which the efficacy of such treatments seems poor (11); there are often profound adverse events (AEs) (12); the capacity to predict either efficacy or AEs is extremely limited (13); and there is very little explanation of the interactions that allow the host to sense tumour cells (so-called "immunogenicity") that must necessarily precede the activation of conventional, antigen-specific CD8+ and CD4+αβ T cell responses.

In these regards, many scientists and clinicians alike are re-assessing the potential of γδ T cells, a third lineage of lymphocytes with somatically-generated receptors that are as strongly conserved evolutionarily as αβ T cells and B cells. There are in essence two sub-groups of human γδ T cells: one that is dominant in human peripheral blood, mostly expressing a Vδ2 T Cell Receptor (TCR); and one that is dominant in non-haematopoietic tissues, the majority expressing a Vδ1 TCR, with smaller populations expressing TCRs that contain a Vδ3 or a Vδ5 chain or some other non-Vδ2 chain (14).

In most adults, Vδ2 cells comprise at steady-state only a small and highly variable component of blood T cells (0.01-5%), but the cells expand rapidly, transiently reaching up to ~25% of CD3+ cells, following challenge by a broad spectrum of agents, including numerous bacteria and parasites (14). A major basis for this response is the Vδ2 TCR-mediated recognition of low molecular weight "phospho-moieties", including hydroxyl-methyl but-2-enyl pyrophosphate (HMBPP) (15), an intermediate in a critical microbial pathway of synthesis of cholesterol and of other lipids that are used to modify proteins, e.g. by geranylation or farnesylation. In primates, this synthesis occurs via the mevalonate pathway, one intermediate of which—isopentenyl pyrophosphate (IPP)—is expressed at very high levels in virus-infected and transformed cells, and is also a target of Vδ2 TCR-mediated recognition (16).

In addition, most Vδ2 T cells express high levels of the NKG2D receptor that can activate or co-stimulate (together with the TCR) the cells' cytolytic potentials upon engaging NKG2D ligands, e.g. MICA, MICB, and ULBP. Those ligands are host proteins that are upregulated when cells are exposed to agents such as oxidative or osmotic stress or ultraviolet light. These agents promote hyper-active signalling of the epidermal growth factor receptor (EGFR) pathway, which is also commonly dysregulated in human solid tumours (17).

The capacity of Vδ2 T cells to detect transformed cells using their TCRs and/or NKG2D (18-20), together with their powerful cytolytic capabilities, and an overt potential to present antigens to CD8+ T cells (21), have collectively provoked the view that Vδ2 T cells might be clinically exploited to deliver cancer immunotherapy. This may be achieved by the cells' adoptive transfer, in which regard the failure of γδ T cells to be restricted by MHC significantly and beneficially limits the potential for graft-versus-host disease (GvHD) (22). In order to achieve this, blood-resident Vγ9Vδ2 γδ T cells can be expanded ex vivo by addition of cytokines such as Interleukin (IL)-2, together with exogenous TCR-activating agents such as phospho-moieties (e.g. BrHPP), or together with clinically-approved bisphosphonates (e.g. Zoledronic acid) which inhibit farnesyl pyrophosphate synthase in the mevalonate pathway, thereby inducing accumulation of the TCR-activating moiety, IPP. However, chronic activation of Vγ9Vδ2 cells via agents such as BrHPP can lead progressively to cellular exhaustion and diminished potential for cytotoxicity.

Alternatively, the patients' own γδ T cells may be activated in situ using either pharmacologically modified forms of HMBPP, or clinically-approved aminobisphosphonates. By these approaches, over 250 cancer patients have been treated, seemingly safely, but with only rare incidences of complete remission. One major concern regarding the cells' limited clinical efficacy is their tendency to become irreparably exhausted by chronic antigen exposure. A second major concern is their seeming inefficiency at homing to solid tumours and the tissues harbouring those tumours (23).

Chimeric antigen receptor T cell (CAR-T) therapy is showing promise in the clinic for B cell malignancies. However, with regard to treating solid tumours, the performance of CAR-T cells has to date been below expectations showing less effectiveness at inducing complete tumour responses and high incident rates of off-tumour cytotoxicity (24). As for peripheral blood γδ T cells, a major obstacle to the success of CAR-T approaches for solid tumours is the likely inefficiency of systemic CAR-T cells to migrate to the sites of malignancy and to reside there in a functionally efficacious state (25). Additionally, being based on conventional αβ T cells, CAR-T cells have to overcome immunosuppressive signals in the tumour microenvironment, e.g. those transmitted via the PD1 receptor.

There may be advantages associated with using γδ T cells for CAR-T approaches, because they can be transduced with tumour-reactive chimeric antigen specific TCRs, while retaining their innate capabilities of recognising transformed cells using receptors such as NKG2D. Thus they may simultaneously bring to bear upon tumours adaptive (TCR) and innate (NKG2D)-mediated effects. However, there remains the issue of the seeming inefficiency of human blood γδ T cells at homing to tumours within solid tissues and therein being maintained in an active form. This consideration has provoked a more detailed consideration of γδ T cells that are ordinarily resident in non-haematopoietic tissues.

Such T cells migrate to non-haematopoietic tissues as part of their development and as such are distinct from those T cells, e.g. tissue-resident TCRαβ+ memory T cells (so-called TRM cells) that infiltrate the tissue after systemic priming. Tissue-resident γδ T cells are most well studied in mice, where they have been shown to be prevalent in skin, gut, and reproductive tissues, among other sites. Many such cells have been shown to harbour innate-like functional potentials whereby they can respond to challenges through activation of the NKG2D receptor. The inventors have recently obtained data demonstrating that human skin and intestine likewise harbour large compartments of non-haematopoietic tissue-resident γδ T cells with innate-like activities. And yet it is striking that the study of malignancies, inflammation, atopy, allergy, and other pathologies that form within non-haematopoietic tissues has largely failed to consider the potential impact of these innate-like human T cells that reside within the tissues in which pathological lesions occur.

Human γδ T cells resident within non-haematopoietic tissues are much less well studied because their localisation renders the cells harder to sample, and because there has been no established means of culturing them. Of the relatively sparse information available, this subtype comprises a diversity of cells with non-MHC-restricted cytolytic potential, which, because they do not express Vγ2-containing TCRs, are wholly unreactive to low molecular weight phospho-moieties. Although few precise TCR-specificities are known for such cells, available data suggest that the cells are reactive to self-antigens, such as Endothelial Protein C Receptor (EPCR), which is over-expressed by cytomegalovirus (CMV)-infected cells and by many solid tumours (32). Non-haematopoietic tissue-associated γδ T cells also commonly express NKG2D (14). Given these properties, and the cells' physiologic residence within non-haematopoietic tissues such as the skin and gut, the adoptive transfer of such cells to cancer patients might be considerably more effective at targeting solid tumours and potentially other immunopathologies.

To exploit non-Vδ2 cells for immunotherapy requires either a means to expand the cells in situ or to harvest them and expand them ex vivo prior to re-infusion. The latter approach has been adopted because there are no known TCR-activating agents that have the proven capacity to expand large numbers of non-Vδ2 cells in situ. To overcome the challenge of limited availability of non-haematopoietic tissues, some researchers have attempted to expand the very small numbers of non-Vδ2 cells from the blood wherein Vδ2-expressing cells are the dominant subset, making the assumption that these cells are equivalent to tissue-resident non-Vδ2 cells. The small numbers of non-Vδ2 γδ T cells found in the blood expand substantially during active CMV infection, show superior reactivity toward CMV by comparison to Vδ2 T cells, and seem able to protect the human foetus in cases of CMV infection in utero. Additionally, CMV-reactive non-Vδ2 γδ T cells seemingly protect transplant patients from CMV re-activation during immunosuppression, and via cross reactivity to transformed cells, decrease the risk of secondary malignancies (26). Similarly, there are data suggesting that γδ T cells play beneficial roles in controlling HIV infection, in which instance non-Vδ2 γδ T cells are expanded in the blood relative to Vδ2 T cells (24).

Blood resident non-Vδ2 cells have been expanded ex vivo by addition of exogenous agents that either directly activate TCR signalling, e.g. by using an agent such as an anti-CD3 antibody, pan γδ-TCR-specific antibody or phytohemagglutinin (PHA), or by co-culturing stimulated non-Vδ2 T cells with artificial Antigen Presenting cells (aAPC), wherein direct contact between the γδ T cells and the aAPC is required for non-Vδ2 T cell expansion ex vivo (41-44). Alternatively, cells have been expanded by promoting NKG2D receptor signalling by use of immobilised recombinant MICA (an NKG2D ligand), for example as was used to sustain the proliferation of γδ T cell cultures ex vivo from epithelial cancer-infiltrating lymphocytes (TILs) (28). In sum, the current methods of expansion ex vivo of Vδ2-expressing blood γδ T cells or of non-Vδ2 blood γδ T cells require addition of agents, invariably promoting activation of the TCR and/or NKG2D receptors together with supplementary cytokines, such as interleukin-2 (IL-2) (41-44). This combination of receptor-activating signals and cytokines reflects the standard approach to culturing and expanding T cells, broadly adopted by the community. To date, no method has been described to substantially expand γδ T cells resident in non-haematopoietic tissue. Such a method is described here.

SUMMARY OF THE INVENTION

As part of a phenotypic and functional characterisation of human skin T cells, the present inventors have isolated a distinct and large population of γδ T cells normally resident within non-haematopoietic tissues and with unique properties relative to αβ T cells and blood-resident γδ T cells. The inventors have found that the cells show strong, TCR-independent, innate-like responses to NKG2D-ligands and to cytokines. Whereas efforts at expansion of primary αβ T cells have commonly employed co-culturing with other supporting cells as a source of beneficial growth factors (29), the present inventors have shown unexpectedly that the γδ T cells resident in skin and other non-haematopoietic tissues are profoundly and specifically suppressed by co-culturing these cells in contact with autologous dermal fibroblasts and potentially other stromal components, such as keratinocytes and endothelial cells. Relief of such interactions permits the cells to be rapidly expanded in large quantities for potential clinical applications.

Furthermore, in contrast to efforts to date to expand blood- and tumour-derived γδ T cells, the present inventors have shown that such non-haematopoietic tissue-resident γδ T cells can be expanded without deliberate addition of any exogenous agents that activate their TCR or NKG2D signalling pathways.

Disclosed herein is a novel means to effectively and reproducibly isolate and expand γδ T cells from human or non-human animal non-haematopoietic tissue, such as skin and intestine. The expansion is promoted by disrupting the contact of non-haematopoietic tissue-derived non-Vδ2 T cells with autologous fibroblasts and potentially other stromal components, and is sustained by culture in interleukin-2 (IL-2) and/or interleukin-15 (IL-15).

The expansion is highly selective since the expansion of αβ T cells or of Vδ2-expressing T cells or of NK cells is not induced by the disruption of their contacts with autologous fibroblasts (FIGS. 3A, 3C, and 3D). This expansion of non-haematopoietic tissue-resident γδ T cells by release from fibroblast-mediated checkpoint modulation also led to the "spontaneous" activation of the cells' effector potentials (FIGS. 5A and 5B), which are highly desirable in the context of anti-tumour activity. These developments permit non-haematopoietic tissue-resident γδ T cells to be expanded in culture and activated for potential use as "off-the-shelf" cell infusions to patients. At the same time, the development of an antibody or other form of inhibitor of the checkpoint modulation of tissue-resident γδ T cells by fibroblasts (or other stromal or epithelial cells) should permit non-haematopoietic tissue-resident γδ T cells to be activated in situ, for example in a cancer patient, via checkpoint-blockade.

The capacity to obtain and to grow γδ T cells from non-haematopoietic tissues (e.g. skin) has identified clear differences from blood-derived Vδ1 T cells. For example, skin-derived Vδ1 T cells show markers of prior T cell activation such as CD69 expression, ICOS and TIM3 positivity as well as little or no expression of the classic co-stimulatory molecule, CD28 (FIG. 10A). Furthermore they show high expression of NKG2D. In contrast, Vδ1 T cells derived from human blood do not express CD69 or TIM3, express only minor levels of ICOS, and are also positive to some degree for expression of CD28. Moreover, NKG2D expression by blood-derived Vδ1 T cells is much lower compared to its expression by skin-derived Vδ1 T cells, and whereas skin-derived Vδ1 T cells show innate-like reactivity to NKG2D ligands such as recombinant MICA in the absence of stimulation of the T cell receptor, blood-derived Vδ1 T cells do not (FIG. 10B). γδ T cells from non-haematopoietic tissues as described herein may also display increased expression of CCR3, CD39, CD11b, IL-13 and/or CD9 relative to blood-derived Vδ1 T cells and other lymphocyte populations.

In a first aspect, the invention provides a method for expanding non-haematopoietic tissue-resident γδ T cells in vitro, the method comprising culturing lymphocytes obtained from non-haematopoietic tissue of humans or non-human animals in the presence of IL-2 and/or interleukin-15 (IL-15), wherein the lymphocytes are not in direct contact with stromal or epithelial cells during culture.

Preferably, the lymphocytes are not in direct contact with fibroblasts during culture The γδ T cells are ordinarily resident in non-haematopoietic tissue in vivo.

Preferably, the method comprises culturing the lymphocytes obtained from human or non-human animal non-haematopoietic tissue in the presence of IL-2 and IL-15.

In some embodiments, the lymphocytes obtained from human or non-human animal non-haematopoietic tissue may be cultured in the absence of TCR activators or co-stimulators that induce T cell activation. For example, the lymphocytes may be cultured in the absence of TCR pathway agonists, e.g. CD3 activators, such as anti-CD3 antibodies, in the presence or absence of CD28 activators.

Addition of such exogenous activators of TCR signalling is not required for expansion of non-haematopoietic tissue-resident γδ T cells using methods of the invention. As such, a suitable γδ expansion medium for use in methods of the invention may be devoid of T cell activation activity, for example αβ T cell or blood γδ T cell activation activity, and may not activate or co-stimulate TCRs.

For example, the γδ expansion medium may be free or substantially free of agents or factors that activate T cell signalling, such αβ TCR activators or co-stimulators, including exogenously added TCR pathway agonists. The γδ expansion medium may comprise IL-2 and/or IL-15. In some embodiments, the γδ expansion medium may comprise one or more additional growth factors, such as cytokines, in additional to IL-2 and/or IL-15. Suitable growth factors do not display T cell activation activity. In other embodiments, the γδ expansion medium may be devoid of growth factors other than IL-2 and/or IL-15; for example the γδ expansion medium may consist of a basal medium supplemented with IL-2 and/or IL-15.

In one embodiment, the lymphocytes obtained from human or non-human animal non-haematopoietic tissue may be cultured in the absence of stromal or epithelial cells. For example, the stromal or epithelial cells may be removed prior to culture. Preferably, the lymphocytes obtained from human or non-human animal non-haematopoietic tissue may be cultured in the absence of fibroblasts. For example, the fibroblasts may be removed prior to culture.

The lymphocytes may be obtained from any suitable human or non-human animal non-haematopoietic tissue, such as skin, the gastrointestinal tract (e.g. colon or ileum), mammary gland tissue, lung, liver, pancreas, adipose tissue or prostate.

The non-haematopoietic tissue-resident γδ T cells are preferably non-Vδ2 cells, most commonly expressing TCRs containing Vδ1 chains, i.e. Vδ1 cells. The non-haematopoietic tissue-resident γδ T cells may also include so-called double negative (DN) γδ T cells, defined as expressing γδ TCRs containing neither Vδ1 nor Vδ2 chains.

The method optionally includes the step of obtaining lymphocytes from human or non-human animal non-haematopoietic tissue. For example, lymphocytes may be obtained from a sample of human or non-human animal non-haematopoietic tissue. A method may comprise providing a sample of human or non-human animal non-haematopoietic tissue and separating the lymphocytes from the non-haematopoietic cells of said sample to produce a population of lymphocytes that is substantially free of stromal cells.

In a second aspect, the invention provides a method for expanding γδ T cells, the method including (i) providing a population of γδ T cells obtained from a non-haematopoietic tissue; and (ii) culturing the γδ T cells substantially free of stromal cell contact to produce an expanded population of γδ T cells.

The population of γδ T cells obtained from the non-haematopoietic tissue may be a substantially pure population of γδ T cells.

The population of γδ T cells obtained from the non-haematopoietic tissue are preferably non-Vδ2 cells, most commonly expressing TCRs containing Vδ1 chains, i.e. Vδ1 cells. The population of γδ T cells may also comprise DN γδ T cells.

The population of γδ T cells obtained from the non-haematopoietic tissue may express one or more additional tissue-resident γδ T cell markers, such as CLA, IL13, CCL1, CD103 and CCR8. In some embodiments, the population of γδ T cells obtained from the non-haematopoietic tissue may comprise Vδ1$^+$ CCR8$^+$ γδ T cells.

The γδ T cells may be cultured in the absence of contact with stromal cells to produce the expanded population of γδ T cells (i.e. there is no contact between γδ T cells and stromal cells in the cell culture).

The γδ T cells may be cultured in the absence of TCR activation signals or co-stimulatory signals. In some embodiments, the culturing step may be performed in stromal cell-conditioned medium, or in the presence of IL-2, IL-15, or a combination thereof. For example, the γδ T cells may be cultured in a γδ expansion medium comprising IL-2 and/or IL-15. A suitable γδ expansion medium may not activate or co-stimulate TCRs. For example, the γδ expansion medium may be free or substantially free of agents or factors that activate T cell signalling, such αβ TCR activators or co-stimulators, including TCR pathway agonists. The γδ expansion medium may comprise IL-2 and/or IL-15. In some embodiments, the γδ expansion medium may comprise one or more additional growth factors, such as cytokines, in addition to IL-2 and/or IL-15. Suitable growth factors do not display T cell activation activity. In other embodiments, the γδ expansion medium may be devoid of growth factors other than IL-2 and/or IL-15; for example the γδ expansion medium may consist of a basal medium supplemented with IL-2 and/or IL-15.

In a third aspect, the invention provides a method for expanding γδ T cells including: (i) providing a non-haematopoietic tissue, the tissue comprising non-haematopoietic cells and γδ T cells; (ii) separating the γδ T cells from the non-haematopoietic cells to produce a population including γδ T cells that is substantially free of stromal cells; and (iii) culturing the population of step (ii) in the absence of TCR activation signals or co-stimulatory signals to produce an expanded population of γδ T cells.

The γδ T cells may, for example, be separated from αβ T cells.

The population of step (ii) may be a substantially pure population of γδ T cells.

The γδ T cells in the population of step (ii) may comprise non-Vδ2 γδ T cells, most commonly expressing TCRs containing Vδ1 chains, i.e. Vδ1 γδ T cells. The γδ T cells in the population of step (ii) may also comprise DN γδ T cells.

The γδ T cells in the population of step (ii) may also comprise γδ T cells that express one or more additional tissue-resident γδ T cell markers, such as CLA, CD103 and CCR8. In some embodiments, the γδ T cells in the population of step (ii) may comprise Vδ1'CCR8' γδ T cells.

The culturing of step (iii) may be substantially free of stromal cell contact with the population of step (ii) and/or is in the absence of TCR activation signals or co-stimulatory signals. For example, the culturing may be performed without contact between γδ T cells and stromal cells. In some embodiments, the culturing of step (iii) is in stromal cell-conditioned medium or in the presence of IL-2, IL-15, or a combination thereof.

In some embodiments, the γδ T cells may be cultured in a γδ expansion medium comprising IL-2 and/or IL-15. A suitable γδ expansion medium may not activate or co-stimulate TCRs. For example, the γδ expansion medium may be free or substantially free of agents or factors that activate T cell signalling, for example TCR activators or co-stimulators, such αβ TCR pathway agonists. In some embodiments, the γδ expansion medium may comprise one or more additional growth factors, such as cytokines, in addition to IL-2 and/or IL-15. Suitable growth factors do not display T cell activation activity. In other embodiments, the γδ expansion medium may consist of a basal medium supplemented with IL-2 and/or IL-15.

An expanded population of γδ T cells according to the second or third aspect may comprise at least 5-fold, at least 10-fold, at least 15-fold, at least 20-fold, at least 30-fold, at least 40-fold, at least 50-fold, at least 100-fold, at least 500-fold, at least 1000-fold or at least 10000-fold more γδ T cells than the γδ T cells obtained from non-haematopoietic tissue or separated from non-haematopoietic cells. The expanded population may generate within 3 days, 5 days, 7 days, 10 days, 14 days, 21 days, or 28 days of culture.

The γδ T cells in the expanded population are preferably Vδ2– T cells. The expanded population of γδ T cells may comprise at least 50%, at least 60%, at least 70%, at least 80%, at least 90%, or at least 95% Vδ1+ cells. The expanded population of γδ T cells may be at least 5%, at least 10%, at least 15%, at least 20%, at least 25%, at least 30%, at least 40%, at least 50%, at least 60%, at least 70%, at least 80% or at least 90% positive for one, two or all three of CCR4, CCR8 and CD103. For example, the expanded population may be at least 10% positive for CD103, at least 30% positive for CCR4 and at least 60% positive for CCR8.

In a fourth aspect, the invention provides a non-haematopoietic tissue-resident γδ T cell or a population thereof obtained by the method of the first, second or third aspect of the invention.

In a fifth aspect, the invention provides a method of screening for a checkpoint modulator of non-haematopoietic tissue-resident γδ T cells, the method comprising:

(i) culturing non-haematopoietic tissue-resident γδ T cells in vitro in direct contact with stromal or epithelial cells (e.g. fibroblasts) in the presence and absence of a test compound or culturing non-haematopoietic tissue-resident γδ T cells in vitro in direct contact with the stromal or epithelial cells (e.g. fibroblasts) in which expression of a test gene within the γδ T cells and/or in the stromal or epithelial cells (e.g. fibroblasts) is altered; and (ii) determining the rate of proliferation or activation of the non-haematopoietic tissue-resident γδ T cells in the presence and absence of the test compound or in the presence and absence of alteration of expression of the test gene in the stromal or epithelial cells (e.g. fibroblasts) and/or γδ T cells, or determining the rate of killing of stromal or epithelial cells (e.g. fibroblasts) in the presence and absence of the test compound or in the presence and absence of alteration of expression of the test gene in the stromal or epithelial cells (e.g. fibroblasts) and/or γδ T cells, wherein if the rate of proliferation or activation of T cells is higher in the presence of the test compound than in the absence of the test compound or higher in the presence of alteration of expression of the test gene in stromal or epithelial cells (e.g. fibroblasts) and/or γδ T cells than in the absence of alteration of the test gene in stromal or epithelial cells (e.g. fibroblasts) and/or γδ T cells and/or if the rate of killing of stromal or epithelial cells (e.g. fibroblasts) is higher in the presence of the test compound than in the absence of the test compound or higher in the presence of alteration of expression of the test gene in stromal or epithelial cells (e.g. fibroblasts) and/or γδ T cells than in the absence of alteration of the test gene in fibroblasts and/or γδ T cells, then the test compound is likely to be a checkpoint modulator or the test gene is likely to be a candidate checkpoint gene or regulator thereof.

Expression of a test gene within the γδ T cells and/or in the stromal or epithelial cells (e.g. fibroblasts) may, for example, be altered by an RNA targeting agent, such as small interfering RNA (siRNA) or small hairpin RNA (shRNA) or by gene editing, e.g. using the CRISPR/Cas system.

In a sixth aspect, the invention provides a method of treating a subject by adoptive T cell therapy, wherein the method comprises administering the non-haematopoietic tissue-resident γδ T cells obtained by the method of the first, second or third aspect of the invention to a subject in need thereof. The subject is preferably a human.

The subject is preferably a human cancer patient or a virus-infected patient, e.g. a CMV-infected patient or an HIV-infected patient.

In a seventh aspect, the invention provides the non-haematopoietic tissue-resident γδ T cells obtained by the method of the first, second or third aspect of the invention for use in a method of treatment of a human or non-human animal by adoptive T cell therapy. A non-haematopoietic tissue-resident γδ T cell may have one or more of the following properties:

(i) displays the phenotype CD69$^{high}$, ICOS$^{high}$TIM3$^{high}$ and CD28$^{low/absent}$ (ii) upregulates one or more of CCR3, CD11b, CD9 and CD39, (iii) produces IFN-γ in response to an NKG2D ligand in the absence of TCR agonists, (iv) produces IL-13 in the absence of TCR agonists, (v) produces one or more of IFN-γ, TNF-α and GM-CSF in response to TCR activation, (vi) produces no or substantially no IL-17 in response to TCR activation, (vii) grows in culture medium containing IL-2 without additional growth factors, (viii) displays a cytotoxic T cell response in the absence of TCR agonists, and/or (ix) displays selective cytotoxicity for tumour cells over normal cells.

In a preferred embodiment, the human is a human cancer patient or a virus-infected patient, e.g. a CMV-infected or HIV-infected patient, wherein the CMV or HIV infection is MICA-related.

In an eighth aspect, the invention provides a method of treating a subject by chimeric antigen receptor therapy, the method comprising administering the non-haematopoietic tissue-resident γδ T cells obtained by the method of the first, second or third aspect of the invention to a subject in need thereof. The subject is preferably a human.

In a preferred embodiment, the subject is a human cancer patient.

In a ninth aspect, the invention provides the non-haematopoietic tissue-resident γδ T cells obtained by the method of the first second or third aspect of the invention for use in a method of treatment of a human or non-human animal by chimeric antigen receptor therapy.

In a preferred embodiment, the human is a human cancer patient.

Each of the embodiments described above may be combined with any one or more of any other embodiments.

These and other aspects of the invention are described in further detail below.

BRIEF DESCRIPTION OF THE FIGURES

FIG. 1A: Skin resident lymphocytes were isolated using an organotypic cell culture published by Clark et al (29), "the Clark protocol". Within CD45+ cells, anti-CD3 was used to stain for T cells and anti-CD56 antibody to identify NK cells, CD3–CD56+, respectively. Within CD3+ cells, antibodies against pan γδ T cell receptor were used to identify skin-resident γδ T cells, and anti-CD8alpha to identify proportions of conventional CD4 and CD8 positive αβ T cells within the CD3+, pan γδ TCR-gate. FIG. 1B shows a summary of these experiments for 7-10 donors using the Clark protocol. Using this protocol, lymphocytes within the human skin are still in contact with the dermal fibroblasts, and were supplemented with either no cytokines at all or with interleukin-2 (IL-2), interleukin-15 (IL-15) or IL-2 and IL-15 indicating the use of cytokines does not change the skin-resident lymphocyte composition with the exception of a slightly larger γδ T cell population when supplementing the culture with IL-15 or IL-2 and IL-15, validating the protocol by Clark et al.

Lymphocyte compositions after a 3 week organotypic skin culture are shown using the cytokines indicated as a summary for 4 donors. FIG. 1C: Skin-resident γδ cells comprise mostly Vδ1-expressing γδ T cells (76.24%±17.3), a small population of Vδ2-expressing T cells (3.06%±6.1) and a population of pan-γδ TCR positive cells that stain negative for Vδ1 or Vδ2, also referred to herein as double negative (DN) γδ T cells (20.7%±13.97). Control staining of the blood of healthy volunteers shows the strong compartmentalization of human γδ T cells, as within the blood the dominant population of γδ T cells expressed the Vδ2 TCR chain. FIG. 1D: Skin-resident γδ T cells show markers previously associated with T cells that have been chronically activated, although these markers are signature indicators of tissue residency rather than necessarily reflecting chronic activation. Histograms show staining of the indicated markers on γδ T cells (filled histogram) versus the appropriate isotype control for each antibody (empty histogram).

FIG. 2A: Skin-resident γδ T cells show strong expression of the activatory and NK cell-associated receptor NKG2D (filled histogram, against isotype represented by the empty histogram). Upon activation using plate-bound recombinant MICA, one of the known ligands for the NKG2D receptors, skin γδ T cells respond without any other stimulation and independent of TCR ligation as the response is abrogated in the presence of blocking NKG2D antibodies. Cells were stimulated for 6 hours in the presence of brefeldin A and 100 units IL-2/ml and were subsequently analysed for degranulation by staining for CD107a. The production of TNFα and INF-γ was analysed by permeabilisation after surface staining and subsequent staining of intracellular cytokines. Phorbol 12-myristate 13-acetate (P) in combination with ionomycin (I) was used as a positive control for activating the T cells. FIG. 2B: Skin-resident γδ T cells show a TH1-biased response. γδ T cells were retrieved using the Clark protocol and stimulated with PMA and ionomycin for 6 h in the presence of brefeldin A and stained for intracellular cytokines. γδ T cells freshly isolated from human skin produce TNFα and IFN-γ upon stimulation, but only small or undetectable amounts of cytokines, e.g. IL-4, IL-17 A, IL-13, IL-22, that are associated with TH2 or TH-17 cells, whereas conventional CD4+αβ T cells show a much broader variety of cytokine production. FIG. 2C: Of lymphocytes derived directly from the human skin, varying levels of the NKG2D receptor are expressed by γδ T cells, CD8a+ conventional αβ T cells and NK cells. Among these cells, NK cells respond to exposure to NKG2D ligands alone, but within T cells it is only the γδ T cell population that shows a cytokine response upon stimulation with NKG2D ligands in the absence of any TCR stimulation (see upper row of flow cytometry dot plots). The response can be blocked using soluble blocking anti-NKG2D antibodies indicating that the response is exclusively mediated via the NKG2D receptor. FIG. 2D: Among skin-resident γδ T cells, only Vδ1 and DN γδ T cells show the innate-like potential to be activated by recombinant MICA alone (indicated by an *). Vδ2-expressing T cells found in small numbers within the skin show no such response.

FIG. 3A: Skin-resident lymphocytes were isolated using the Clark protocol. After a 3 week organotypic culture, skin lymphocytes were harvested and separated from any residual skin cells including fibroblasts and put into tissue culture wells at densities of 1 million lymphocytes/ml and supplemented with 100 U/ml of IL-2. After an additional 3 weeks, resident γδ T cells have strongly expanded and were enriched within the skin lymphocyte culture. This strong proliferative phenomenon was exclusive to skin-resident γδ T cells, represented by the majority of Vδ1+ T cells which proliferated 127.18 fold on average within 3 weeks, whereas conventional αβ T cells only proliferated 5.21 fold on average; that is over 20-fold less well. FIG. 3B: Skin-resident Vδ1+ T cells respond to loss of tissue by strongly up-regulating the marker Ki-67 (indicative of cell cycling) over 14 days (isotype control represented by the empty histogram bordered by a dashed line; Ki-67 expression at day 0 represented by the empty histogram; Ki-67 expression at day 7 represented by the light grey histogram; Ki-67 expression at day 14 staining represented by the dark grey histogram). Furthermore, skin-resident Vδ1 T cells, which in the majority are negative for the IL-2 receptor alpha (CD25) when in contact with dermal stroma, up-regulate CD25 after segregation from the tissue (isotype control: dashed histogram, day 0 staining: light grey histogram, day 7 staining: dark grey histogram).

FIG. 3C: High rates of cell cycling as indicated by median fluorescence intensity (MFI) of Ki-67 are only seen in skin-resident γδ T cells, represented by Vδ1+ T cells, and are seen neither in conventional αβ T cells nor in NK cells where the MFI actually decreases over 14 days. FIG. 3D: Skin lymphocytes segregated from stromal cells show a strongly enriched resident γδ T cell population after a 3 week culture. This γδ T cell population contains a majority of Vδ1 positive cells (77.49%±17.04) and pan γδ TCR positive DN T cells (21.46%±16.92). The initial small Vδ2 T cell population seen in freshly harvested skin lymphocytes using the Clark protocol, is decreasing and almost lost (0.6%±1.204) after a 3 week expansion of tissue γδ T cells.

FIG. 4A: Mixed skin lymphocytes were harvested after organotypic culture as in the Clark protocol after 3 weeks. Mixed lymphocytes were then seeded on top of a confluent layer of autologous skin fibroblasts and in a transwell to control for the presence of soluble inhibitors produced by fibroblasts. After 14 days, fold-wise expansions calculated via absolute cell numbers present were measured for γδ T cells and conventional αβ T cells. Skin-resident γδ T cells showed a strong proliferative response when separated from tissue and in the presence of fibroblasts, but only when not in direct cellular contact with autologous fibroblasts. Conventional αβ T cells did not show such a response in any condition tested. FIG. 4B: Mixed lymphocytes obtained from organotypic culture were seeded onto a monolayer of autologous fibroblasts (light grey histograms) or seeded into empty wells (dark grey histograms) supplemented with IL-2 and cultured for 7 days. Skin-resident Vδ1+ T cells (left panels) as well as pan γδ TCR+, DN T cells (right panels) remained quiescent in the direct presence of fibroblasts but showed strong activation when segregated from dermal organotypic culture and no presence of fibroblasts as indicated by up-regulated expression (MFI) of CD25, the TH-associated transcription factor T-bet, and the cell cycling marker Ki-67 (dashed, empty histograms represent the according isotype control).

FIG. 5A: Skin-resident γδ T cells were allowed to expand for 14 days after separation from the organotypic cell culture. γδ T cells were then flow cytometry-sorted negatively by excluding all conventional T cells stained with a pan αβ TCR monoclonal antibody. 150,000 sorted γδ T cells were then seeded into a 96 flat well culture plate in duplicate and left in culture with neither cytokine supplementation nor supplementation with any activating ligand for 24 hours. Supernatants were harvested and analysed for cytokines produced using the Affymetrix LUMINEX®-based cytokine array. FIG. 5B: Negatively sorted γδ T cells were also seeded onto cancer cell lines seeded 1 day before at a concentration of 10,000 cells per well. As a control, negatively sorted conventional skin αβ T cells were used. T cells were seeded at effector:target ratios indicated in the presence and absence of blocking NKG2D antibody in the presence of IL-2 at 100 U/ml. Skin-resident γδ T cells showed superior killing, as shown by caspase cleaved epithelial specific cytokeratin 18 (CK18) release measured via ELISA, of malignant cell lines over conventional αβ T cells. The cytotoxicity was at least partially mediated via the NKG2D receptor, as shown by its reduction in cultures containing an antibody that blocks the NKG2D receptor.

FIG. 6A: An adaption of the Clark protocol allowed for the isolation of gut-resident lymphocytes. Mixed gut lymphocytes contain a large population of tissue-resident γδ T cells usually comprising mostly Vδ1 cells, but also contain Vδ2 and double negative γδ T cells. FIG. 6B: γδ T cells isolated from gut organotypic culture show similar responses to skin-derived γδ T cells as they upregulate Ki-67 overtime once they are segregated from gut stroma. FIG. 6C: Gut-derived γδ T cells respond to innate-like stimuli such as recombinant MICA by producing IFN-γ and by degranulation, as measured by CD107a up-regulation. FIG. 6D: γδ T cells isolated from gut organotypic culture show similar responses to skin-derived γδ T cells and expand over time in cell culture as seen by the overall enrichment in lymphocyte cultures that lack contact with the gut stroma.

FIG. 7A: Skin-derived γδ T cells stain positive for cutaneous lymphocyte antigen (CLA), the skin homing chemokine receptors CCR4 and CCR8. FIG. 7B: The expression levels are different on expanded γδ T cells derived from the skin or blood, respectively.

FIG. 10A: Skin-derived Vδ1 T cells express high CD69, ICOS and TIM3 and low CD28. Furthermore they show high expression of the activation marker NKG2D. This phenotype is sustained by skin-derived Vδ1 T cells during expansion in vitro. By contrast, Vδ1 T cells derived from human blood lack these signs of activation, do not express CD69 or TIM3, and express only minor levels of ICOS. Compared to skin-derived Vδ1 T cells, NKG2D expression on blood-derived Vδ1 T cells is much lower, whereas blood-derived Vδ1 T cells express the co stimulatory molecule CD28. FIG. 10B: Only skin-derived Vδ1 T cells are reactive to NKG2D ligands such as recombinant MICA in the absence of any other stimulus, such as a ligand for the T cell receptor. Blood-derived Vδ1 or Vδ2 T cells do not show such responsiveness to innate-like stimuli. Cells were seeded into 96 well plates with recombinant MICA or anti-CD3 antibodies or both as indicated. Cells were cultured over 6 h in IL-2 100 U/ml and BFA for the last 4 hours followed by surface antigen staining, permeabilisation and intracellular staining for IFN-γ.

DETAILED DESCRIPTION

Figure 1A:
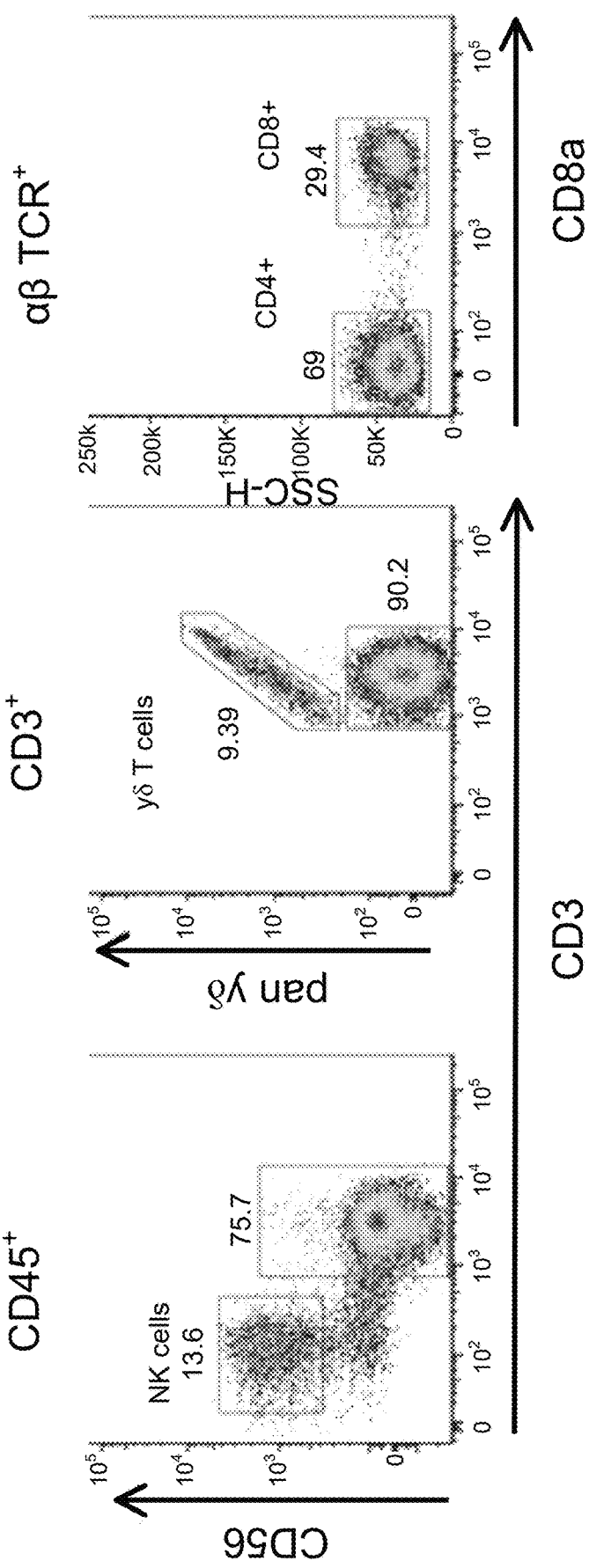
FIGS. 1A-1D show that the human skin comprises a notable population of resident γδ T cells.
Figure 1B:
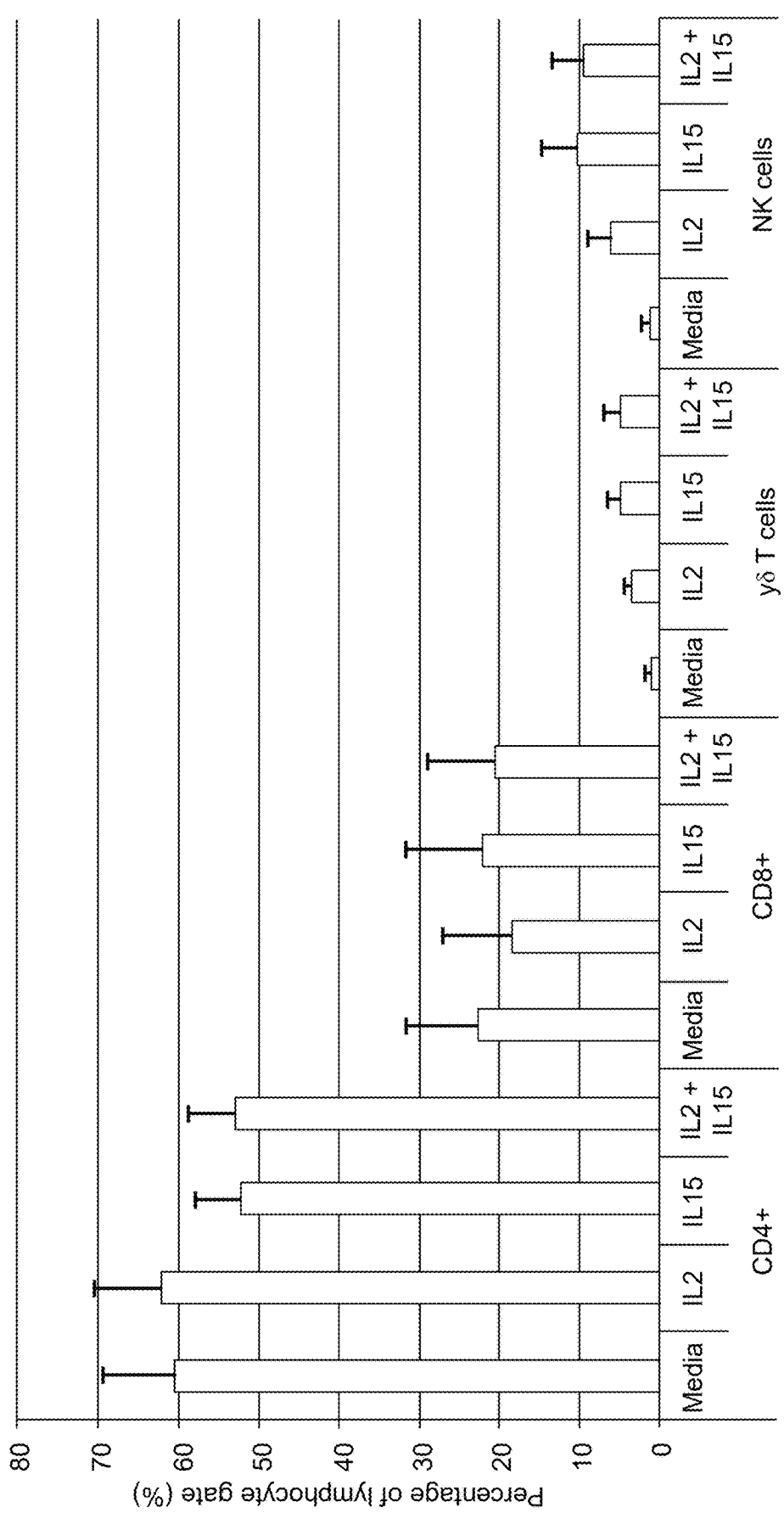

Gamma delta T cells (γδ T cells) represent a small subset of T cells that express on their surface a distinct, defining T-cell receptor (TCR). This TCR is made up of one gamma (γ) and one delta (δ) chain.

There are two major sub-types of human γδ T cells: one that is dominant in the peripheral blood and one that is dominant in non-haematopoietic tissues.

The non-haematopoietic tissue localization of the second human γδ T cell subtype makes it harder to sample and there has been no established means for culturing the cells. To meet this need, the present invention relates to a method of expanding in non-haematopoietic tissue-resident γδ T cells, alternatively referred to herein as non-haematopoietic tissue-native γδ T cells. These γδ T cells are ordinarily resident in non-haematopoietic tissues. Non-haematopoietic tissue-resident γδ T cells for use as described herein may originate from or be obtained from a non-haematopoietic tissue. Non-haematopoietic tissues may contain non-haematopoietic cells and γδ T cells.

The method described herein provides a means of expanding γδ T cells from any human or non-human animal non-haematopoietic tissue that can be removed from a patient, including skin, the gastrointestinal tract (e.g. colon), mammary gland tissue, lung, prostate, liver, spleen and pancreas. The γδ T cells may also be resident in human cancer tissues, e.g. tumours of breast and prostate. In some embodiments, the γδ T cells may be from human cancer tissues. In other embodiments, the γδ T cells may be from non-haematopoietic tissue other than human cancer tissue.

The γδ T cells that are dominant in the blood are primarily Vδ2 T cells, while the γδ T cells that are dominant in the non-haematopoietic tissues are primarily Vδ1 T cells, such that Vδ1 T cells comprise about 70-80% of the non-haematopoietic tissue-resident γδ T cell population. However, some Vδ2 T cells are also found in non-haematopoietic tissues, e.g. in the gut, where they can comprise about 10-20% of γδ T cells (FIG. 6). Some γδ T cells that are resident in non-haematopoietic tissues express neither Vδ1 nor Vδ2 TCR and we have named them double negative (DN) γδ T cells. These DN γδ T cells are likely to be mostly Vδ3-expressing with a minority of Vδ5-expressing T cells.

Therefore, the γδ T cells that are ordinarily resident in non-haematopoietic tissues and that are expanded by the method of the invention are preferably non-Vδ2 T cells, e.g. Vδ1 T cells, with the inclusion of a smaller amount of DN γδ T cells.

As used herein, "double negative" γδ T cells (DN γδ T cells) refer to γδ T cells that express the γδ receptors (i.e., stain positive for pan-TCR) but are negative for Vδ1 and Vδ2 receptors. DN γδ T cells include those that express V6 receptors other than Vδ1 and Vδ2 (e.g., Vδ3, Vδ4, Vδ5, or Vδ8). A cell can be characterized as positive for a marker (e.g., Vδ1') if its expression of the marker is higher than a negative control cell as determined by standard FACS gating methods.

A method described herein may comprise culturing lymphocytes obtained from human or non-human animal non-haematopoietic tissue in vitro.

The lymphocytes may be obtained from any suitable human or non-human animal non-haematopoietic tissue. Non-haematopoietic tissue is a tissue other than blood, bone marrow, or thymus tissue. In some embodiments, the γδ T cells are not obtained from particular types of samples of biological fluids, such as blood or synovial fluid. Examples of such suitable human or non-human animal non-haematopoietic tissues include skin or a portion thereof (e.g., dermis, epidermis), the gastrointestinal tract (e.g. gastrointestinal epithelium, colon, small intestine, stomach, appendix, cecum, or rectum), mammary gland tissue, lung (preferably wherein the tissue is not obtained by bronchoalveolar lavage), prostate, liver, spleen and pancreas. The γδ T cells may also be resident in human cancer tissues, e.g. breast and prostate. In some embodiments, the γδ T cells are not obtained from human cancer tissue. Non-haematopoietic tissue samples may be obtained by standard techniques e.g., by explant (e.g., biopsy).

The lymphocytes may be obtained by any suitable method that allows isolation of lymphocytes from human or non-human animal non-haematopoietic tissue. One such method is set out in Clark et al. (29), which describes a three-dimensional skin explant protocol for isolating lymphocytes from human skin. An explant may be adhered to a synthetic scaffold to facilitate lymphocyte egress from the explant onto the scaffold. A synthetic scaffold refers to a non-native three-dimensional structure suitable to support cell growth. Synthetic scaffolds may be constructed from materials such as polymers (e.g., natural or synthetic polymers, e.g., poly vinyl pyrolidones, polymethylmethacrylate, methyl cellulose, polystyrene, polypropylene, polyurethane), ceramics (e.g., tricalcium phosphate, calcium aluminate, calcium hydroxyapatite), or metals (tantalum, titanium, platinum and metals in the same element group as platinum, niobium, hafnium, tungsten, and combinations of alloys thereof). Biological factors (e.g., collagens (e.g., collagen I or collagen II), fibronectins, laminins, integrins, angiogenic factors, anti-inflammatory factors, glycosaminoglycans, vitrogens, antibodies and fragments thereof, cytokines (e.g., interleukin-2 (IL-2) or interleukin-15 (IL-15), and combinations thereof) may be coated onto the scaffold surface or encapsulated within the scaffold material to enhance cell adhesion, migration, survival, or proliferation, according to methods known in the art. This and other methods can be used to isolate lymphocytes from a number of other non-haematopoietic tissue types, e.g. gut, prostate and breast. Other examples of suitable methods include enzymatic digestion of the tissue and a "crawl out" method described by Carrasco et al (30) in which tissue is chopped up and IL-2 is added so that the lymphocytes "crawl out".

As mentioned above, any suitable non-haematopoietic tissue may be used, such as skin, the gastrointestinal tract (e.g. colon), mammary gland tissue, lung, prostate, liver, spleen and pancreas.

The non-haematopoietic tissue-resident γδ T cells are preferably obtained from human tissue. However, they may be obtained from non-haematopoietic tissue from any suitable non-human animal, such as mice, rats, dogs, horses and pigs.

A critical step is the deliberate separation, e.g. after some days or weeks of culture, of non-haematopoietic tissue-resident T cells (e.g. within a mixed lymphocyte population, which may for example comprise αβ, γδ2 and non-αδ2 T cells) away from the non-haematopoietic cells, (e.g. stromal cells, particularly fibroblasts) of the tissue from which the T cells were obtained, and the cells' subsequent culture as lymphocytes in cytokines as described below. This permits the selective and marked expansion over the following days and weeks of tissue-derived γδ1 and DN γδ T cells.

As used herein, "separation," "separated" or to "separate" refer to the act of breaking or prohibiting physical contact between distinct cell populations. Separation may be performed, e.g., by forcefully pipetting a mixed population of cells to break inter-membrane associations, or by inducing "crawl-out" of a population of cells from, e.g., a tissue matrix, by culturing with, e.g., chemokines or cytokines, as described by Carrasco et al (30). Separation may be maintained during culture using a transwell culture system or by similar culture methods that prevent physical contact between distinct cell populations.

As used herein, "substantially pure" refers to a purity of greater than 90% by number, mass, or volume. "Substantially free of" refers to having less than 5% by number, mass, or volume of a given component. The lymphocytes obtained from human or non-human animal non-haematopoietic tissue may be cultured for at least 3 days, at least 4 days, at least 5 days, at least 6 days, at least 7 days, at least 8 days, at least 9 days, at least 10 days, at least 2 weeks, at least 3 weeks, or at least 4 weeks.

The method comprises culturing the lymphocytes obtained from human or non-human animal non-haematopoietic tissue in the presence of IL-2. The concentration of IL-2 is preferably at least 10 international units/ml (IU/ml, or U/ml), at least 20 U/ml, at least 30 U/ml, at least 40 U/ml, at least 50 U/ml, at least 60 U/ml, at least 70 U/ml, at least 80 U/ml, at least 90 U/ml or at least 100 U/ml.

Figure 1C:
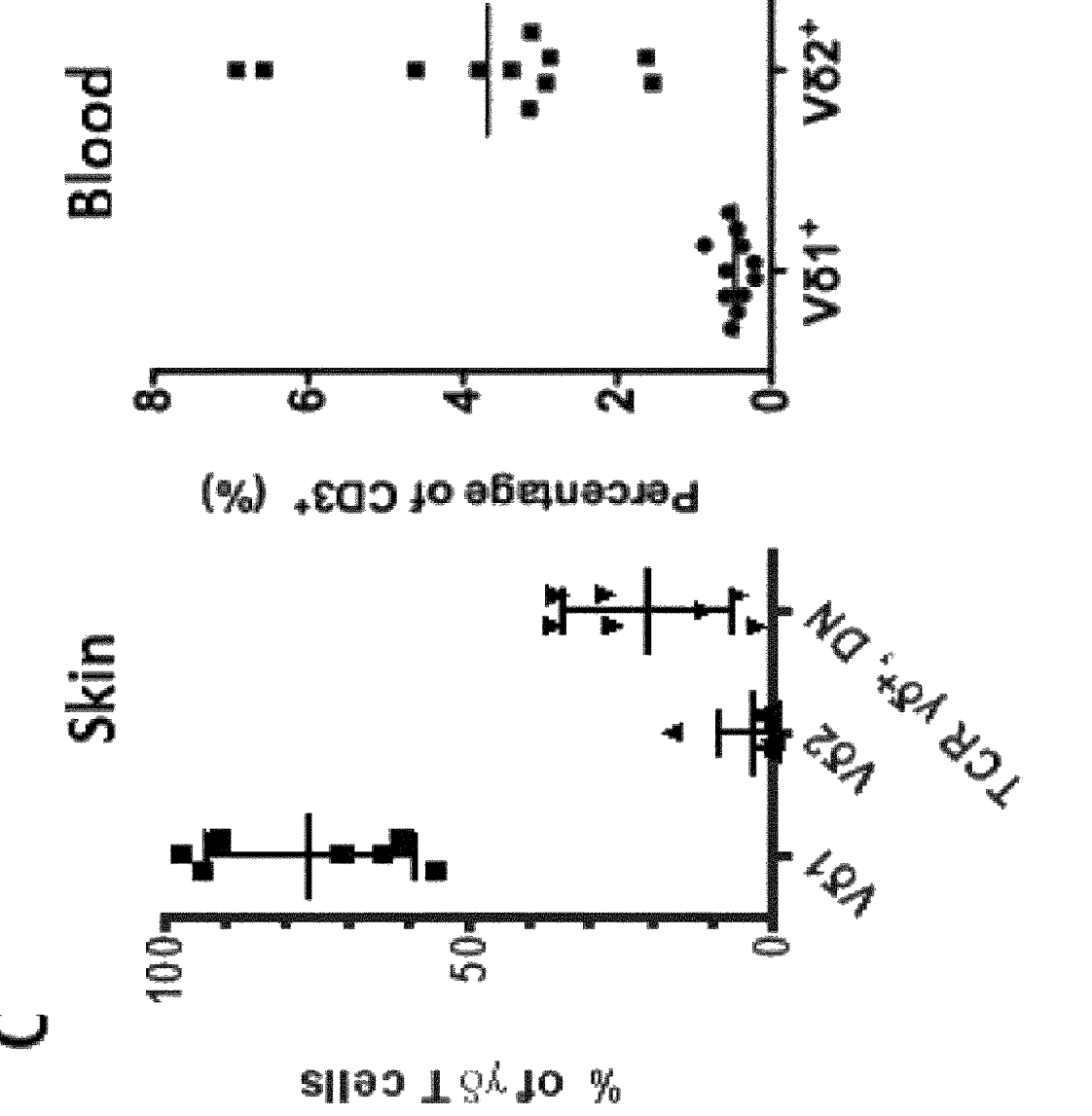
Figure 1D:
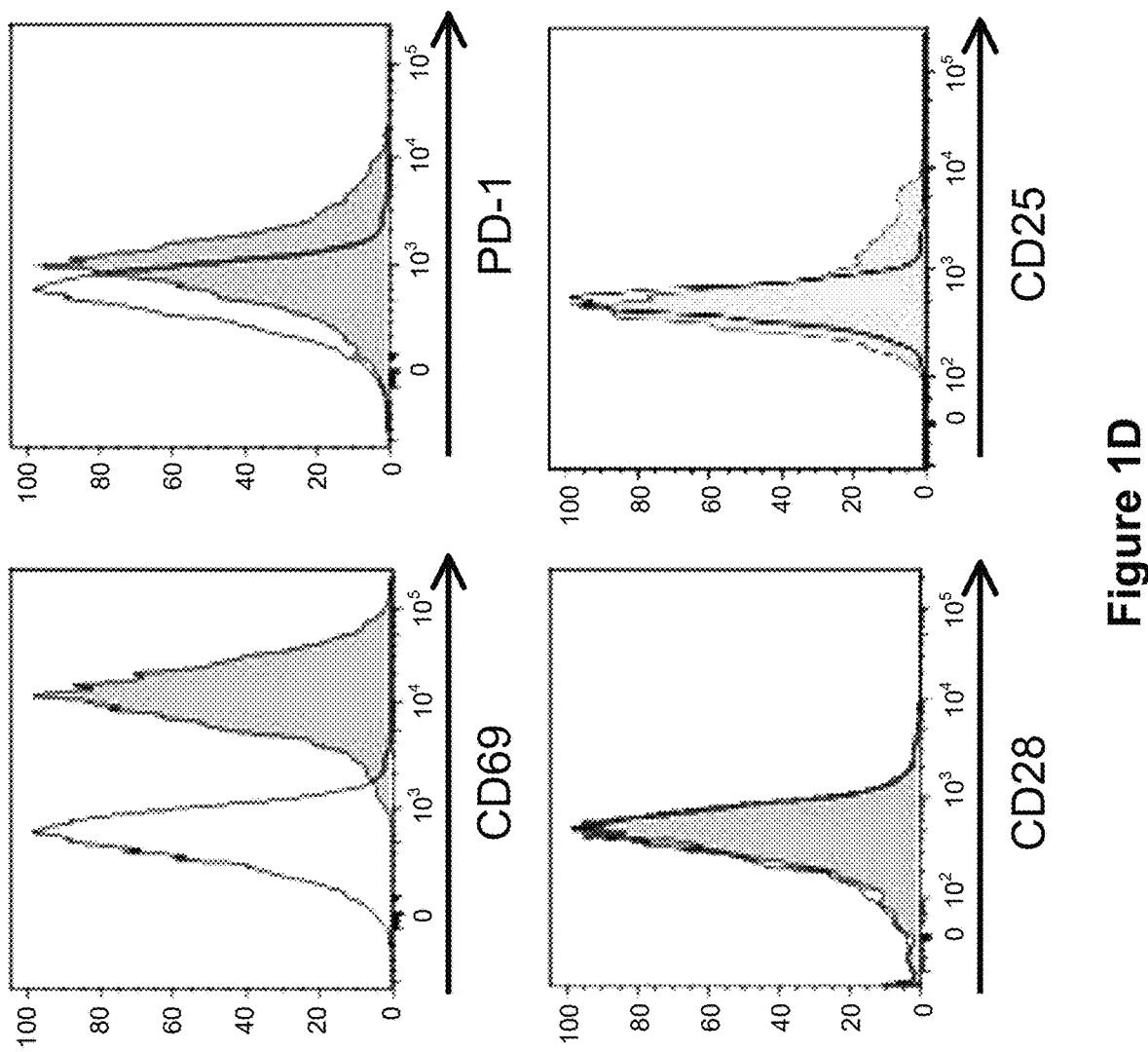

The use of IL-2 to promote the expansion of skin-derived γδ T cells is not obvious because the cells express very low levels of the high affinity IL-2-receptor, known as CD25 (FIG. 1D). However, this receptor is upregulated on discrete subsets of γδ T cells by dissociation from other cell types, such as stromal or epithelial cells (e.g. fibroblasts) (see FIGS. 3B and 4B) rendering the cells highly susceptible to IL-2.

As used herein, "IL-2" refers to wild-type IL-2 (e.g., native or recombinant) or an agent that acts as an agonist for one or more IL-2 receptor (IL-2R) subunits (e.g., IL-2 muteins, long-acting IL-2 analogues, subunits thereof, receptor complexes thereof). Such agents can support proliferation of an IL-2-dependent cell line, CTLL-2 (33; American Type Culture Collection (ATCC®) TIB 214). Mature human IL-2 occurs as a 133 amino acid sequence (less the signal peptide, consisting of an additional 20 N-terminal amino acids), as described in Fujita, et al. (34). An IL-2 mutein is a polypeptide wherein specific substitutions to the interleukin-2 protein have been made while retaining the ability to bind IL-2RP, such as those described in US 2014/0046026. The IL-2 muteins can be characterized by amino acid insertions, deletions, substitutions and modifications at one or more sites in or at the other residues of the native IL-2 polypeptide chain. In accordance with this disclosure any such insertions, deletions, substitutions and modifications result in an IL-2 mutein that retains the IL-2RP binding activity. Exemplary muteins can include substitutions of 1, 2, 3, 4, 5, 6, 7, 8, 9, 10 or more amino acids.

Nucleic acid encoding human IL-2 can be obtained by conventional procedures such as polymerase chain reaction (PCR). The amino acid sequence of human IL-2 (Gene ID 3558) is found in Genbank under accession locator NP_000577.2 GI: 28178861. The murine (Mus musculus) IL-2 amino acid sequence (Gene ID 16183) is found in Genbank under accession locator NP_032392.1 GI: 7110653.

The lymphocytes are preferably cultured in the presence of IL-2 and IL-15, as the addition of IL-15 in combination with IL-2 results in enhanced expansion of proliferative non-haematopoietic tissue-resident γδ T cells compared to IL-2 alone. The concentration of IL-15 is preferably at least 10 ng/ml.

IL-15, like IL-2, is a known T-cell growth factor that can support proliferation of an IL-2-dependent cell line, CTLL-2. IL-15 was first reported by Grabstein et al (35) as a 114-amino acid mature protein. The term, "IL-15" as used herein, means native or recombinant IL-15 and muteins, analogs, subunits thereof, or complexes thereof (e.g., receptor complexes, e.g., sushi peptides, as described in WO2007/046006), and each of which will stimulate proliferation of CTLL-2 cells. In the CTLL-2 proliferation assays, supernatants of cells transfected with recombinantly expressed precursor and in-frame fusions of mature forms of IL-15 can induce CTLL-2 cell proliferation.

The term, IL-15, as used herein, also means IL-15 as derived from a variety of mammalian species, including, for example, human, simian, bovine, porcine, equine and murine. An IL-15 "mutein" or "variant", as referred to herein, is a polypeptide substantially homologous to a sequence of a native mammalian IL-15 but that has an amino acid sequence different from a native mammalian IL-15 polypeptide because of an amino acid deletion, insertion or substitution. Variants may comprise conservatively substituted sequences, meaning that a given amino acid residue is replaced by a residue having similar physiochemical characteristics. Examples of conservative substitutions include substitution of one aliphatic residue for another, such as lie, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-15 variants are also encompassed by the invention. Examples of such variants are proteins that result from alternate mRNA splicing events or from proteolytic cleavage of the IL-15 protein, wherein the IL-15 binding property is retained. Alternate splicing of mRNA may yield a truncated but biologically active IL-15 protein. Variations attributable to proteolysis include, for example, differences in the N- or C-termini upon expression in different types of host cells, due to proteolytic removal of one or more terminal amino acids from the IL-15 protein (generally from 1-10 amino acids).

Human IL-15 can be obtained according to the procedures described by Grabstein et al (35) or by conventional procedures such as polymerase chain reaction (PCR). A deposit of human IL-15 cDNA was made with the ATCC® on Feb. 19, 1993 and assigned accession number 69245.

The amino acid sequence of human IL-15 (Gene ID 3600) is found in Genbank under accession locator NP000576.1 GI: 10835153 (isoform 1) and NP_751915.1 GI: 26787986 (isoform 2). The murine (Mus musculus) IL-15 amino acid sequence (Gene ID 16168) is found in Genbank under accession locator NP_001241676.1 GI: 363000984.

The lymphocytes may be cultured in the absence of IL-6, IL-23 and IL-1B, or in the presence of low concentrations of these cytokines (e.g. less than 20 ng/ml), as the addition of this combination of cytokines appears to reduce proliferation of non-haematopoietic tissue-resident γδ T cells. This is surprising, as these cytokines would have been expected to promote proliferation.

The lymphocytes obtained from non-haematopoietic tissue may be cultured in the absence of agents that activate T cell signalling (e.g. T cell receptor (TCR) pathway agonists). For example, the lymphocytes obtained from non-haematopoietic tissue may be cultured in a medium that does not support or induce the proliferation or activation of αβ T cells and blood-resident γδ T cells. A suitable medium may be free or substantially free of TCR agonists or other agents that activate T cell signalling. In contrast, the culture of γδ T cells from haematopoietic tissues requires the presence of an agent that activates T cell signalling, such as zoledronate (41, 42) or an anti-CD3 antibody, such as OKT3 (43).

Agents that activate T cell signalling refer to compounds that induce proliferation or activation of T cells, such as αβ T cells and/or blood-resident γδ T cells, through TCR signalling or co-stimulation. T cell signalling modulators function by sequential activation of the Src-related protein tyrosine kinases (PTKs), LcK and Fyn, and zeta-chain (TCR) associated protein kinase of 70 kDA (ZAP70). These PTKs lead to phosphorylation of polypeptides including linker activator for T cells (LAT), which leads to downstream stimulation through extracellular signal regulated kinase (ERK), c-Jun N-terminal kinase (JNK), and nuclear factor of activated T-cells (NFAT). Co-stimulation, for example through CD28 and CD45, can enhance phosphorylation and enhance TCR signalling pathways. Thus, any agent that targets a part of the TCR or co-stimulatory pathway can activate T cell signalling. Agents that activate T cell signalling may be soluble or membrane bound and may, for example, be presented on cells, such as artificial antigen presenting cells (aAPCs). Suitable aAPCs for activating T cell signalling are known in the art (44).

In some embodiments, the lymphocytes may be cultured in the absence of exogenously added T cell receptor pathway agonists, such as CD3 and/or CD28 activators (e.g. anti-CD3 and/or anti-CD28 monoclonal antibodies); phytohemagglutinin (PHA); concanavalin A, synthetic phosphoantigens, such as BrHPP (bromohydrin pyrophosphate), 2M3B1PP (2-methyl-3-butenyl-1-pyrophosphate), HMBPP ((E)-4-Hydroxy-3-methyl-but-2-enyl pyrophosphate), or IPP (isopentenyl pyrophosphate); N-bisphosphonates, such as zoledronate; recombinant CD70; anti-CD2 monoclonal antibodies; anti-CD27 monoclonal antibodies; anti-pan-TCRγδ antibodies; anti-CD277 monoclonal antibodies; or artificial antigen presenting cells (aAPCs). Agents that activate T cell signalling also include cell-surface bound molecules, such as MHC or HLA complexes associated with antigen-presenting cells (APCs) or artificial APCs. Suitable methods of activating T cells by exogenously adding TCR pathway agonists are well known in the art and summarized in Figure 1 of Deniger et al (44).

For example, the lymphocytes may be cultured in a medium that is free or substantially free of exogenously added T cell receptor pathway agonists. Addition of such T cell receptor signalling activating agents is not required for expansion of non-haematopoietic tissue resident γδ T cells using the method of the invention. In contrast, the expansion of haematopoietic tissue-derived γδ T cells requires the presence of both IL-2 and a T cell receptor signalling activating agent, such as zoledronate (41, 42).

In some embodiments, the lymphocytes may be cultured in conditioned media from stromal cell cultures to provide supplements for γδ T cell growth.

In some embodiments, the γδ T cells may be cultured in a γδ expansion medium comprising IL-2 and/or IL-15. A suitable γδ expansion medium is devoid of T cell activation activity, for example αβ T cell or blood γδ T cell activation activity, and may, for example, be free or substantially free of TCR agonists or co-stimulatory agents. In some embodiments, the γδ expansion medium may comprise one or more additional growth factors, such as cytokines, in additional to IL-2 and/or IL-15. Suitable growth factors do not display T cell activation activity. In other embodiments, the γδ expansion medium may be devoid of growth factors other than IL-2 and/or IL-15; for example the γδ expansion medium may consist of a basal medium supplemented with IL-2 and/or IL-15.

Numerous basal culture media suitable for use in the proliferation of γδ T cells are available, in particular complete media, such as AIM-V, Iscoves medium and RPMI-1640 (Life Technologies). The medium may be supplemented with other media factors, such as serum, serum proteins and selective agents, such as antibiotics. For example, in some embodiments, RPMI-1640 medium containing 2 mM glutamine, 10% FBS, 10 mM HEPES, pH 7.2, 1% penicillin-streptomycin, sodium pyruvate (1 mM; Life Technologies), non-essential amino acids (e.g. 100 μM Gly, Ala, Asn, Asp, Glu, Pro and Ser; 1×MEM non-essential amino acids Life Technologies), and 10 μl/L β-mercaptoethanol. The basal medium may be supplemented with IL-2 and/or IL-15 at standard concentrations which may readily be determined by the skilled person by routine experimentation.

Conveniently, cells are cultured at 37° C. in a humidified atmosphere containing 5% $CO_2$ in a suitable culture medium.

The γδ T cells may be cultured as described herein in any suitable system, including stirred tank fermenters, airlift fermenters, roller bottles, culture bags or dishes, and other bioreactors, in particular hollow fibre bioreactors. The use of such systems is well-known in the art.

Methods and techniques for the culture of lymphocytes are well-known in the art (36-39).

During culture, the lymphocytes are not in direct contact with stromal or epithelial cells. This is because direct contact of the lymphocytes with stromal or epithelial cells appears to inhibit expansion of tissue-resident γδ T cells.

Stromal cells are non-haematopoietic connective tissue cells of any organ and support the function of the parenchymal cells of that organ. Examples of stromal cells include fibroblasts, pericytes, mesenchymal cells, keratinocytes, endothelial cells and non-haematological tumour cells. Preferably, the lymphocytes are not in direct contact with fibroblasts during culture.

Epithelial cells are non-haematopoietic cells that line the cavities and surfaces of blood vessels and organs throughout the body. They are normally squamous, columnar or cuboidal in shape and can be arranged as a single layer of cells, or as layers of two or more cells.

Fibroblasts and/or other stromal or epithelial cells are preferably present during culture of the lymphocytes, as factors secreted by these cells may promote the expansion of non-haematopoietic tissue-resident γδ T cells, but are not in direct contact with the lymphocytes, as direct contact inhibits expansion of non-haematopoietic tissue-resident γδ T cells. For example, the lymphocytes may be cultured in transwells, which allow physical separation of the lymphocytes and fibroblasts. Examples of fibroblast cell lines which may be used include human foreskin fibroblasts (e.g. BJ (ATCC® CRL-2522™)), normal skin fibroblasts (e.g. CCD-1059Sk (ATCC® CRL-2072™)) and lung fibroblasts (e.g. HEL 299 (ATCC® CRL-137™)).

Using the Clark protocol, non-haematopoietic tissue resident lymphocytes can be harvested and separated from stromal cells, such as dermal fibroblasts, e.g. by firm pipetting. The lymphocyte harvest may further be washed through a 40 μm nylon mesh in order to retain fibroblast aggregates that may have become loose during the process. Lymphocytes may also be isolated using fluorescent or magnetic associated cell sorting using, for example, CD45 antibodies. In order to minimise activation of the T cells, they may also be sorted solely on the criteria of their forward and side scatter properties. Lymphocytes may then be grown in isolation of stromal cells (e.g. fibroblasts) or in their presence but not in direct contact. For example, the lymphocytes may be grown in a transwell basket with a confluent monolayer of fibroblasts in the cell culture well below to allow the exchange of soluble growth factors produced by the fibroblasts, without allowing any direct contact. Alternatively, the fibroblasts may be cultured in a transwell basket with the lymphocytes growing in the cell culture well below. One may also use conditioned media by non-haematopoietic cells (e.g., fibroblasts) to supplement lymphocyte expansions.

Conditioned media contains soluble factors secreted by non-haematopoietic cells (e.g., stromal cells, such as fibroblasts). Conditioned media may or may not contain the cells that secreted the factors. For example, γδ T cells can be cultured in the presence of cells that secrete conditioning factors during γδ T cell culture. Alternatively, the non-haematopoietic cells can be removed from the media prior to γδ T cell culture, leaving their secreted factors in the media. Conditioned media also includes media that has been supplemented with non-haematopoietic cell factors that have been previously prepared (e.g., as a concentrate or a lyophilized powder).

Although stromal or epithelial cells are preferably present during culture of the lymphocytes (but are not in direct contact with the lymphocytes), they may be removed so that the lymphocytes are cultured in the absence of stromal or epithelial cells, e.g. in the absence of fibroblasts.

In some embodiments, following expansion of non-haematopoietic tissue resident γδ T cells in the absence of agents that activate T cell signalling, such as exogenously added T cell receptor pathway agonists, as described above, the expanded γδ T cells may be further cultured in the presence of one or more agents that activate T cell signalling, such as exogenously added T cell receptor pathway agonists, and/or one or more growth factors, such as cytokines. Following expansion as described herein and optional further culturing, non-haematopoietic tissue resident γδ T cells may be isolated or further purified, stored, admixed with other reagents, such as pharmaceutically acceptable excipients and/or used, as required.

Figure 7A:
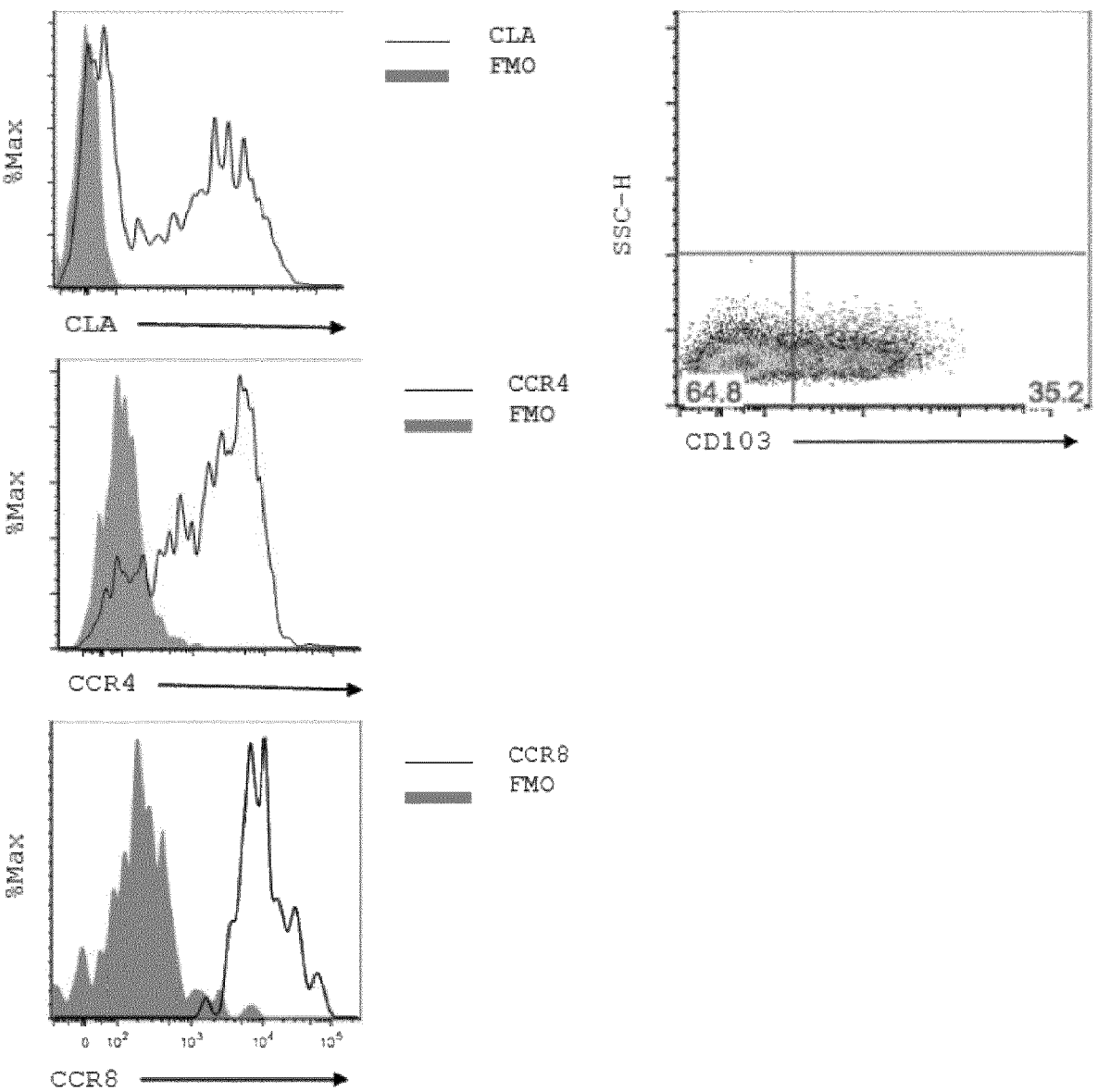
FIGS. 7A and 7B show the tissue phenotype of expanded skin-derived γδ T cells.
Figure 7B:
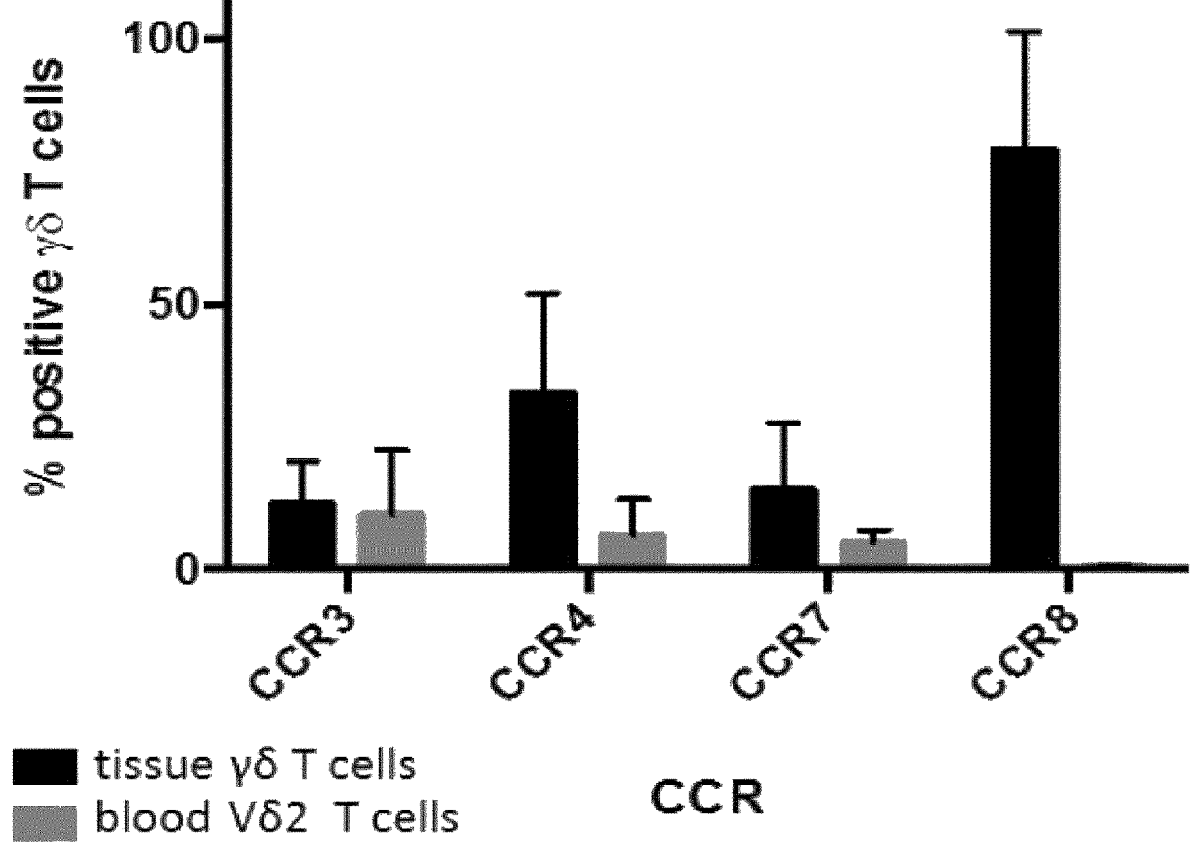

Non-haematopoietic tissue-resident γδ T cells produced by the method of the invention may be distinguished from other blood-derived γδ T cells in that they respond to NKG2D ligand (MICA), which is strongly associated with malignancy, in the absence of any T cell receptor stimulating ligand, for example by increased production of TNFα, IFNγ, and CD107a (FIGS. 2A to 2D, 10A and 10B). They also execute a cytotoxic T cell response without undergoing any exogenous pharmacological or ligand mediated activation of the T cell receptor and are therefore cytotoxic in the absence of stimulation (FIG. 3 and FIG. 5). This means that compared with other γδ T cells, with αβ T cells or with NK cells, the non-haematopoietic tissue-resident γδ T cells produced by the method of the invention are unique in their ability to respond and proliferate in the absence of addition of any exogenous agents activating T cell receptor signalling (FIG. 3). The non-haematopoietic tissue-resident γδ T cells produced by the method of the invention also stained positive for CD69 and PD-1, lacked expression of CD28, and showed only low levels of CD25 (see FIG. 1D). This combination of markers is not expressed by blood-derived γδ T cells. Furthermore they showed higher expression of tissue homing receptors such as CCR4 and CCR8 compared to blood derived, expanded Vd2 γδ T cells (FIG. 7B). Non-haematopoietic tissue-resident γδ T cells produced by methods of the invention may be culturable in the presence of IL2 and/or IL15 without TCR agonists or other growth factors. For example, a non-haematopoietic tissue-resident γδ T cell may grow in a medium consisting of RPMI 1640 medium supplemented with IL-2.

A non-haematopoietic tissue-resident γδ T cell produced by the method of the invention may thus have one or more of the following properties:

(i) displays the phenotype CD69$^{high}$, ICOS$^{high}$, TIM3$^{high}$ and CD28$^{low/absent}$ (ii) upregulates of one or more of CCR3, CD39, CD11b, and CD9

(iii) produces IFN-γ in response to an NKG2D ligand in the absence of TCR agonists, (iv) produces IL-13 in the absence of TCR agonists, (v) produces one or more of IFN-γ, TNF-α and GM-CSF in response to TCR activation, (vi) produces no or substantially no IL-17 in response to TCR activation, (vii) grows in culture medium containing IL-2 without additional growth factors, (viii) displays a cytotoxic T cell response in the absence of TCR agonists and/or (ix) displays selective cytotoxicity for tumour cells over normal cells.

Preferably a non-haematopoietic tissue-resident γδ T cell produced by the method of the invention produces IL-13 in the absence of TCR agonists and/or produces IFN-γ in response to an NKG2D ligand in the absence of TCR agonists.

The γδ T cells obtained by the method of the invention may be used in a method of screening for a checkpoint modulator of non-haematopoietic tissue resident γδ T cells. The identification of such checkpoint modulators may be useful for developing cancer immunotherapies, as the checkpoint modulator is a potential target for cancer therapy.

In order to determine whether a test compound is a checkpoint modulator, non-haematopoietic tissue-resident γδ T cells may be cultured in vitro in direct contact with stromal or epithelial cells (e.g. fibroblasts) in the presence or absence of the test compound. The rate of proliferation or degree of activation of the non-haematopoietic tissue-resident γδ T cells is determined in the presence and absence of the test compound. If the rate of proliferation or degree of activation is higher in the presence of the test compound than in the absence of the test compound, then the test compound is likely to be a candidate checkpoint modulator. This is because the test compound is able to relieve contact inhibition by the stromal or epithelial cells (e.g. fibroblasts).

The test compound is chosen based on its potential to modulate a checkpoint for tissue-resident T cells.

The apparent increase in non-haematopoietic tissue resident γδ T cell proliferation could also be due to inhibition of cell death and can be measured by an increase in T cell count or markers thereof and by reduced expression of markers of programmed cell death. Increased activation can be assessed by measuring release of cytokines such as IFN-γ which are secreted by activated tissue resident γδ T cells.

Alternatively, non-haematopoietic tissue resident γδ T cells may be cultured in vitro in direct contact with stromal or epithelial cells (e.g. fibroblasts), wherein expression of a test gene within the γδ T cells and/or the stromal or epithelial cells (e.g. fibroblasts) or both the cell types is altered. Expression of a test gene within the γδ T cells and/or in the stromal or epithelial cells (e.g. fibroblasts) may, for example, be altered by an RNA targeting agent, such as small interfering RNA (siRNA) or small hairpin RNA (shRNA) or by gene editing, e.g. using the CRISPR/Cas system. The rate of proliferation or degree of activation of the non-haematopoietic tissue-resident γδ T cells is determined in the presence and absence of alteration of expression of the test gene in the stromal or epithelial cells (e.g. fibroblasts) and/or γδ T cells. If the rate of proliferation or activation is higher in the presence of alteration of expression of the test gene in stromal or epithelial cells (e.g. fibroblasts) and/or γδ T cells than in the absence of alteration of the test gene in stromal or epithelial cells (e.g. fibroblasts) and/or γδ T cells, then the test gene is likely to be a candidate checkpoint gene.

Alternatively, if the rate of killing of stromal or epithelial cells (e.g. fibroblasts) is higher in the presence of the test compound than in the absence of the test compound or higher in the presence of alteration of expression of the test gene in stromal or epithelial cells (e.g. fibroblasts) and/or γδ T cells than in the absence of alteration of the test gene in stromal or epithelial cells (e.g. fibroblasts) and/or γδ T cells, then the test compound is likely to be a checkpoint modulator or the test gene is likely to be a candidate checkpoint gene. The rate of killing may, for example, be measured by the quantitation of molecules released by dying cells. A higher rate of cell killing in the presence of the test compound or in the presence of alteration of expression of the test gene in stromal or epithelial cells (e.g. fibroblasts) and/or γδ T cells indicates that the checkpoint that was repressing cell killing has been relieved and one may therefore conclude that the test compound is likely to be a checkpoint modulator or the test gene is likely to be a candidate checkpoint gene.

Examples of fibroblast cell lines which may be used in each embodiment include human foreskin fibroblasts (e.g. BJ (ATCC® CRL-2522™)), normal skin fibroblasts (e.g. CCD-1059Sk (ATCC® CRL-2072™)) and lung fibroblasts (e.g. HEL 299 (ATCC® CRL-137™)) In order to identify a test compound as a candidate checkpoint modulator or in order to identify a test gene as a candidate checkpoint gene, the rate of proliferation and or activation of the γδ T cells in the presence of the test compound or in the presence of alteration of the test gene may be at least 1.5 times, at least 2 times, at least 3 times, at least 4 times or at least 5 times higher than in the absence of the test compound or in the absence of alteration of the test gene. Cell cycling can be measured by a number of means, such as absolute cell numbers on day 0 and day 7, levels of Ki-67 and CD25 expression (which are cell cycling markers) and using cell culture dyes, such CFSE or CELLTRACE™ violet. Cell activation can be measured by the production of effector proteins such as IFN-γ. The apparent increase in proliferation of non-haematopoietic tissue-resident γδ T cells could also be due to inhibition of cell death and can be measured by an increase in T cell count or markers thereof and by reduced expression of markers of programmed cell death.

The γδ T cells obtained by the method of the invention may be used as a medicament, for example for adoptive T cell therapy. This involves the transfer of γδ T cells obtained by the method of the invention into a patient. The therapy may be autologous, i.e., the γδ T cells may be transferred back into the same patient from which they were obtained, or the therapy may be allogeneic, i.e. the γδ T cells from one person may be transferred into a different patient. A method of treatment may comprise;

providing a sample of non-haematopoietic tissue obtained from a donor individual, culturing the γδ T cells from the sample as described above to produce an expanded population, and;

administering the expanded population of γδ T cells to a recipient individual.

The donor individual and the recipient individual may be the same or different.

The γδ T cells may be administered to the patient or subject in need of treatment by any suitable method. For example, the γδ T cells may be administered to the patient or subject in need of treatment intravenously or intra-tumourally.

The patient or subject to be treated is preferably a human cancer patient or a virus-infected patient, e.g., a CMV-infected or HIV infected patient.

As γδ T cells are non-MHC restricted, they do not recognise a host into which they are transferred as foreign, which means that they are less likely to cause graft-versus-host disease. This means that they can be used "off the shelf" and transferred into any recipient, e.g., for allogeneic adoptive T cell therapy.

Because they are normally resident in non-haematopoietic tissues, tissue-resident Vδ1 T and DN γδ T cells are also more likely to home to and be retained within tumour masses than their systemic blood-resident counterparts and adoptive transfer of these cells is likely to be more effective at targeting solid tumours and potentially other non-haematopoietic tissue-associated immunopathologies.

In some embodiments, a method of treatment of an individual with a tumour in a non-haematopoietic tissue may comprise;

providing a sample of said non-haematopoietic tissue obtained from a donor individual, culturing the γδ T cells from the sample as described above to produce an expanded population, and;

administering the expanded population of γδ T cells to the individual with the tumour.

Non-haematopoietic tissue-resident γδ T cells obtained by methods of the invention express NKG2D and respond to a NKG2D ligand (e.g. MICA), which is strongly associated with malignancy. They also express a cytotoxic profile in the absence of any activation and are therefore likely to be effective at killing tumour cells. For example, the non-haematopoietic tissue-resident γδ T cells obtained as described herein may express one or more, preferably all of IFN-γ, TNF-α, GM-CSF, CCL4, IL-13, Granulysin, Granzyme A and B, and Perforin in the absence of any activation. IL-17 A may not be expressed.

The findings reported herein therefore provide compelling evidence for the practicality and suitability for the clinical application of the non-haematopoietic tissue-resident γδ T cells obtained by the method of the invention as an "off-the-shelf" immunotherapeutic reagent. These cells possess innate-like killing, have no MHC restriction and display improved homing to and/or retention within tumours than do other T cells.

The non-haematopoietic tissue-resident γδ T cells obtained by the method of the invention may also be used for CAR-T therapy. This involves the generation of engineered T cell receptors (TCRs) to re-programme the T cell with a new specificity, e.g. the specificity of a monoclonal antibody. The engineered TCR may make the T cells specific for malignant cells and therefore useful for cancer immunotherapy. For example, the T cells may recognise cancer cells expressing a tumour antigen, such as a tumour associated antigen (TAA) that is not expressed by normal somatic cells from the subject tissue. Thus, the CAR-modified T cells may be used for adoptive T cell therapy of, for example, cancer patients.

The use of blood-resident γδ T cells for CAR has been described. However, non-haematopoietic tissue-resident γδ T cells obtained by the method of the invention are likely to be particularly good vehicles for CAR-T approaches, as they can be transduced with chimeric antigen-specific TCRs while retaining their innate-like capabilities of recognising transformed cells, and are likely to have better tumour penetration and retention capabilities than either blood-resident γδ T cells or conventional, systemic αβ T cells. Furthermore, their lack of MHC dependent antigen presentation reduces the potential for graft-versus-host disease and permits them to target tumours expressing low levels of MHC. Likewise, their non-reliance upon conventional co-stimulation, for example via engagement of CD28 enhances the targeting of tumours expressing low levels of ligands for co-stimulatory receptors.

Cancer may be characterised by the abnormal proliferation of malignant cancer cells and may include leukaemias, such as acute myeloid leukaemia (AML), chronic myeloid leukaemia (CML), acute lymphoblastic leukaemia (ALL) and chronic lymphocytic leukaemia (CLL), lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer.

Cancer cells within cancer patient may be immunologically distinct from normal somatic cells in the individual (i.e. the cancerous tumour may be immunogenic). For example, the cancer cells may be capable of eliciting a systemic immune response in the cancer patient against one or more antigens expressed by the cancer cells. The antigens that elicit the immune response may be tumour antigens or may be shared by normal cells. A patient with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine (40). In some instances, a diagnosis of a cancer in an individual may include identification of a particular cell type (e.g. a cancer cell) in a sample of a body fluid or tissue obtained from the individual.

A patient, subject, or individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. a marmoset or baboon), an ape (e.g. a gorilla, chimpanzee, orang-utan or gibbon), or a human.

In some preferred embodiments, the patient, subject, or individual is a human. In other preferred embodiments, non-human mammals, especially mammals that are conventionally used as models for demonstrating therapeutic efficacy in humans (e.g. murine, primate, porcine, canine, or rabbit) may be employed.

In some embodiments, the patient, subject, or individual may have minimal residual disease (MRD) after an initial cancer treatment.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, a patient, subject, or individual susceptible to or at risk of the occurrence or re-occurrence of cancer may be treated as described herein. Such treatment may prevent or delay the occurrence or re-occurrence of cancer in the patient, subject, or individual.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens. Reducing immune suppression in cancerous tumors in an individual may improve the capacity of the individual to resist cancer growth, in particular growth of a cancer already present the subject and/or decrease the propensity for cancer growth in the individual.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

As used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above Methods Isolation of Lymphocytes from Human Skin by Three-Dimensional Explant Culture A three-dimensional skin explant protocol was established, as described elsewhere (29). The 9 mm×9 mm×1.5 mm Cellfoam Matrices (Cytomatrix Pty Ltd, Victoria, Australia) were autoclaved, then incubated in a solution of 100 mg/ml rat tail collagen I (BD Biosciences) in PBS for 30 minutes at room temperature, followed by one rinse in PBS. Samples of adult human skin were obtained within 3-6 hours of cutaneous surgery. Subcutaneous fat was removed and the remaining skin tissue was minced into fragments measuring approximately 1 mm×1 mm. Approximately five skin fragments/explants were placed and pressed down onto the surface of each matrix. Each matrix was placed into a separate well of a 24-well plate (Corning) containing 2 ml of 'Skin-T' media (Iscove's Modified Dulbecco's Medium (IMDM; Life Technologies) with 10% heat-inactivated foetal bovine serum (Life Technologies), L-glutamine (292 µg/ml; Life Technologies), penicillin (100 units/ml; Life Technologies), streptomycin (100 µg/ml; Life Technologies), N-2-hydroxyethylpiperazine-N-2-ethane sulfonic acid (HEPES; 0.01 M; Life Technologies), sodium pyruvate (1 mM; Life Technologies), minimal essential media (MEM) non-essential amino acids (1×; Life Technologies) and 3.5 µl/L 2-mercaptoethanol (Life Technologies). For the first 7 days of culture Amphotericin (2.5 µg/ml; Life Technologies) was added to the media. Media were refreshed three times per week. For feeding, the upper 1 ml of media was aspirated from each well and replaced with fresh medium. IL-2 and IL-15 were added from the initiation of culture and on each media change until the isolation of lymphocytes at 21 days. Human recombinant IL-2 (Proleukin; Novartis Pharmaceutical UK Ltd) was added at 100 IU/ml. Human recombinant IL-15 (Biolegend) was added at 20 ng/ml. Up to 96 wells (four 24-well plates) were set up in culture for each donor.

To isolate the lymphocytes, the matrices were transferred to a 50 ml centrifuge tube (Corning) containing 10 ml Hanks Balanced Salt Solution (HBSS; Life Technologies) with 0.01 mM HEPES (up to 12 matrices/tube). The matrices were rinsed with the cell suspension using a 10 ml pipette, and the cell suspension passed through a 70-µm filter (BD Biosciences) into a fresh 50 ml centrifuge tube (Corning). The 'washing' of the matrices was repeated two further times. The media from the culture well was also aspirated and passed through a 70-µm filter (BD Biosciences) into fresh 50 ml centrifuge tube (Corning). The wells were washed two further times with 1 ml of 0.01 mM HEPES/HBSS and passed through a 70 µm filter (BD Biosciences). Cells were subsequently isolated by centrifugation (1600 rpm for 15 minutes). The pellet was re-suspended in 'Skin-T' media. The final cell pellet was re-suspended in 'Skin-T' media for subsequent flow cytometry analysis or functional studies. When cell counts were required, leukocytes were counted at this stage by either; (1) trypan blue stain (0.4%) (Life Technologies) and haemocytometer, or (2) CASY® Model TT cell counter and analyser (Roche).

To isolate the lymphocytes, the matrices were transferred to a 50 ml centrifuge tube (Corning) containing 10 ml Hanks Balanced Salt Solution (HBSS; Life Technologies) with 0.01 mM HEPES (up to 12 matrices/tube). The matrices were rinsed with the cell suspension using a 10 ml pipette, and the cell suspension passed through a 70-μm filter (BD Biosciences) into a fresh 50 ml centrifuge tube (Corning). The 'washing' of the matrices was repeated two further times. The media from the culture well was also aspirated and passed through a 70-μm filter (BD Biosciences) into fresh 50 ml centrifuge tube (Corning). The wells were washed two further times with 1 ml of 0.01 mM HEPES/HBSS and passed through a 70-μm filter (BD Biosciences). Cells were subsequently isolated by centrifugation (1600 rpm for 15 minutes). The pellet was re-suspended in 'Skin-T' media. The final cell pellet was re-suspended in 'Skin-T' media for subsequent flow cytometry analysis or functional studies. When cell counts were required, leukocytes were counted at this stage by either; (1) trypan blue stain (0.4%) (Life Technologies) and haemocytometer, or (2) CASY® Model TT cell counter and analyser (Roche).

Because primary gut samples were more prone to contamination, acquired biopsies were first washed in IMDM containing 10% FCS, penicillin 500 U/mL, streptomycin 500 μg/mL, gentamicin 100 μg/mL, Amphotericin B 12.5 μg/mL and Metronidazole 5 μg/mL twice before minced and placed on grids. Gut grid cultures were grown in Gut-T Media (IMDM, 10% FCS, penicillin 100 U/mL, streptomycin 100 μg/mL, gentamicin 20 μg/mL, Metronidazole 1 μg/mL. For the first week of growth we also used Amphotericin B 2.5 μg/mL, similar to the skin. The media contained IL-2 (1001 U/ml) and IL-15 (20 ng/ml) and was changed 3 times per week. Because the gut structure was more loose than skin, lymphocytes could be harvested after one week.

Expansion of Tissue γδ T Cells

For expansion of human skin derived γδ T cells, mixed lymphocytes harvested after 3 to 4 weeks of grid culture were washed in PBS, spun down and re-suspended in Roswell Park Memorial Institute 1640 medium (RPMI-1640; Life Technologies) with 10% heat-inactivated foetal bovine serum (Life Technologies), L-glutamine (292 μg/ml; Life Technologies), penicillin (100 units/ml; Life Technologies), streptomycin (100 μg/ml; Life Technologies), N-2-hydroxyethylpiperazine-N-2-ethane sulfonic acid (HEPES; 0.01 M; Life Technologies), sodium pyruvate (1 mM; Life Technologies), minimal essential media (MEM) non-essential amino acids (1×; Life Technologies) and 10 μl/L 2-mercaptoethanol (Life Technologies)] at a density of $1\times10^6$/ml and supplemented with either IL-2 (1001 U/ml) alone or IL-2 plus IL-15 (20 ng/ml). Cells were seeded at $2\times10^5$/well into 96 well flat bottom plates (Corning) or at $2\times10^6$/well into 12 well plates (Corning) for expansion. Cells were monitored daily by microscopy, fed with fresh media and cytokines added 3 times a week. Upon full confluence and cell aggregates being visible, cells were split 1:1 into additional wells and plates, respectively. Cells were harvested and analysed using flow cytometry or used for functional assays after 7, 14 or 21 days depending on the assay. If pure γδ T cells were needed, cells were re-suspended in 1 ml FACS buffer (PBS containing 2% heat-inactivated foetal bovine serum and 0.01M EDTA) and stained for the αβ T cell receptor (Biolegend, clone IP26, 1:50) for 30 minutes in the dark on ice and all negative cells sorted using an Aria sorter running DIVA (BD Biosciences).

Co Culture with Fibroblasts

For every grid culture set up, we prepared two petri dishes (100×25 mm, Corning) that were scratched at several places using a scalpel. Minced skin pieces were placed on scratches. After 5 to 10 minutes drying in the air, the skin pieces normally stuck to the dish and 10 ml of Skin-T media was added. Media were changed once a week and primary fibroblasts were harvested following treatment with ACCUTASE® (Life Technologies) after 3 weeks of growth. Fibroblasts were seeded in either 48 well wells at $1\times10^4$ or into the bottom chamber of 24 well plates at $2\times10^4$ in the case of transwell experiments. After 2 to 3 days, fibroblasts reached confluence and co culture experiments were started using RPMI and the cytokines indicated adding $2\times10^5$ mixed skin lymphocytes in the case of 48 well plates, or $3\times10^5$ lymphocytes in the case of 24 well plates, bottom wells as well as transwells.

Flow Cytometry

Flow cytometry was performed using the following antibodies, coupled to the indicated fluorochromes: Ki-67-BV421, CD3-BV510, Vδ1-PeVio770, TIM-3-PE, CD9-PE, CCR3-BV421, CD39-BV421. All samples were also always stained for viability, using eFluor770NIR. Commercial antibodies were purchased from Biolegend or Miltenyi. Viability dye (near IR) was from eBioscience. Ki-67 staining was performed on cells fixed and permeabilised using the Foxp3 staining buffer set (eBioscience). Once each experiment was finished, the cell population was washed in PBS and split in half. Cells were stained with eFluor770 NIR for viability and washed, followed by TrueStain (Biolegend) to avoid unspecific binding of staining antibodies. Half of the sample was stained for the indicated surface markers, whilst the other half was stained for lineage markers only (CD3, Vδ1) and with the equivalent Isotype control for the surface markers used. This means that the matched mouse isotype Antibody conjugated to the same fluorochrome was used at the same concentration. Isotype controls bind to no known human antigen and therefor indicate unspecific binding or false positives. This is also known as truly negative. Each histogram (dark) is shown in comparison to its corresponding isotype control (open, dashed lines). Data summaries indicate the percentage of cells that stained positive for the indicated marker compared and thus at a level higher than the isotype. Flow cytometry data analysis was performed on FlowJo (Version 10.1).

RNA Sequencing

Vδ1 T cells from human skin and human blood Vδ1 T cells (after T cell receptor initiated expansion) were sorted (FACS), centrifuged and the cell pellet re-suspended in RLT buffer. RNA was prepared using the RNA-Micro-plus kit (QIAGEN). RNA libraries were generated using the KAPA Stranded RNA-seq Kit with RiboErase (HMR) (KAPA BIOSYSTEMS). Paired-end sequencing on HiSeq 2500 (illumina) using rapid run chemistry (read length: 100 bp). 101 base-pair paired-end reads were aligned and quantified using RSEM (v1.2.11) with Bowtie2. Reads were aligned to the human transcriptome, the count values have been log 2 transformed and quantile normalised.

Cytokine Quantification

Vδ1 T cells from human skin were stimulated with PMA and Ionomycin or plate bound anti-CD3 mAb (OKT3, 5 μg/ml) for 24 hours. Supernatants were taken afterwards and analysed using ProcartaPlex Human Cytokine & Chemokine Panel 1 A (34 plex) from eBioscience. Assays were analysed using a Luminex FlexMap3D (Luminex Corp). Data was analysed in Microsoft Excel, the mean of 3 donors (run in duplicates) is shown. Error bars indicate standard deviation.

Expansion of Blood Derived γδ T Cells

Blood derived γδ T cells within PBMCs can only be expanded if stimulated with TCR ligands (in the case of Vδ2, e.g. IPP, HMBPP, bisphosphonates) (41, 42) or antibody supplementation to either cross-link the TCR receptor (mAbs) or the TCR associated kinase CD3 (43). The same effect of TCR cross-linking can also be achieved using, lectins such as PHA. In the absence of addition of such TCR stimulating agents, the γδ T cells in PBMCs survive for several days but fail to expand and remain in their initial composition of T cell subsets with minor variations.

Blood from healthy volunteers was used to isolate PBMCs by layering whole blood onto Ficoll followed by centrifugation at 400 g for 20 minutes to separate red blood cells, blood plasma and white lymohocytes/monocytes. White blood cells were carefully harvested through a stripett and washed four times in cold PBS. Cells were resuspended in RPMI-1640 medium (Life Technologies) with 10% heat-inactivated foetal bovine serum (Life Technologies), L-glutamine (292 μg/ml; Life Technologies), penicillin (100 units/ml; Life Technologies), streptomycin (100 μg/ml; Life Technologies), N-2-hydroxyethylpiperazine-N-2-ethane sulfonic acid (HEPES; 0.01 M; Life Technologies), sodium pyruvate (1 mM; Life Technologies), minimal essential media (MEM) non-essential amino acids (1×; Life Technologies) at a density of $1×10^6$/ml and supplemented with IL-2 (1001 U/ml). Cells were transferred into a 24 well plate that was coated with pan γδ TCR monoclonal antibody (20 μg/ml, clone B1, Biolegend) 90 minutes prior to cell transfer. Cells were grown for 14 days, media changed ever 2-3 days and fresh cytokines added. Upon reaching confluence, cells were split 1:1. Under these conditions, after 14 days, the original minor population of γδ T cells is normally highly activated through their TCR (as indicated by upregulation if CD69 and CD25) and largely enriched consisting of mainly Vδ2 T cells but also Vδ1 T cells (up to 30% of all γδ T cells). Vδ1 T cells can subsequently be isolated using FACS for functional, phenotypic or genetic analysis.

Results

Figure 3A:
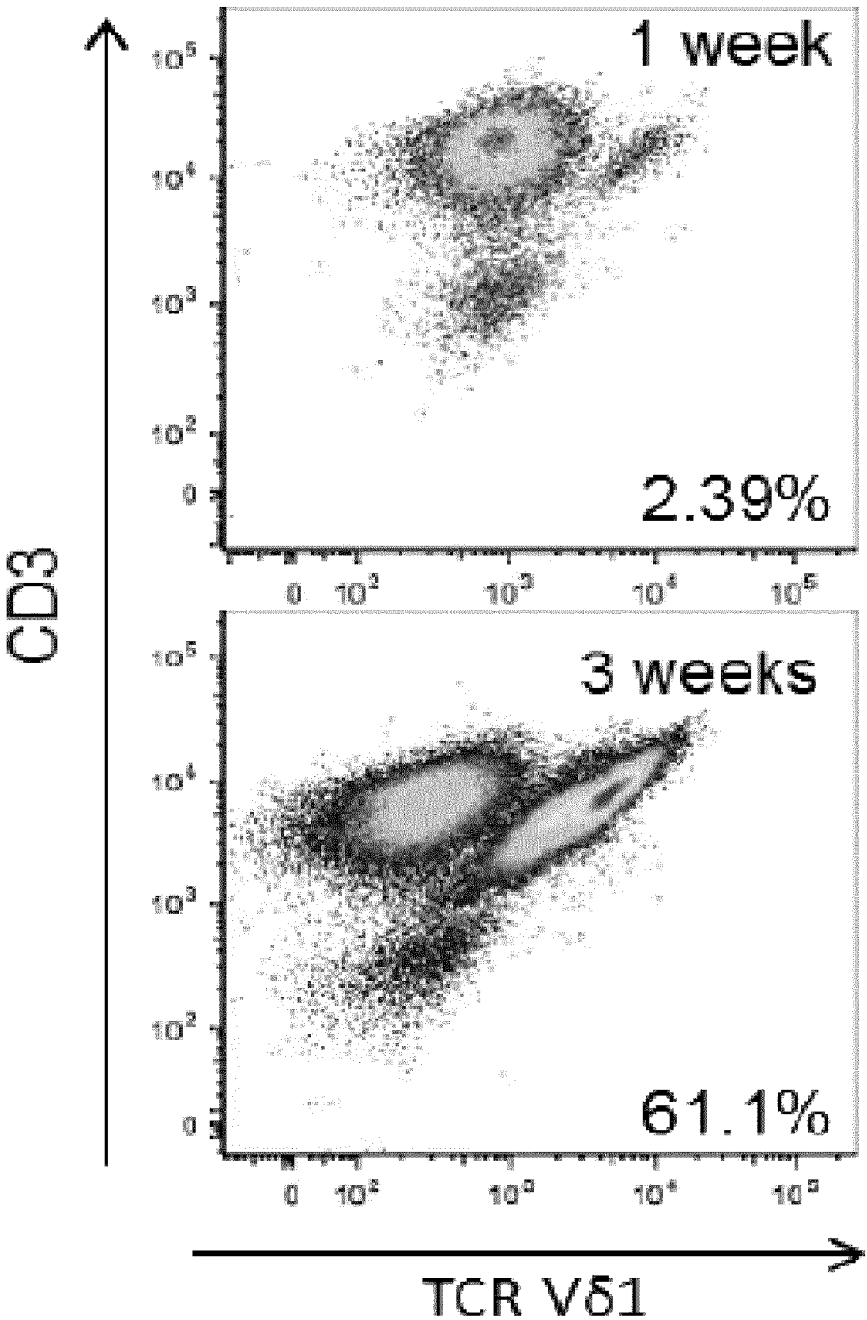
FIGS. 3A-3D show that skin-resident γδ T cells exclusively respond to segregation from the dermal stroma with strong activation and proliferation.
Figure 3A:
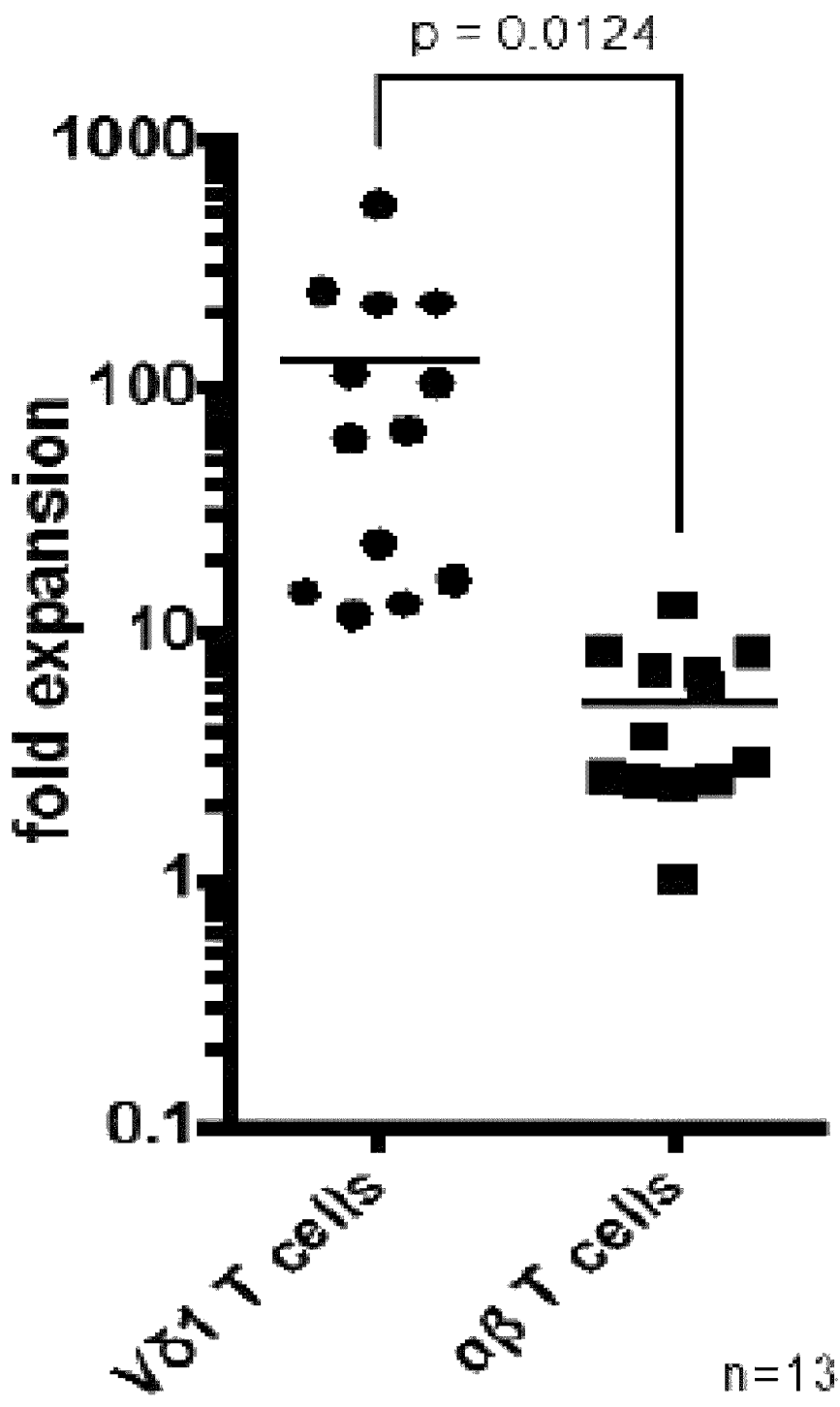
Figure 3B:
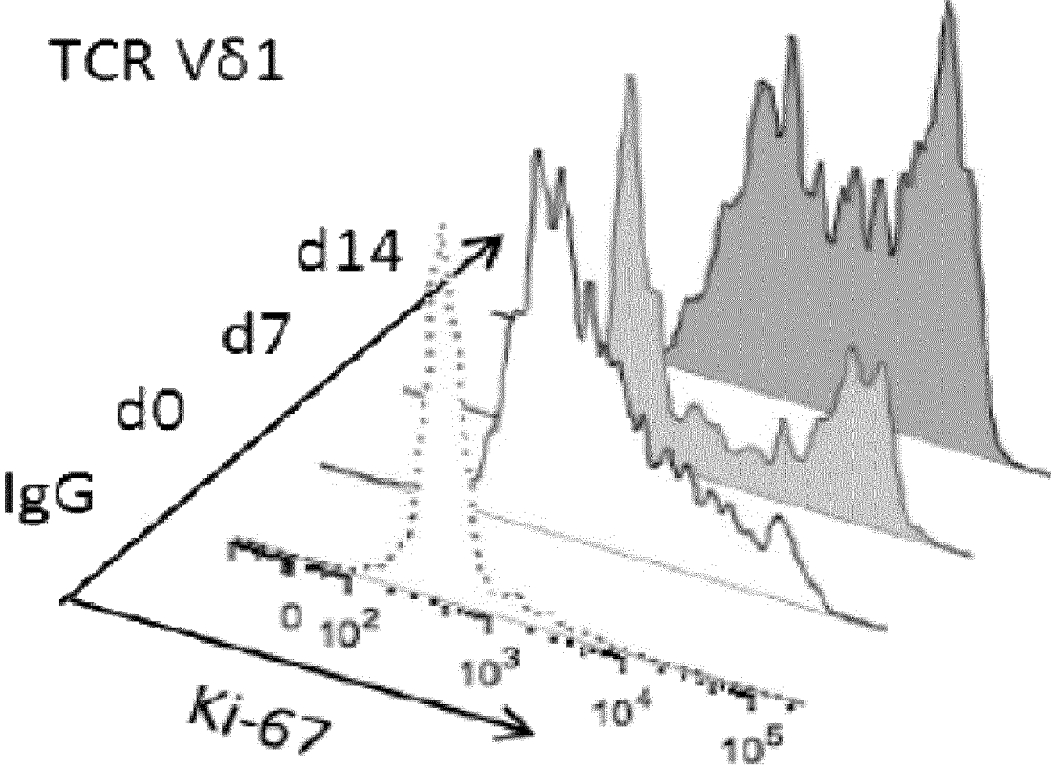
Figure 3B:
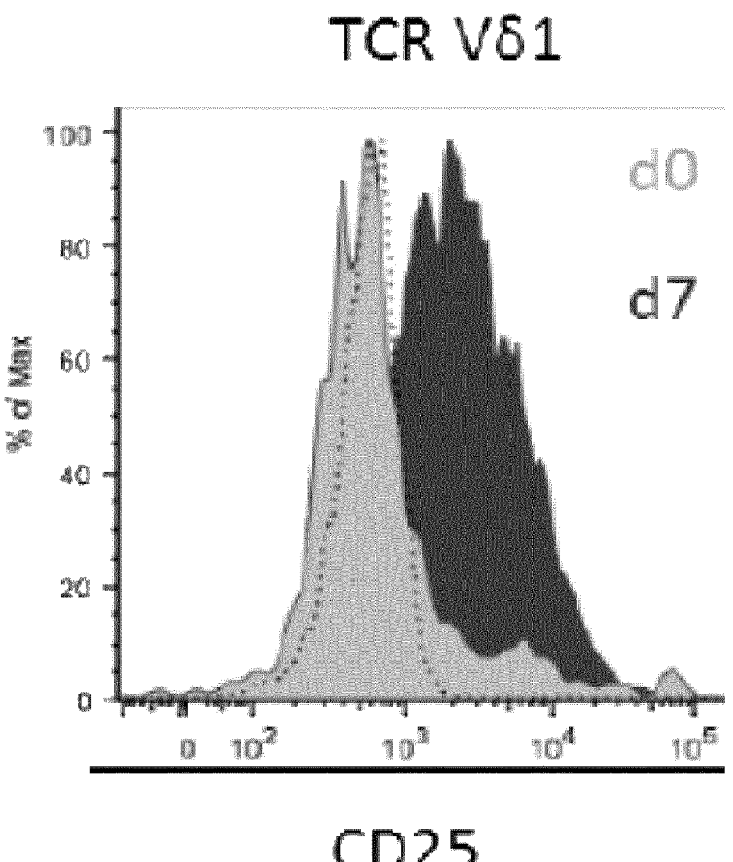
Figure 3C:
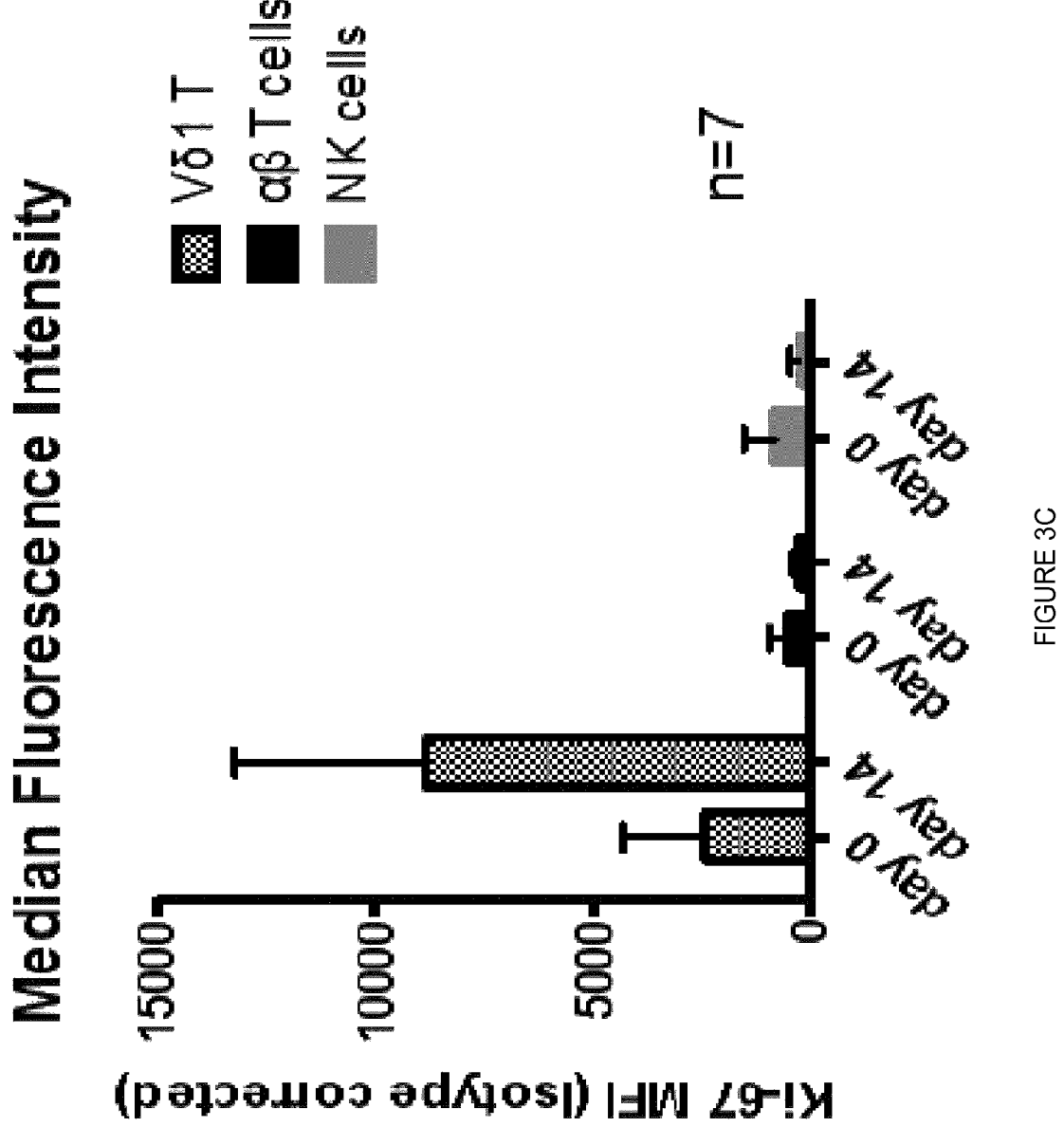
Figure 3D:
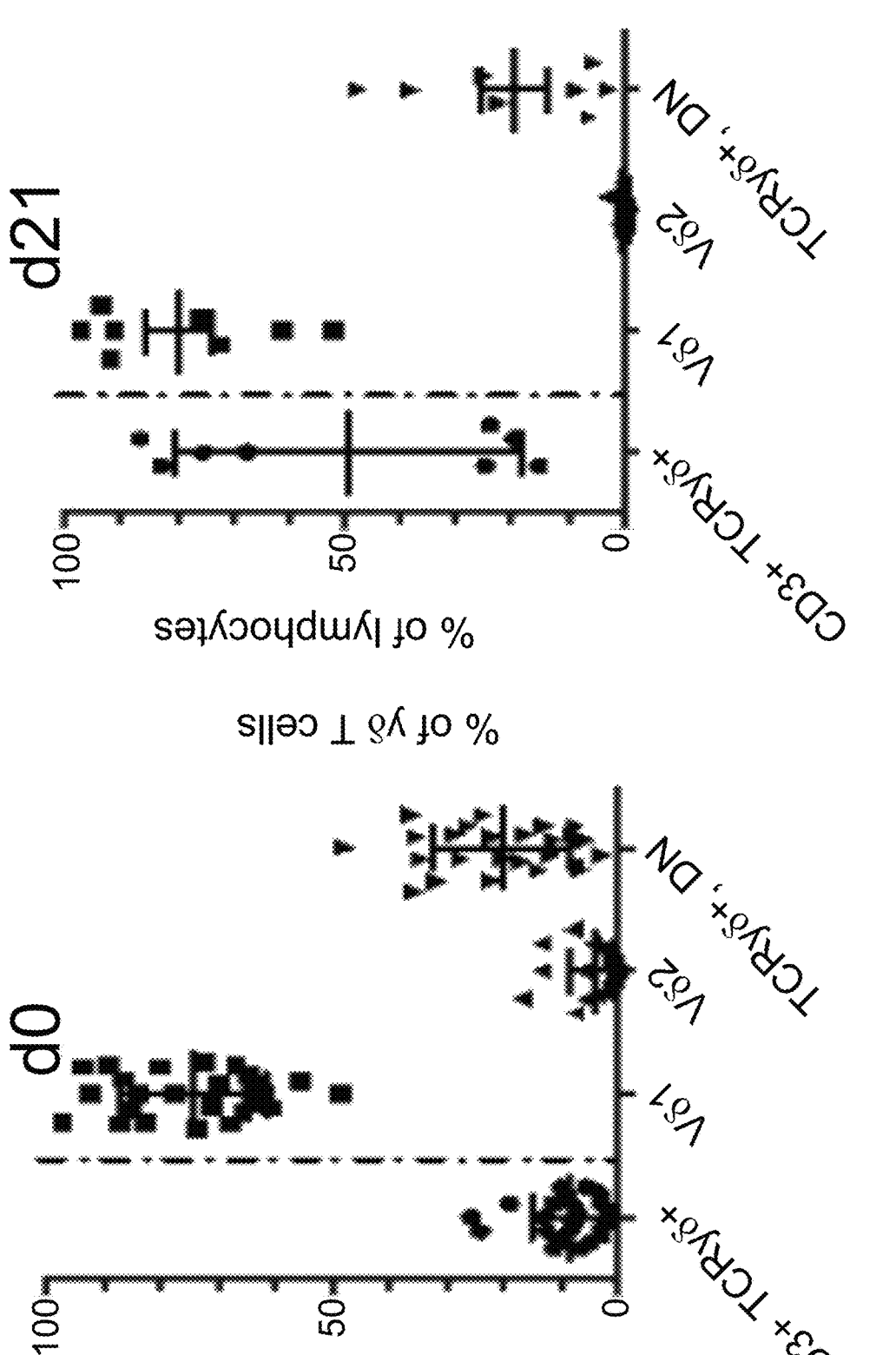
Figure 3D:

Human γδ T Cells are Abundant in the Skin, Express a Non-Vδ2 TCR and Participate in the Human Lymphoid Stress Surveillance Response Using the Clark protocol (29), we used human residual skin samples supplemented with IL-2 and IL-15 to enable the outgrowth of tissue resident lymphocytes over the course of 3 weeks gaining a lymphocyte population of an average of 240,000 cells per grid. Consistent with previous reports (29), we could identify distinct skin-resident lymphocyte subsets, with the majority of cells expressing a conventional αβ TCR, mostly of the tissue resident "TRM" type. Overall, 59.9% (±8.6) of CD45+ cells were CD4+, and 18.3% (±2.8) CD8+αβ T cells with an NK cell fraction of 8.7% (±3.6). Additionally, we found a substantial population of γδ T cells (mean 8.513% of CD45+ cells, 6.564%) in our donors (FIGS. 1A and 3D). This subset representation of lymphocytes after organotypic culture was highly reproducible in approximately 100 donors, and was comparable with freshly digested skin samples, differing only in a slightly increased γδ population, but of practical utility, offering much larger and purer lymphocyte populations compared to standard tissue digestion protocols. In accordance with the literature regarding tissue compartmentalisation of human γδ T cells based on their TCR delta chain, most human skin γδ T cells expressed a Vδ1 TCR chain paired with various γ chains identified by flow cytometry. This stands in contrast to the majority of peripheral blood γδ T cells, which show a single specific TCR heterodimer of a Vδ2 chain linked to Vγ9 and were virtually absent in human skin samples. However, it is important to note that a substantial subset expressed neither Vδ1 TCR nor Vδ2 TCR, evoking the moniker "Double Negative" γδ T cells (FIG. 1C).

Figure 2A:
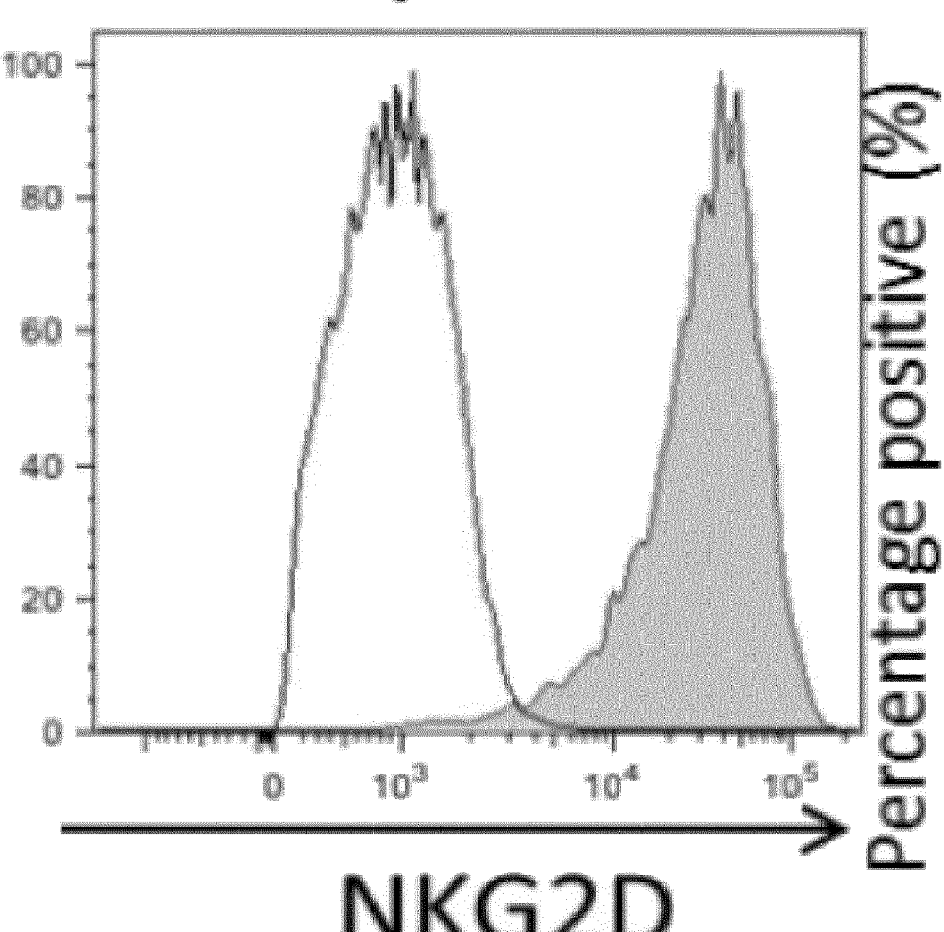
FIGS. 2A to 2D show that skin-resident γδ T cells derived directly from human skin via the Clark protocol display a so-called TH1-biased response upon activation by conventional means for activating T cells and likewise display a TH1-biased response upon activation by NKG2D ligands alone.
Figure 2A:
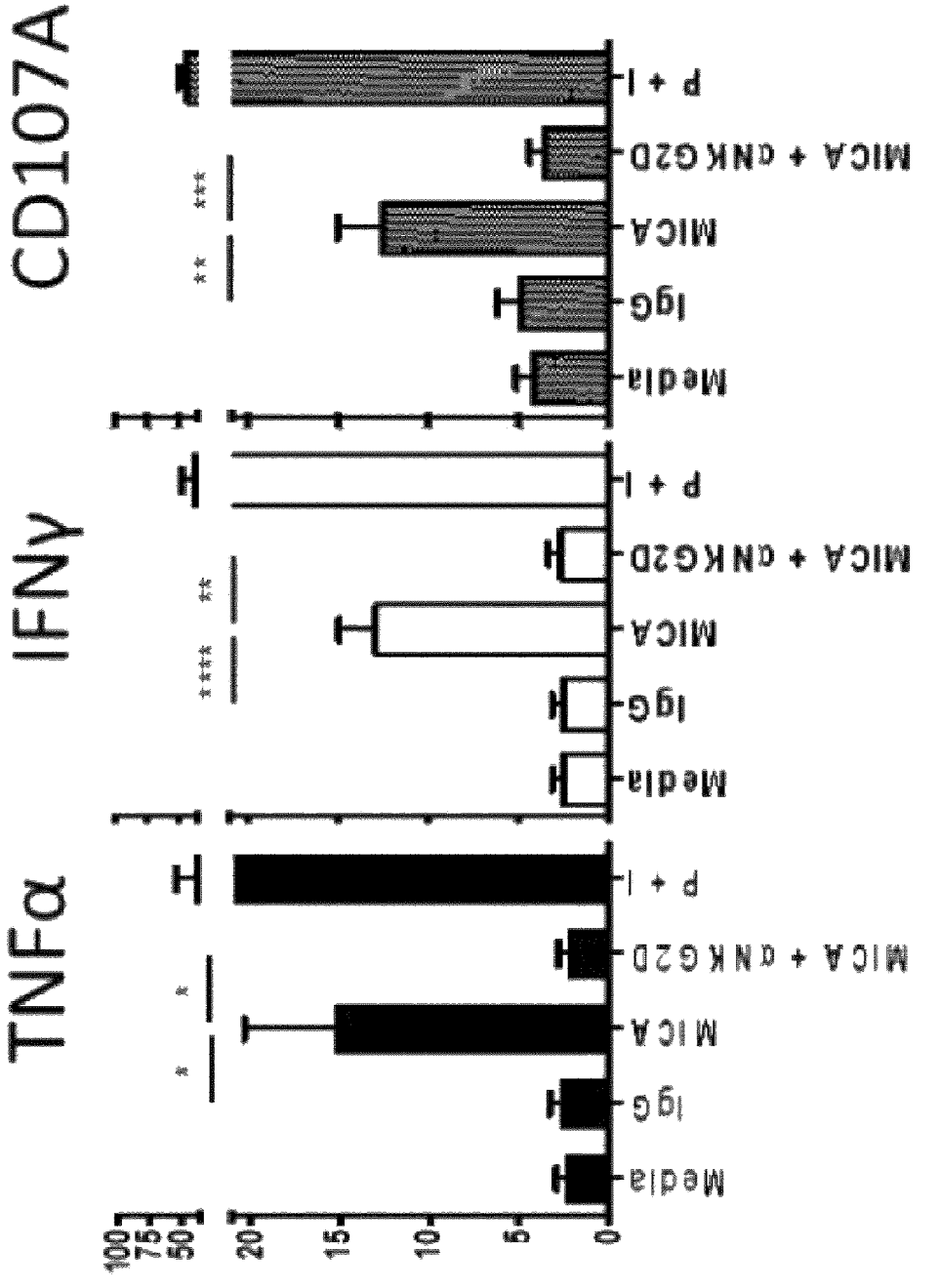
Figure 10A:
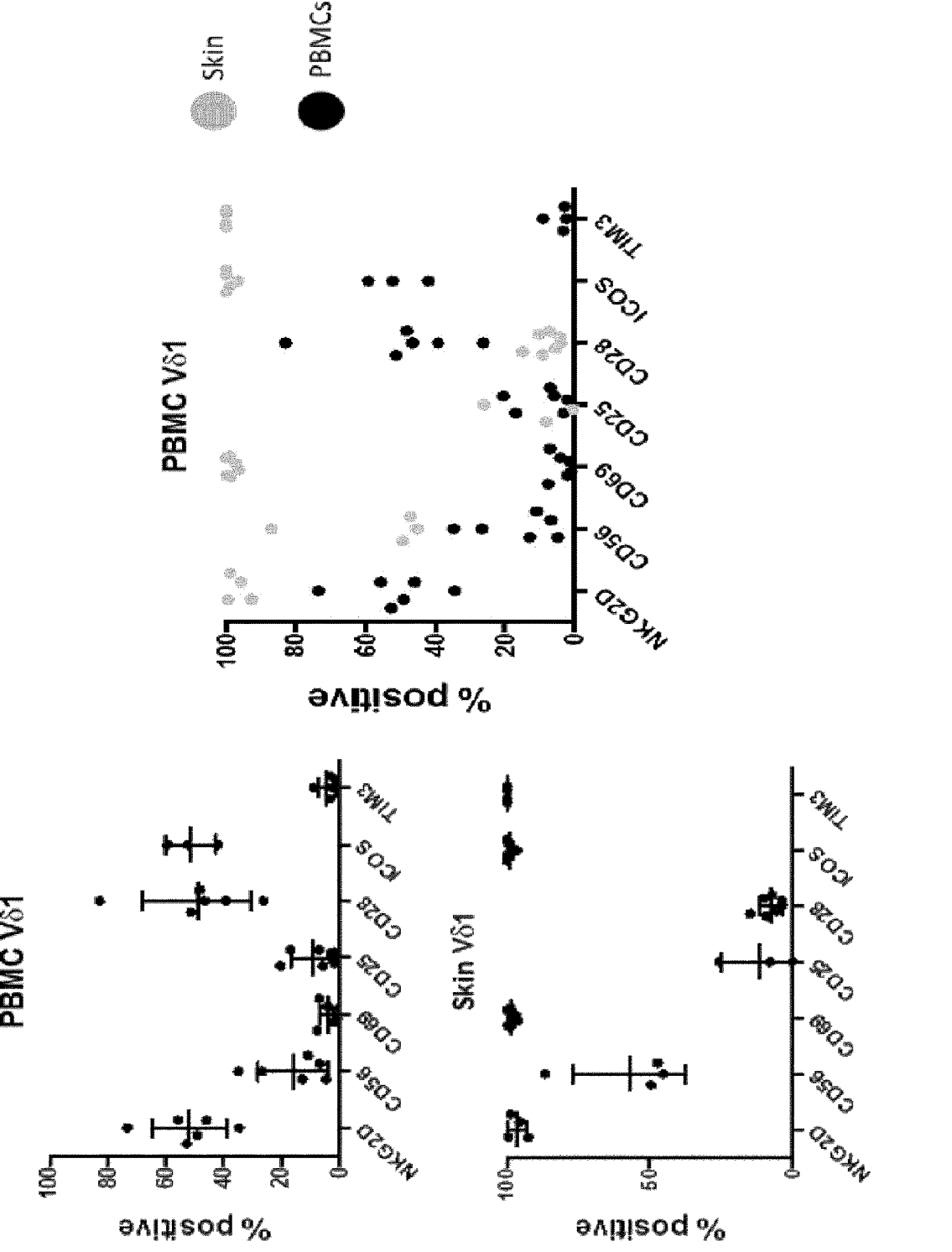
FIGS. 10A and 10B show that fresh, non-expanded skin-derived Vδ1 T cells show markers of prior T cell activation.
Figure 10B:
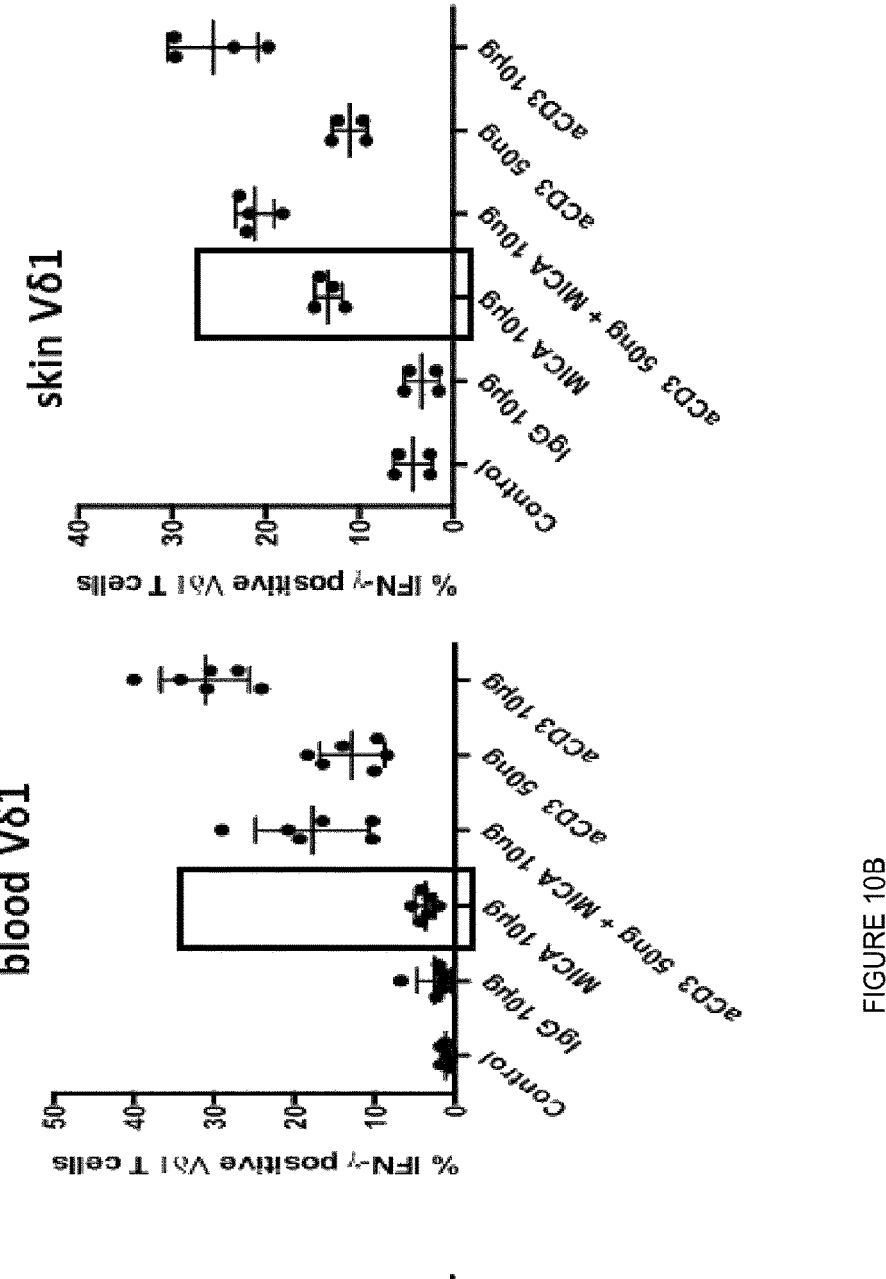

Skin-resident γδ T cells grown in this fashion showed a non-terminally differentiated memory phenotype lacking expression of CD45RA and expressing variable levels of the co-stimulatory molecule CCR7. By parallels with conventional systemic T cells, strong expression of the surface protein CD69 together with the expression of programmed death receptor 1 (PD-1); low to absent levels of IL-2 receptor a (CD25); and a lack of the co-stimulatory molecule CD28 draw the picture of previously activated or chronically activated T cells (FIG. 1D). Consistent with their tissue localisation, Vδ1 and DN cells show expression of skin and tissue homing markers, such as CLA, CCR4, CCR8 and integrin αE (CD103) (see FIG. 7). This tissue-homing marker-set might conceivably prove beneficial in an immunotherapy setting. Additionally, skin-resident γδ T cells show high levels of expression for the activatory receptor NKG2D (FIG. 2A), implying a possible role of these cells in the lymphoid stress surveillance response. NKG2D ligands, such as MICA, MICB and ULBPs, respectively, are up-regulated by cells in response to DNA damage, EGF-receptor activation and oxidative stress and may therefore allow T cells expressing NKG2D to identify and eradicate stressed or transformed cells, thereby maintaining tissue homeostasis. In line with this principle, we found that skin-resident γδ T cells expanded by the method of the invention are activated upon exposure to recombinant ligands for the NKG2D receptor (MICA, ULBP2) demonstrating degranulation as measured by the up-regulation of the lysosomal-associated membrane protein CD107a (FIG. 2A). This innate-like feature was exclusive to Vδ1+ and DN γδ T cells, as other tissue-resident T cells (FIG. 2C) and systemic γδ T cells lacked this response (FIG. 10B).

Figure 2B:
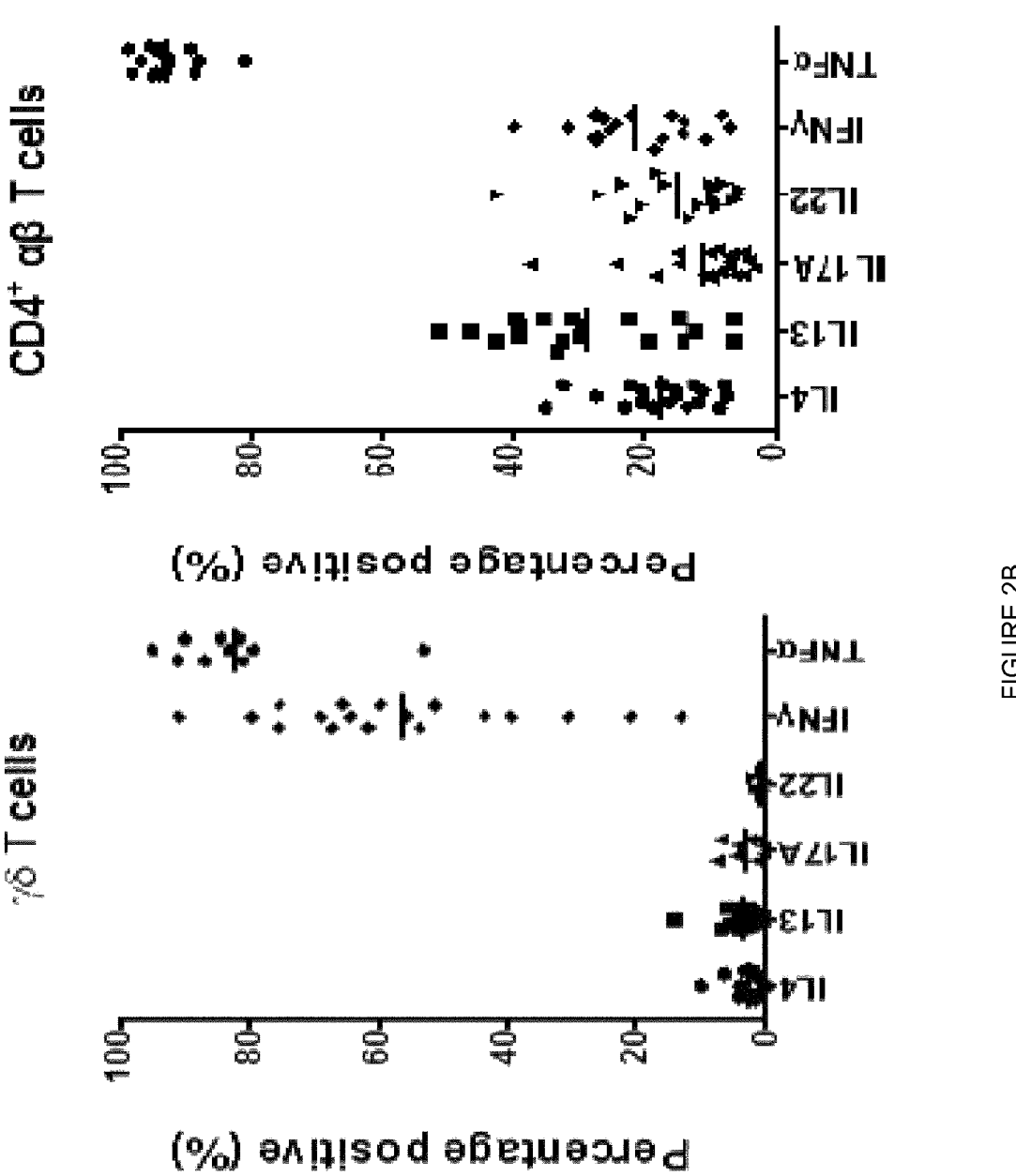
Figure 2C:
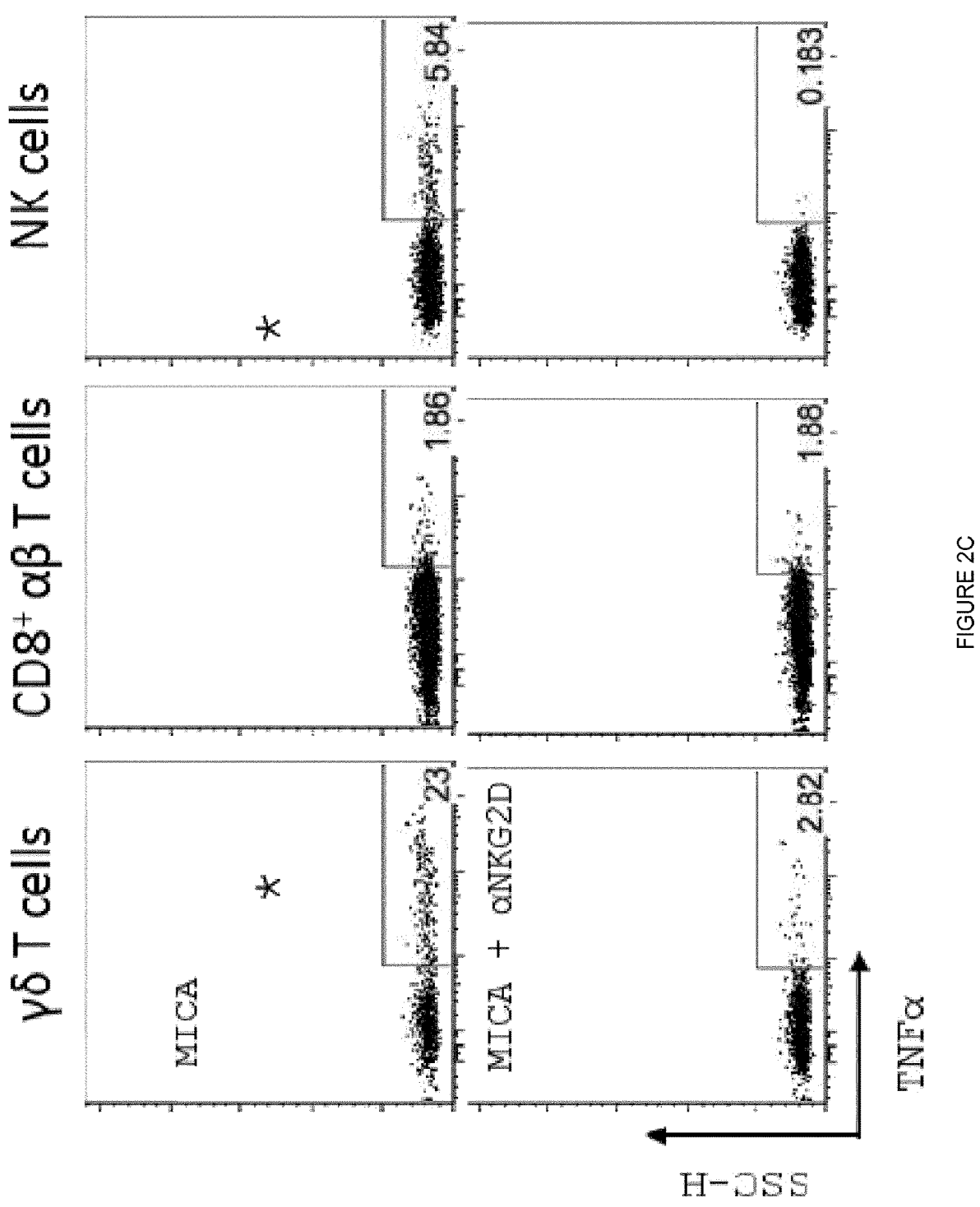
Figure 2D:
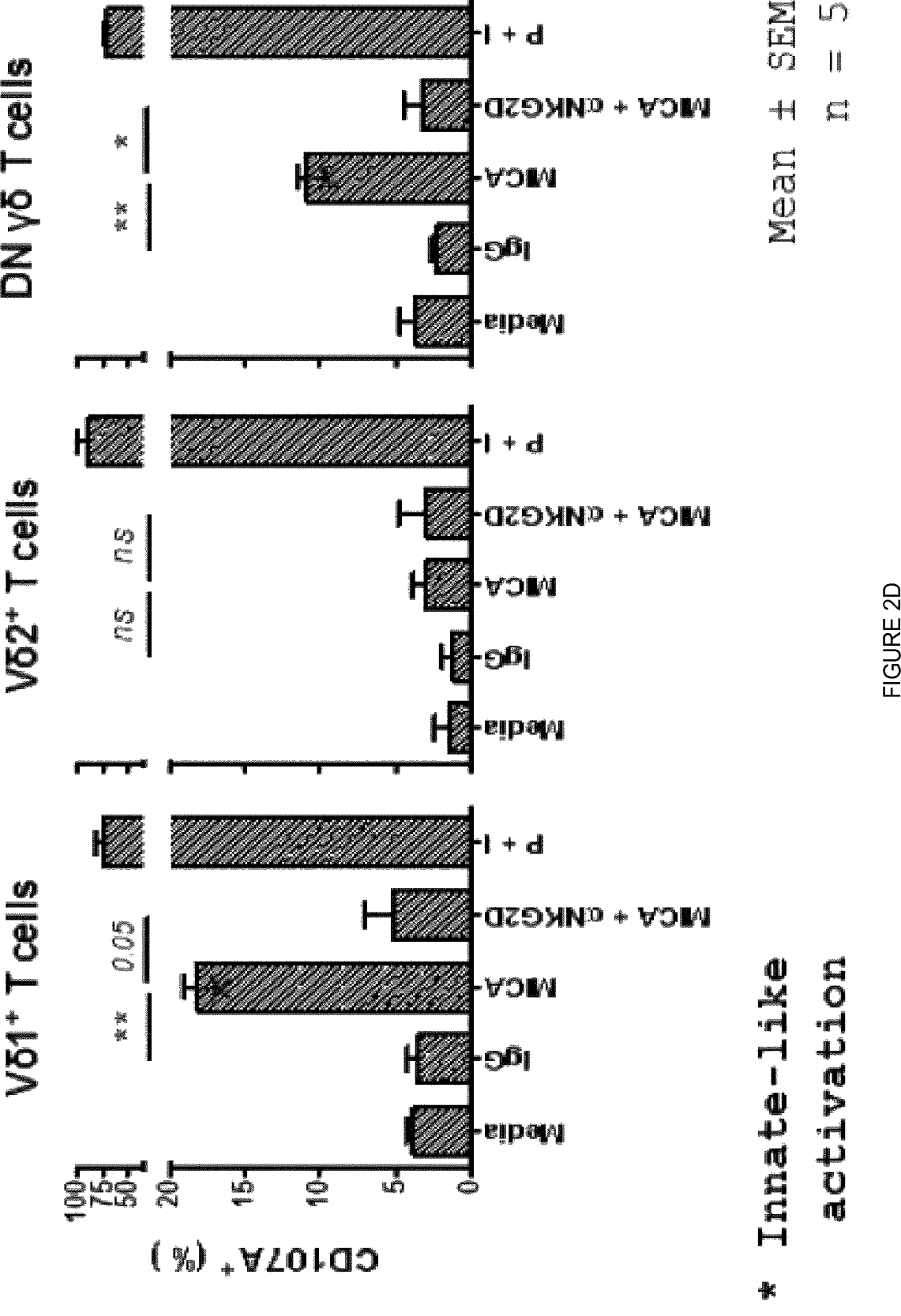
Figure 8:
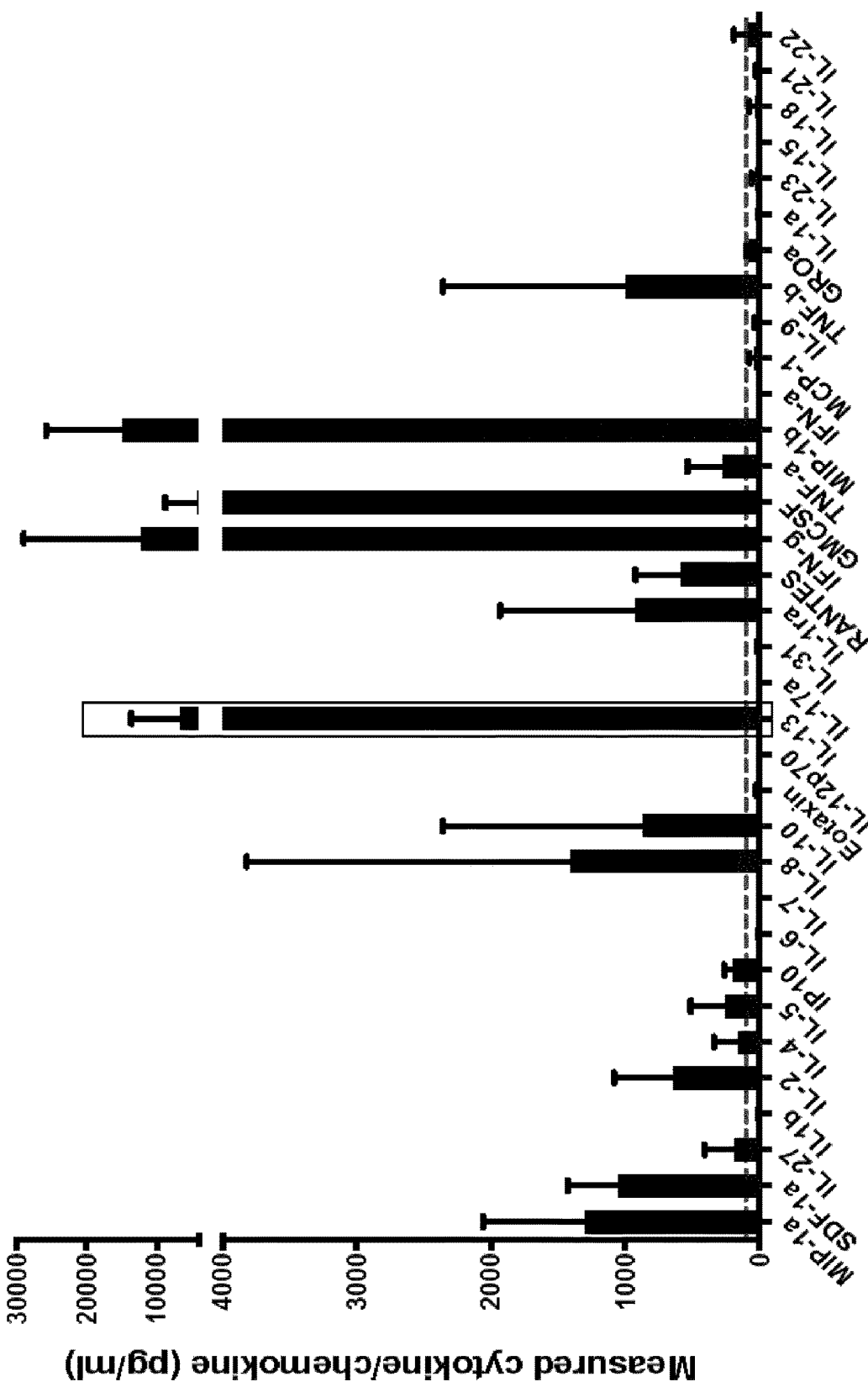
FIG. 8 shows that de-repression of skin-derived γδ T cells, without any stimulation of the TCR, results in spontaneous TH-1 cytokine production and interestingly and in contrast with fresh, TCR activated γδ T cells, in the production of the atopic cytokine IL-13. Consistently with freshly derived γδ T cells, de repressed and expanding γδ T cells produce negligible amounts of TH-2-associated cytokines, e.g. IL-4 and IL-5. Skin-derived γδ T cells were allowed to expand for 14 days and sorted negatively by excluding conventional αβ T cells. 150,000 mixed γδ T cells were cultured at a density of 1 million cells/ml in a 96 plate flat well in duplicates for 4 donors without any stimulation or cytokine supplementation. Supernatants were collected after 24 h and analysed using the LUMINEX®-based cytokine array by Affymetrix.

Overall, activated skin-resident Vδ1+ and DN γδ T cells executed a pro-inflammatory TH1 biased cytokine program (staining positive for IFN-γ, TNF-α and GM-CSF) when activated by either PMA/ionomycin or by NKG2D ligands, e.g. recombinant MICA protein (FIGS. 2A and 2B), thereby asserting the cells' innate-like responses. Indeed, the responses to MICA were almost completely abrogated by blocking the NKG2D receptor by means of an antibody (FIGS. 2B and 2C).

γδ T cells are known to secrete IL-17 under certain disease settings such as psoriasis and within some types of tumours. γδ T cells expanded by the method of the invention produce low level or no IL-17 even upon extensive activation (FIGS. 2B and 8). Conversely, tissue-resident CD4-expressing αβ T cells did produce IL-17 upon TCR activation (FIG. 2B). In general, αβ T cells showed a much more diverse cytokine repertoire in response to PMA/ionomycin compared to Vδ1+ and DN γδ T cells, which were limited to a TH1 biased programme associated with host-protection.

Figure 4A:
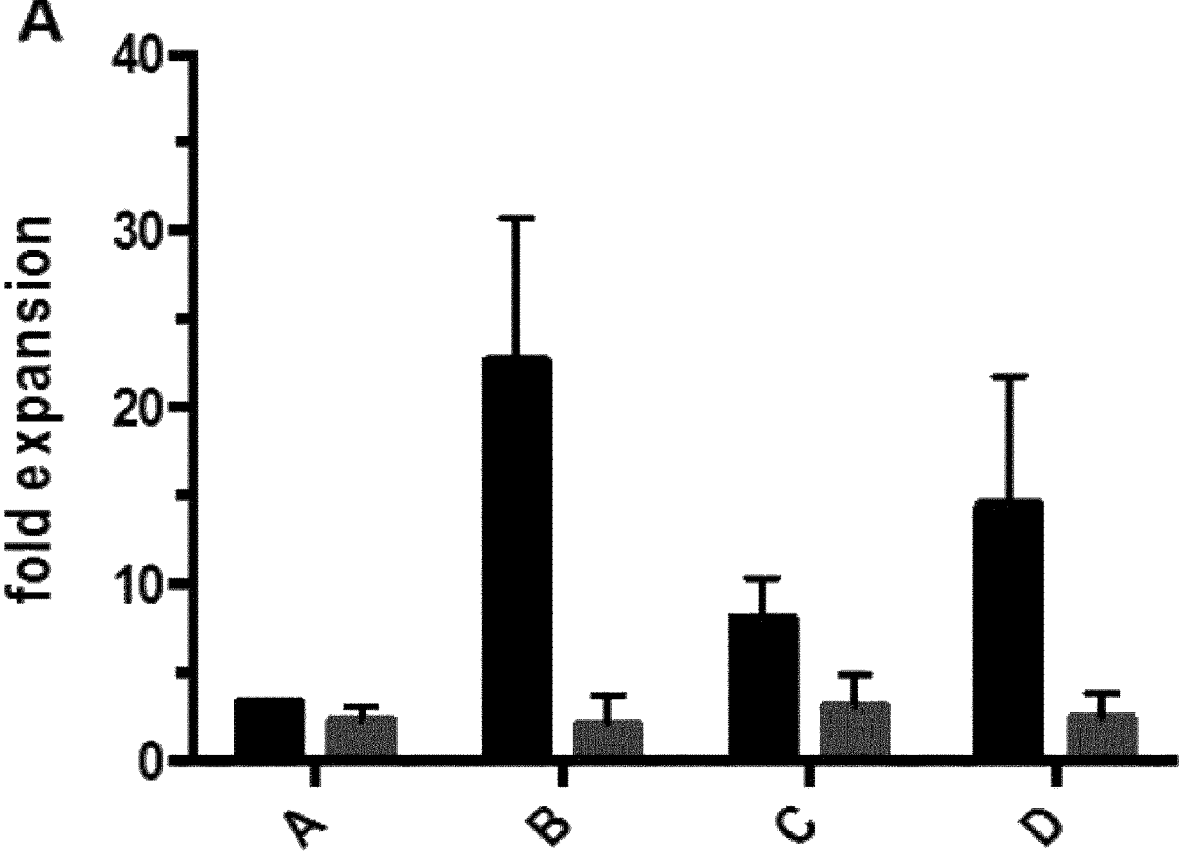
FIGS. 4A and 4B show that skin-resident γδ T cells respond to loss of tissue and are kept in check via a contact-dependent mechanism by dermal stroma cells, particularly fibroblasts.
Figure 4A:
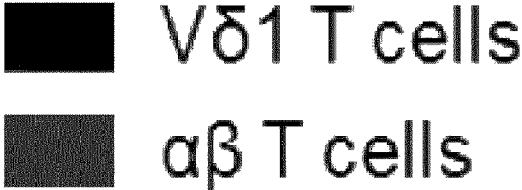
Figure 4A:
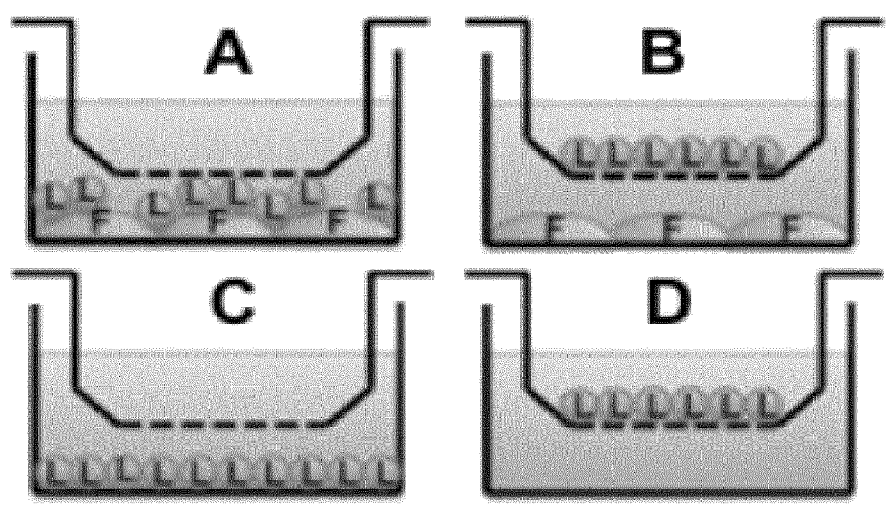
Figure 4B:
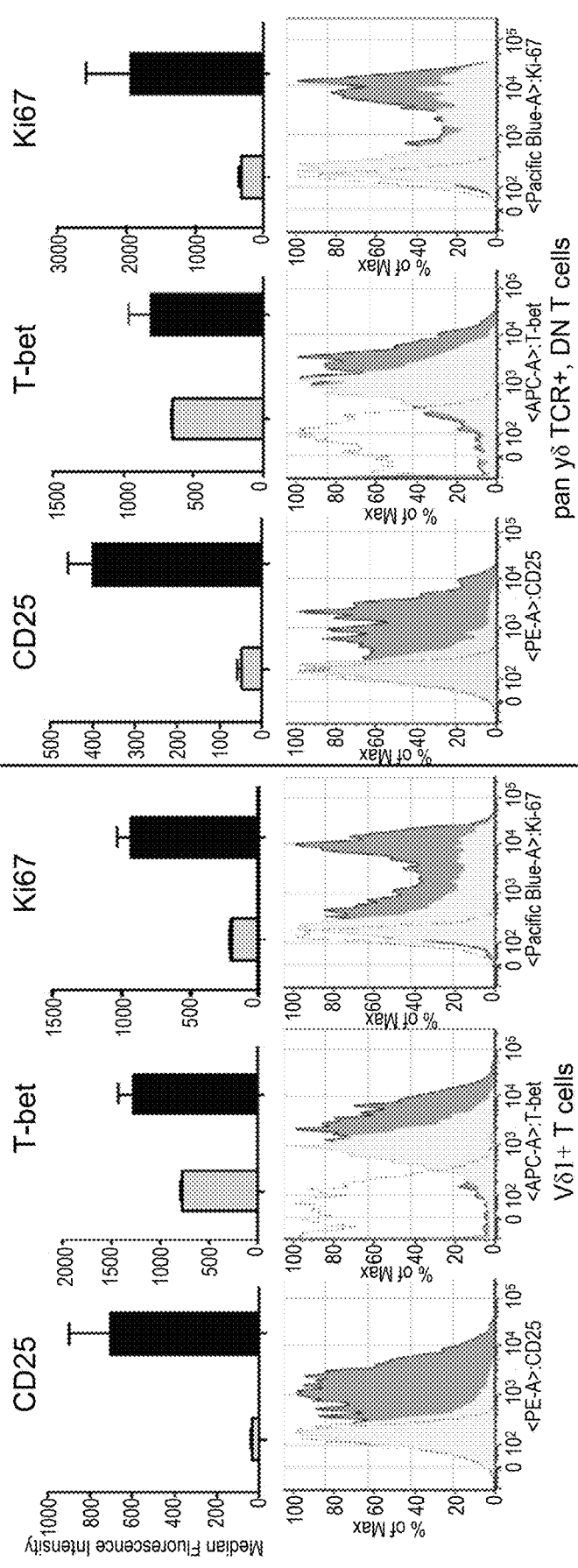

Separation from Tissue Causes Activation and Massive Proliferation of Human Tissue γδ T Cells In order to further study human tissue, γδ T cells and their biology, we transferred mixed skin lymphocytes into cell culture wells and supplemented them with IL-2 in order to maintain viability over time. Interestingly, we quickly found that by segregation away from stromal and epithelial cells present in the organotypic culture, Vδ1 T cells uniquely showed signs of activation and proliferation without any other added stimulus. Within fewer than 7 days, Vδ1+ and DN γδ T cells uniquely and massively up regulated the nuclear factor Ki-67 and increased surface expression of IL-2 receptor α (CD25) (FIGS. 3B and 4B). Strikingly, over the course of 3 weeks and solely in the presence of IL-2, tissue-derived Vδ1+ and DN γδ T cells outgrew all other T cell subsets, so as to represent up to 65% of all skin lymphocytes, increasing in number in average 127.18 fold, whilst αβ T cells only multiplied 5.21 times (p=0.0124) as measured by absolute cell numbers (FIG. 3A). MFI of the cell cycling-associated nuclear factor KI-67 increased from 2664.5(±1876.1) to 8457.7(±4574.2) in 14 days in Vδ1+ and DN γδ T cells, whereas in as T cells the MFI decreased from 592.8(±390.5) to 284.7(±140.1) over the same time course (FIG. 3C). This phenomenon of selective, skin-resident γδ T cell outgrowth could be further supported using additional recombinant IL-15, which increased the viability and total number of lymphocytes.

Skin γδ T Cells are Actively Suppressed by Fibroblasts in a Contact Dependent Manner The striking expansion of Vδ1+ and DN γδ T cells described in the preceding paragraph never occurred in organotypic culture systems in which there was extensive fibroblast outgrowth. We therefore grew out autologous fibroblasts in order to test directly whether their co-culture with Vδ1+ and DN γδ T cells would inhibit the T cells' expansion. After a 3-week grid culture, we seeded mixed skin lymphocytes into wells that were either empty or that contained a previously-established confluent monolayer of fibroblasts, and in each case supplemented the medium with exogenous IL-2, to sustain T cell growth. Additionally, we used transwells that prevented the T lymphocytes from directly contacting the fibroblasts within the same wells, but permitted them to be influenced by any soluble factors made by the fibroblasts. In 14 days of co-culture, with Vδ1+ and DN γδ T cells started proliferating in wells in which there were no fibroblasts and in those in which the T cells were prevented from directly contacting the fibroblasts. As before, αβ T cell proliferation was low under all conditions. Conspicuously, when T cells were permitted direct contact with fibroblasts, the growth rate over two weeks of Vδ1+ and DN γδ T cells was considerably reduced, from 22.6 (SEM 8.07) fold in wells without fibroblast contact to 3.3 (SEM 0.17) fold (FIG. 4A). This contact-mediated inhibition was further confirmed by the absence of up-regulation of CD25, Ki-67 and the transcription factor T-bet in Vδ1 over the course of 7 days as compared to the lymphocytes grown alone (FIG. 4B). Some form of tissue-mediated control of the immune system would appear to be fundamental to maintaining tissue homeostasis, since without this there would be the potential for persistent inflammation. The suppressive regulation of Vδ1+ and DN γδ T cells by stromal fibroblasts would seem to be an example of such control.

In sum, the phenotype of skin-resident Vδ1+ and DN γδ T cells and their striking functional potentials are reflective of pre-activated T cells that are ordinarily kept in check by their neighbouring dermal fibroblasts via a contact-dependent mechanism that is yet to be characterised. Inactivating that mechanism by releasing the T cells from contact with the fibroblasts selectively permits the striking expansion of Vδ1+ and DN γδ T cells, whereas other T cells in the skin are unaffected.

Figure 5A:
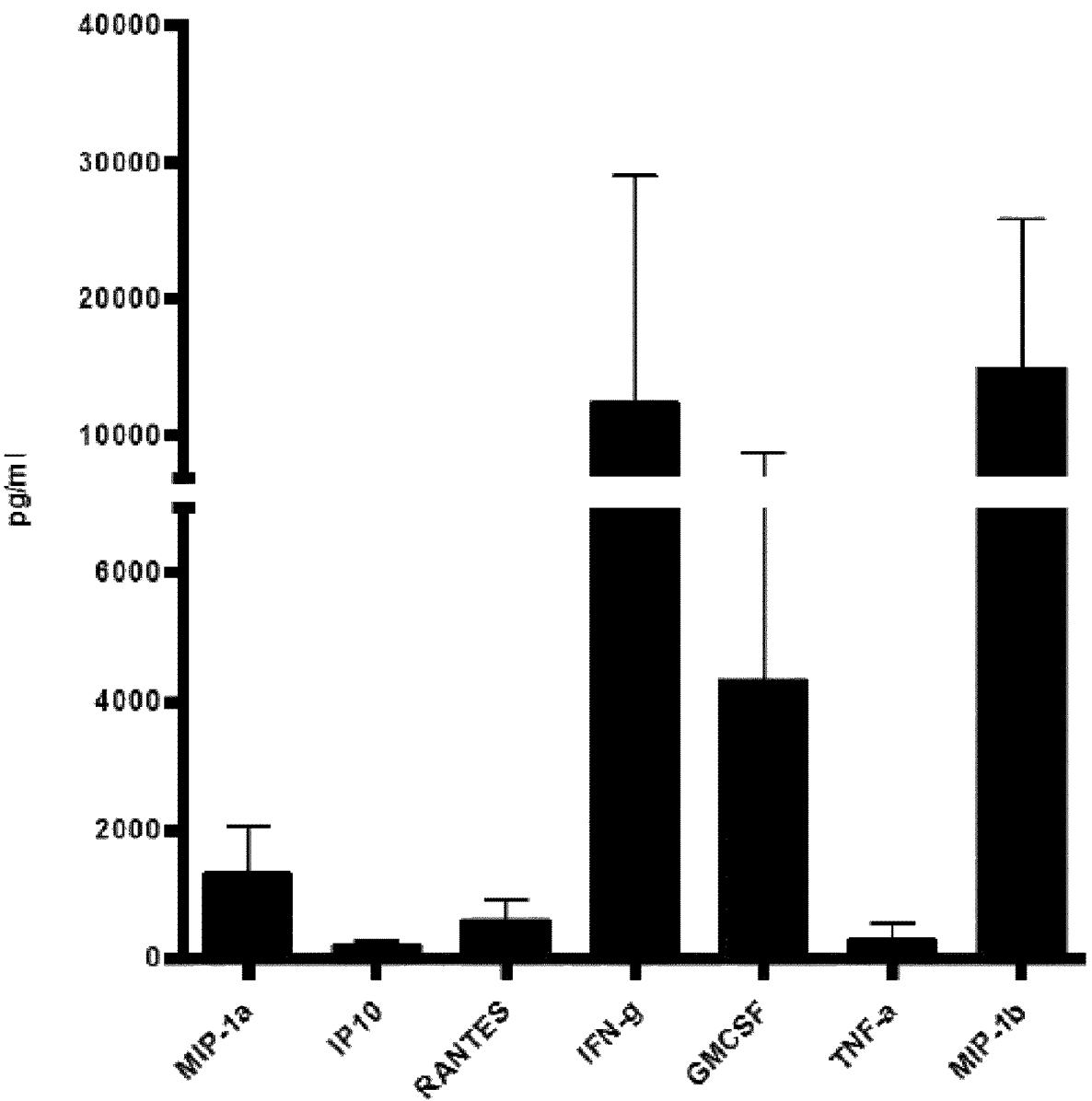
FIGS. 5A and 5B show that expanding skin γδ T cells display signs of de-repression and gain of strong cytotoxic potential.

Release of Contact Mediated Inhibition Prompts a Cytotoxic TH1 Biased Cytokine Response by Skin Vδ1 T Cells Mixed skin-derived lymphocytes were expanded for 14 days, and fluorescence associated cell sorting used to remove αβ T cells from γδ T cells that could thereby be obtained in purities of up to 90%. Those highly enriched cells were deposited into cell culture wells at concentrations of 150,000 cells/well in RPMI medium containing 10% FCS, whereafter the supernatants were collected 24 h later and assessed for a wide range of effector cytokines using a LUMINEX®-based array. Wholly unexpectedly, expanding γδ T cells (provoked only by their separation from fibroblasts) spontaneously produced large amounts of TH1 associated cytokines such as IFN-γ (12,383.46±16,618.90 μg/ml), GM-CSF (4,316.73±4,534.96 μg/ml) and the proinflammatory chemokines CCL4 (14,877.34±10,935.64 μg/ml) and CCL3 (1,303.07±757.23 μg/ml) (FIG. 5A).

Figure 5B:
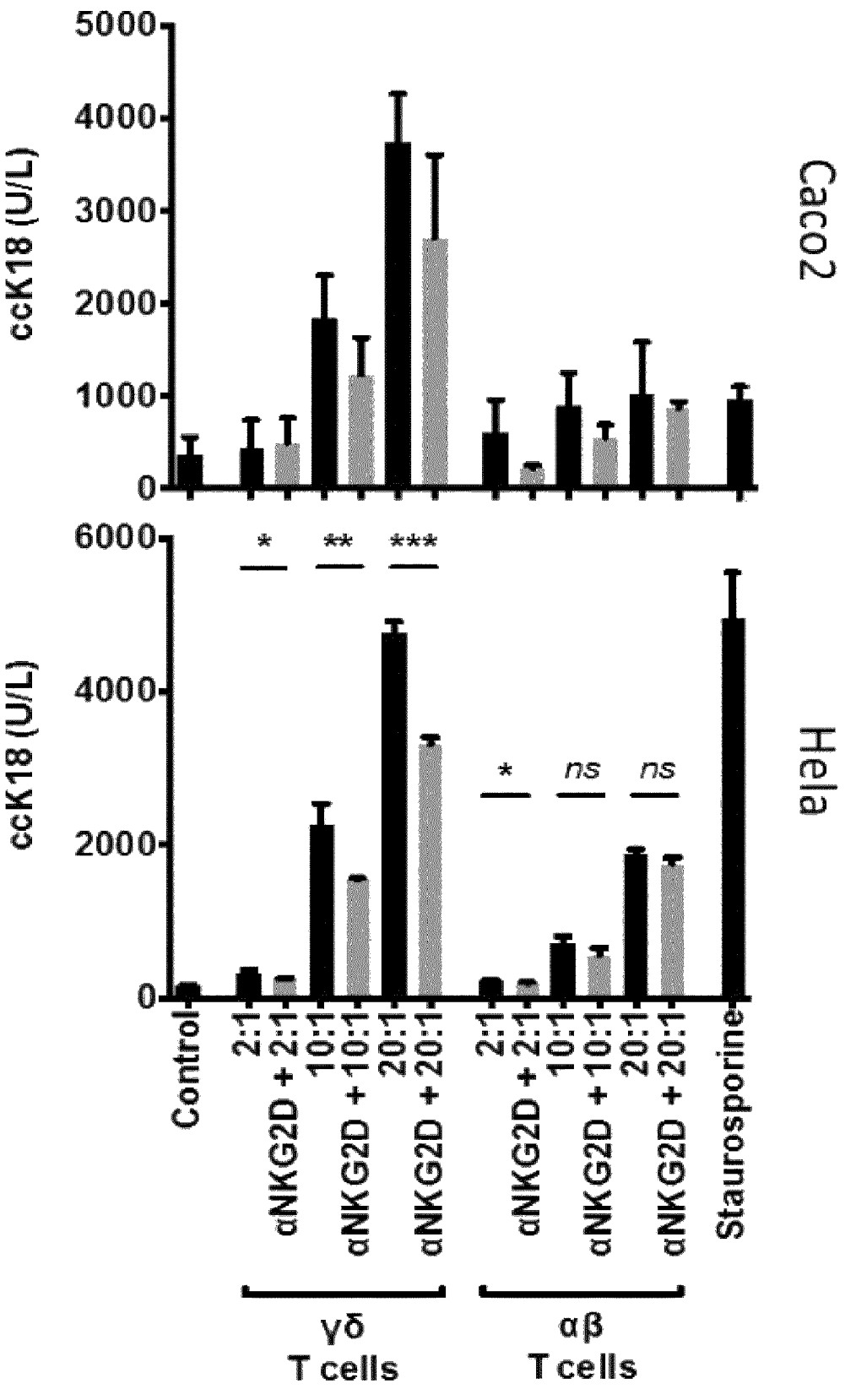
Figure 6A:
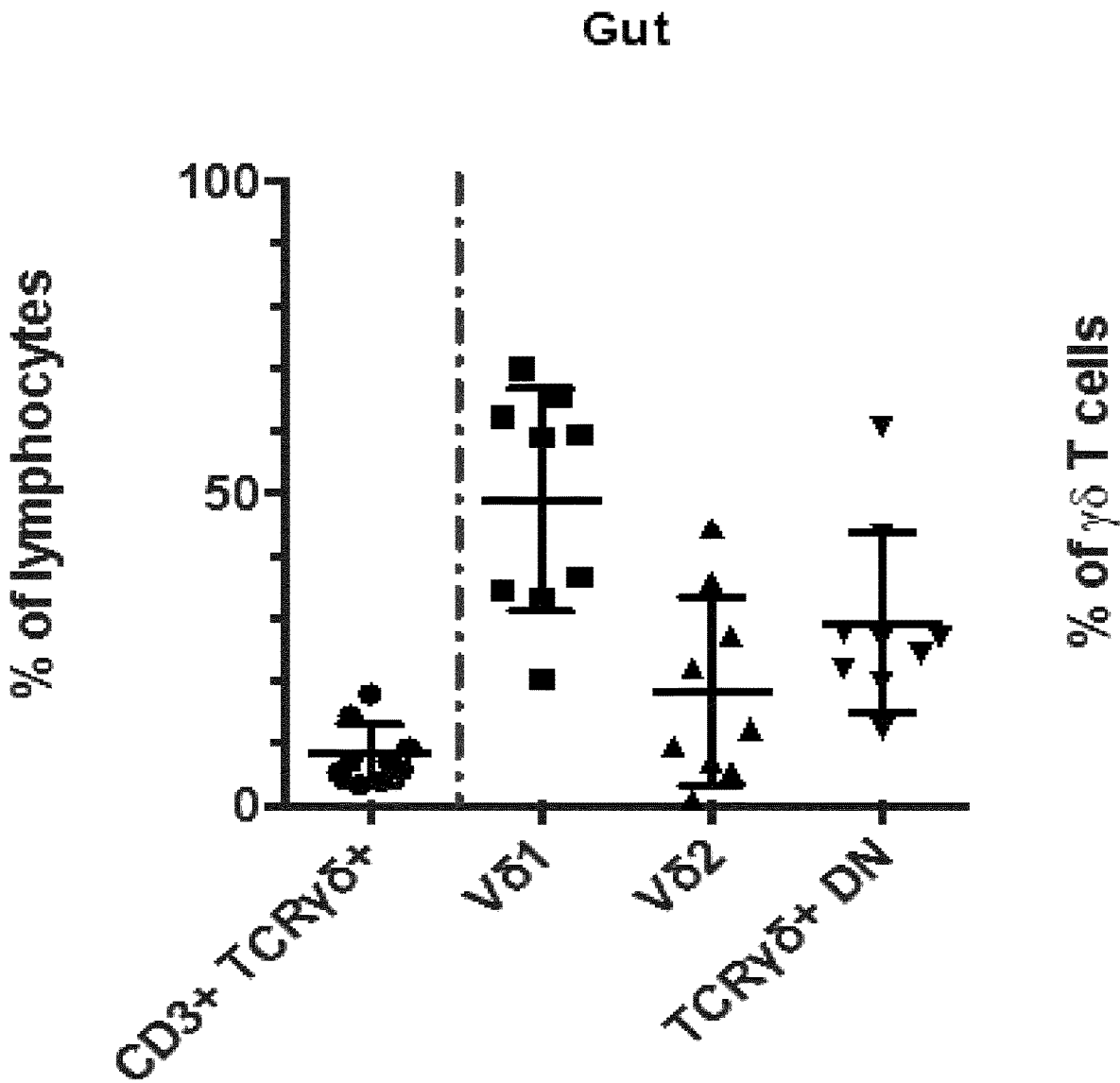
FIGS. 6A-6D show an analysis of tissue-resident γδ T cells in human gut.
Figure 6B:
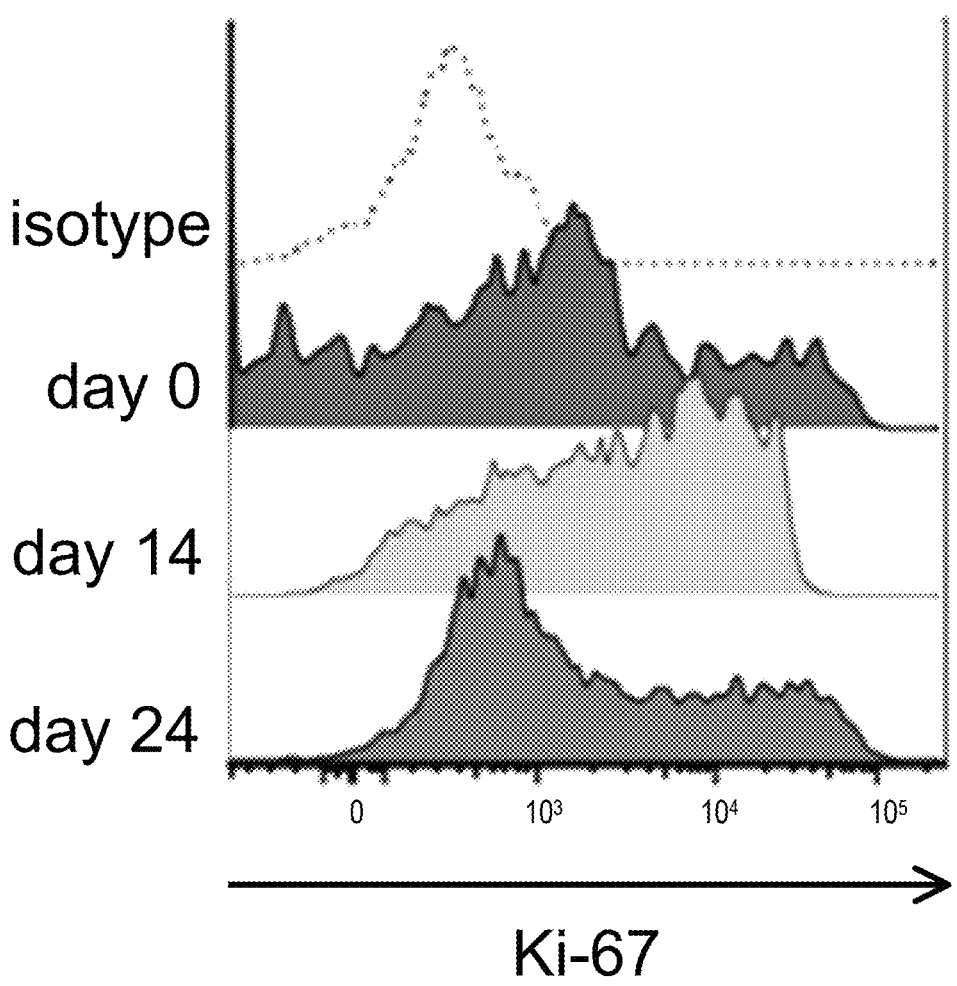
Figure 6C:
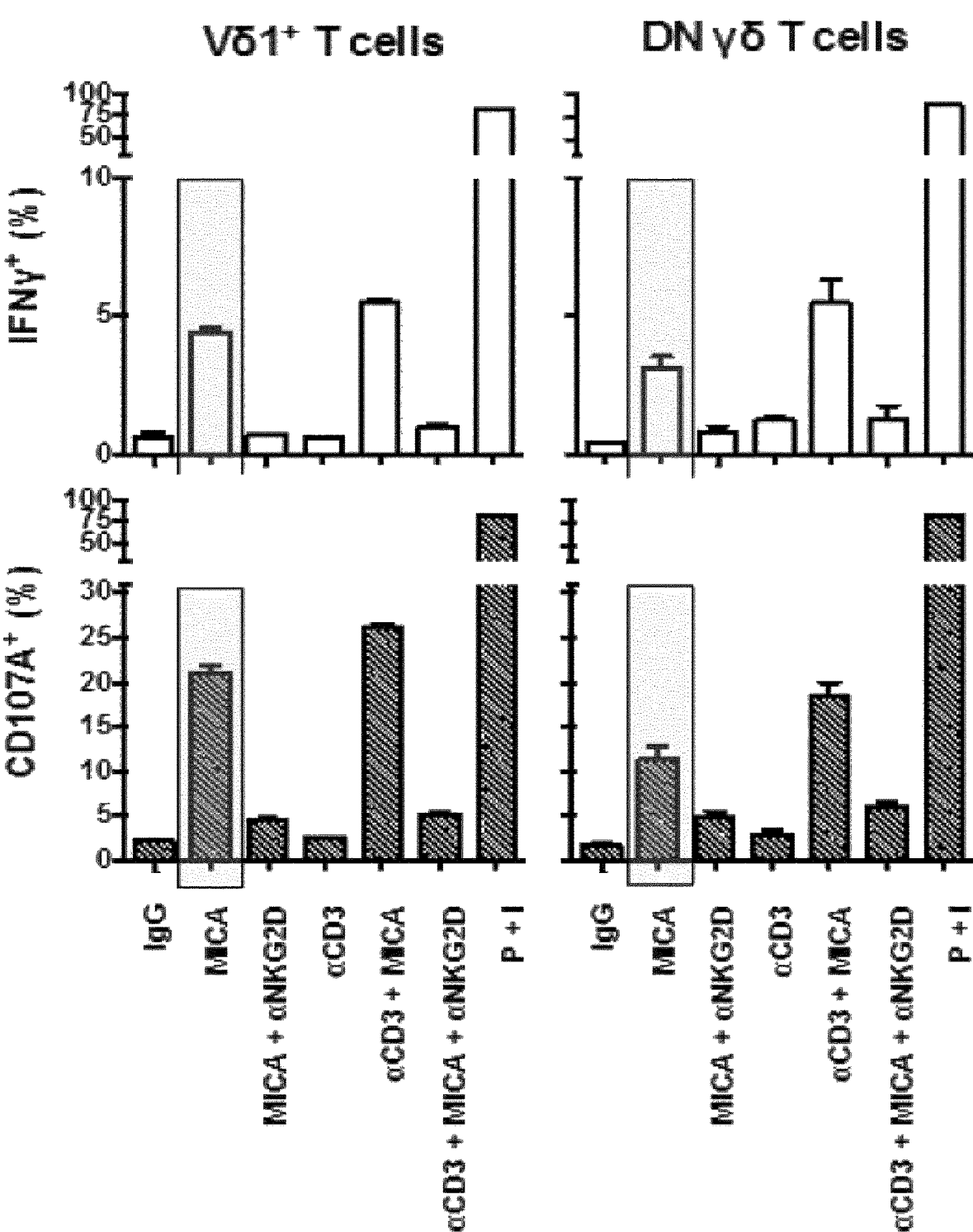
Figure 6D:
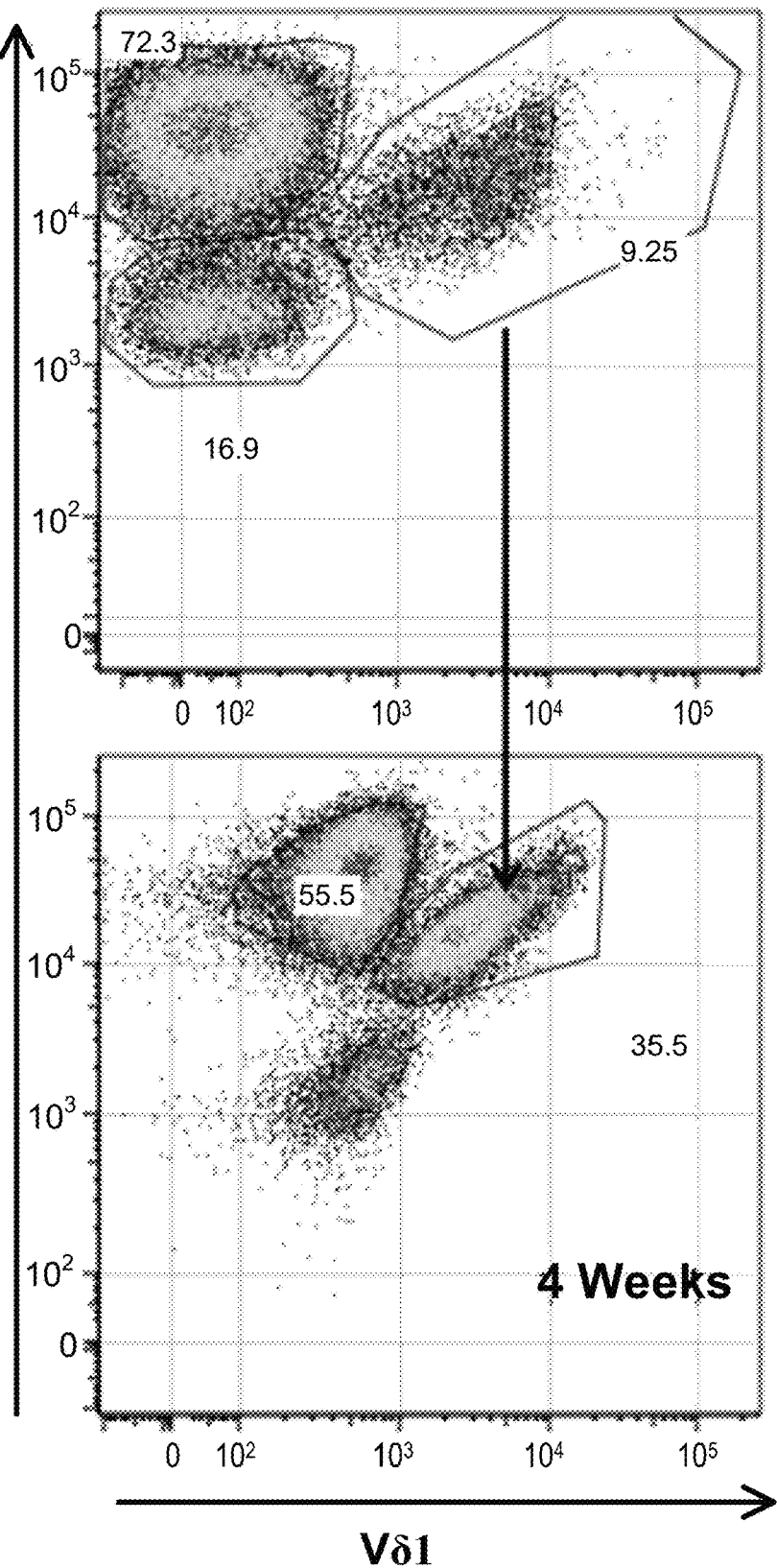
Figure 9A:
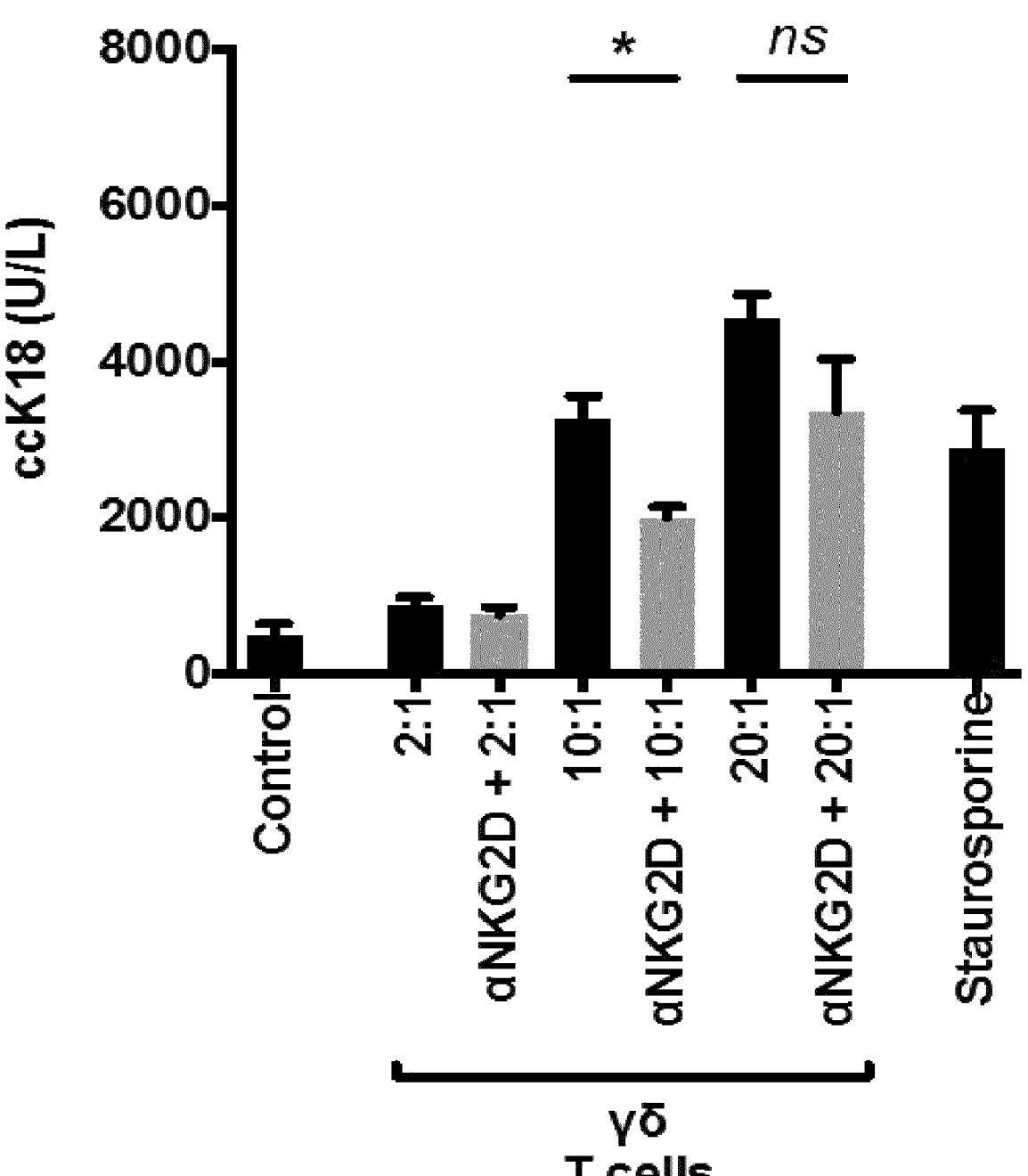
FIGS. 9A to 9C show that expanded and negatively sorted skin-derived γδ T cells display strong cytotoxicity against various human tumour cell lines with which they are co-cultured (FIG. 9A: HCT1954, FIG. 9B: HCT116, FIG. 9C: MD231) as measured by release of caspase-cleaved cytokeratin 18 by target cells, using ELISA.
Figure 9B:
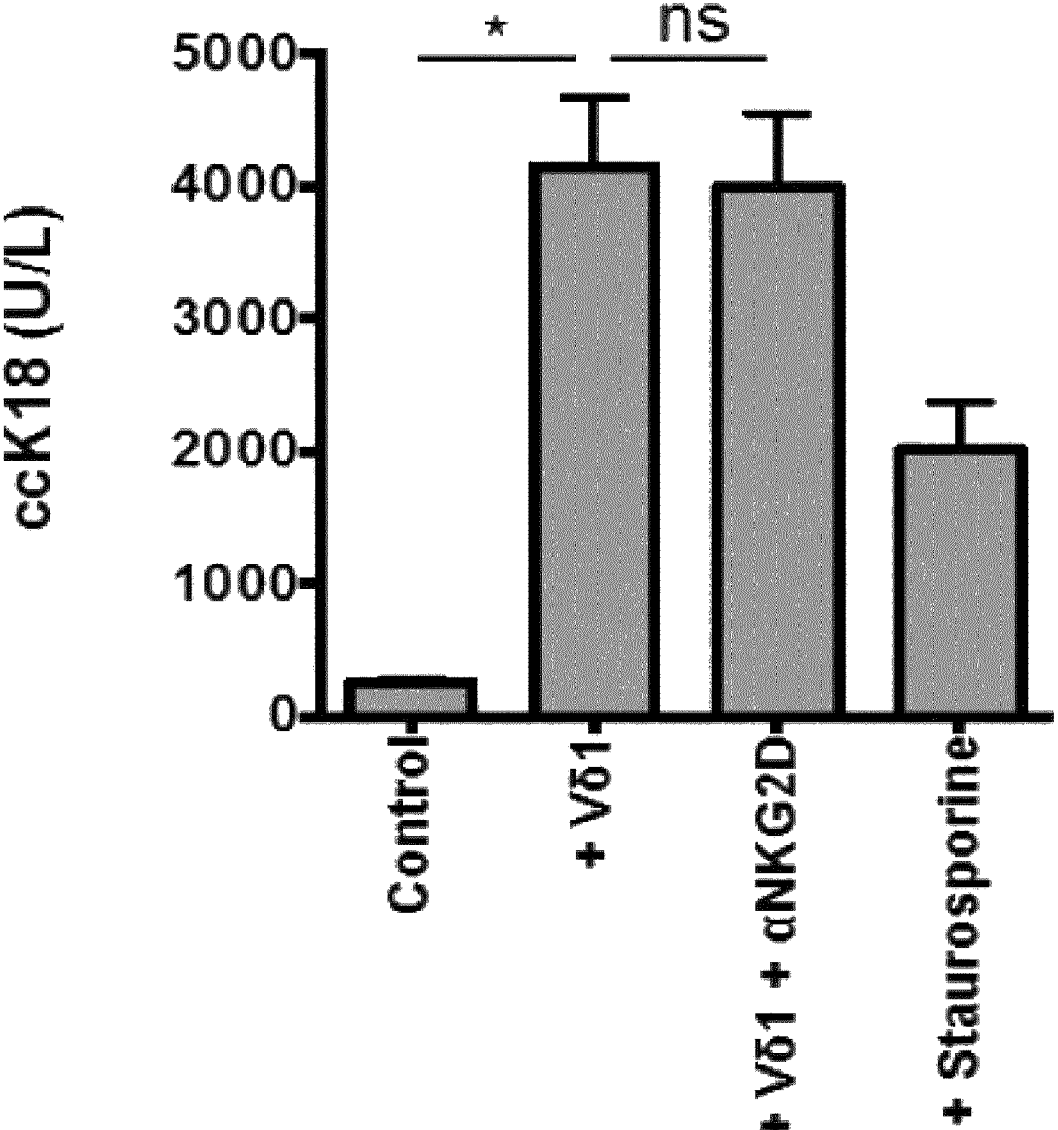
Figure 9C:
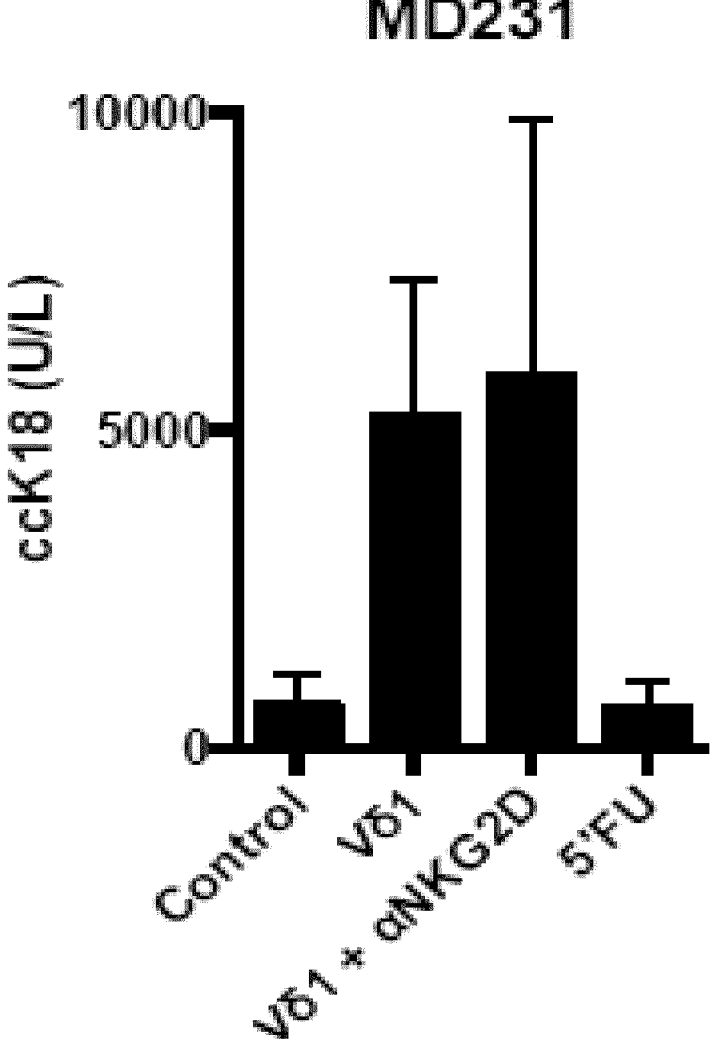

Furthermore, the cells produced large amounts of spontaneous IL-13, associated with atopic responses, during expansion and in contrast to freshly isolated skin-derived, TCR-activated γδ T cells; other cytokines were produced at much lower levels or not at all e.g. IL-17 A (FIG. 8). The high effector potentials of the cells could be increased further following stimulation with recombinant MICA (NKG2D ligand), with anti CD3 cross-linking, or with PMA/Ionomycin. To assess the cytotoxic potential of expanded γδ T cells against malignant target cells, we used established transformed cell lines in 24 hour co-culture experiments. Vδ1+ and DN γδ T cells showed very high cytotoxic activity towards Hela cells (cervix) and Caco2 (colon), in a dose-dependent fashion, far superior to conventional tissue αβ T cells (FIG. 5B). Furthermore, γδ-cell mediated cytotoxicity could be strongly inhibited by blocking the NKG2D receptor using soluble monoclonal antibodies indicating that this receptor is at least partly involved in tumour surveillance by derepressed human skin-derived γδ T cells. We furthermore confirmed the cytotoxic potential of these cells using other targets: HCT1954, MDAMB231 (both breast carcinoma) and HCT116 (colon) (FIG. 9).

Tissue-Resident γδ T Cells in Human Gut

Figure 11:
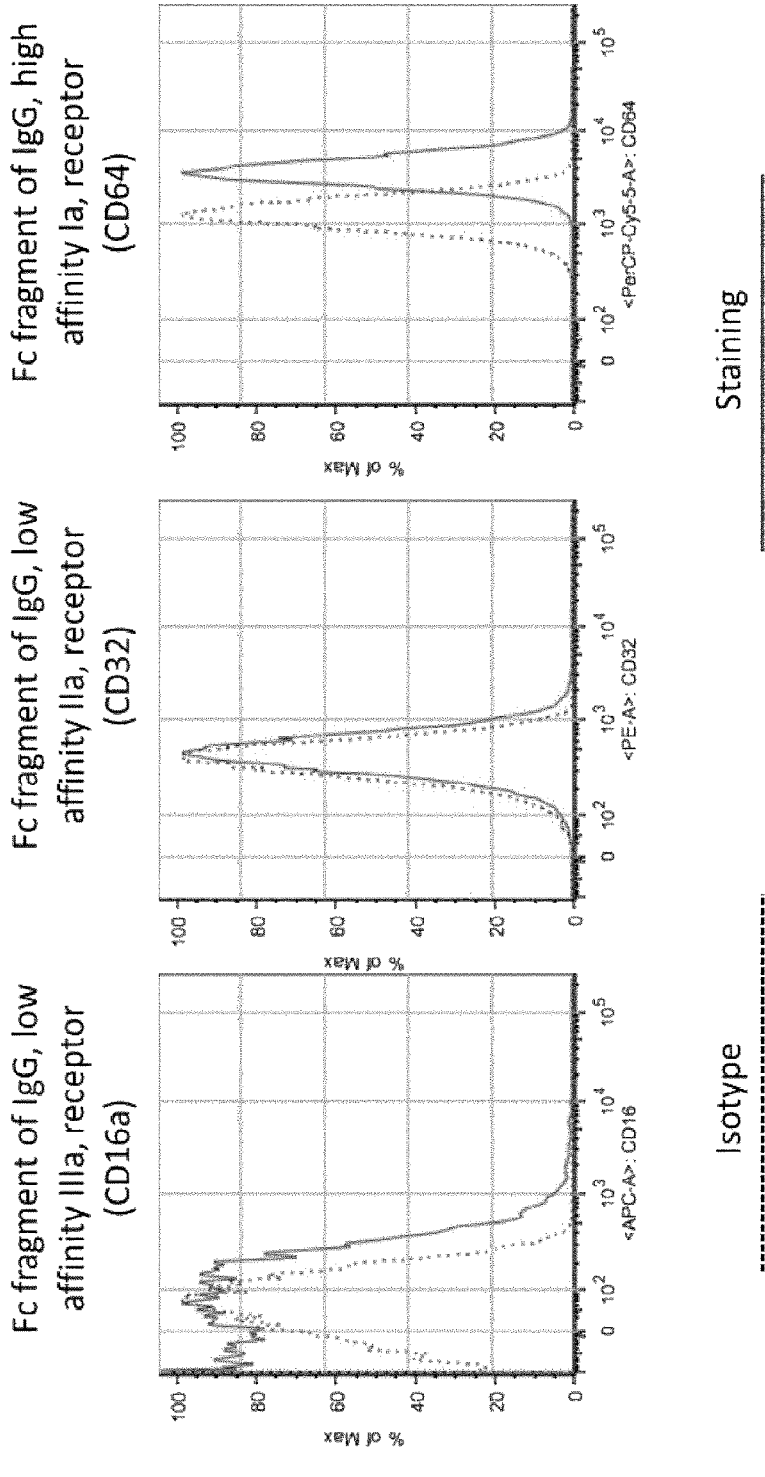
FIG. 11 shows that skin-derived Vδ1 T cells express minor levels of CD16 but show substantial expression of the high affinity IgG receptor CD64. Therefore in addition to direct cytotoxic activity, tissue-derived Vδ1 T cells could also be used to increase efficacy of monoclonal antibody therapies such as CD20 or Her2 therapies as they would be guided by the antibody to sides of malignancies and metastasis, recognise opsonized tumour cells and kill them via antibody-dependent cell-mediated cytotoxicity (ADCC). The results shown are from one representative donor (of four).
Figure 12:
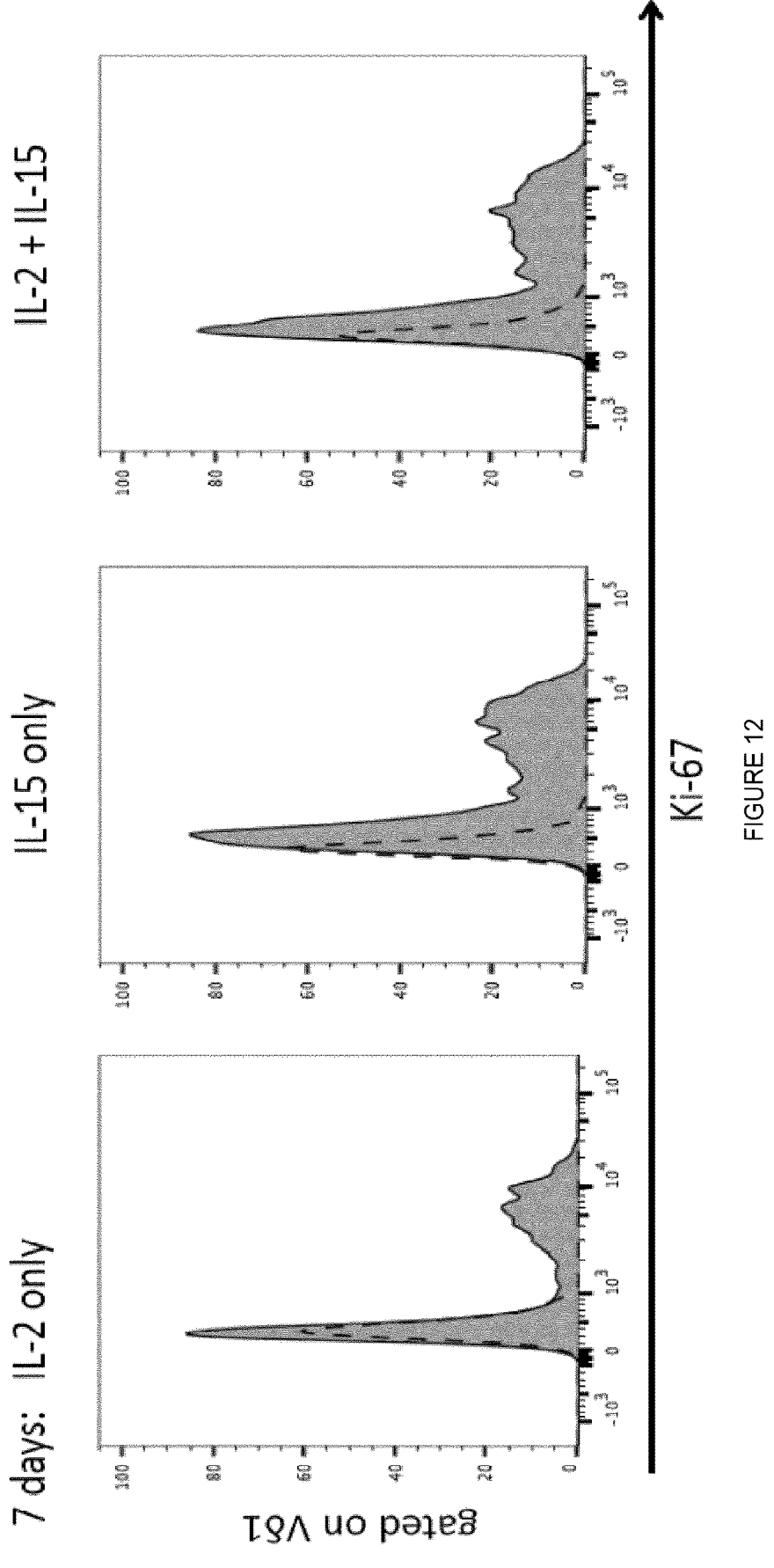
FIG. 12 shows the expansion of Vδ1 T cells in IL-2 (left panel), IL-15 (centre panel) and IL-2+IL-5 (right panel). Freshly isolated skin derived lymphocytes were cultured in 96 well flat bottom plates in RPMI Medium containing 10% FCS and 1% Pen/Strep and were supplemented with either IL-2, IL-15 or IL-2+IL-15 respectively for 7 days. Both IL-2 and IL-15 as well as the combination of both cytokines induced proliferation of Vδ1 T cells as indicated by the shift in KI-67 staining compared to isotype (true negative) staining in the absence of any stromal cells. Ki-67 only stains cells that have left GO of the cell cycle and is commonly associated with proliferation.
Figure 13:
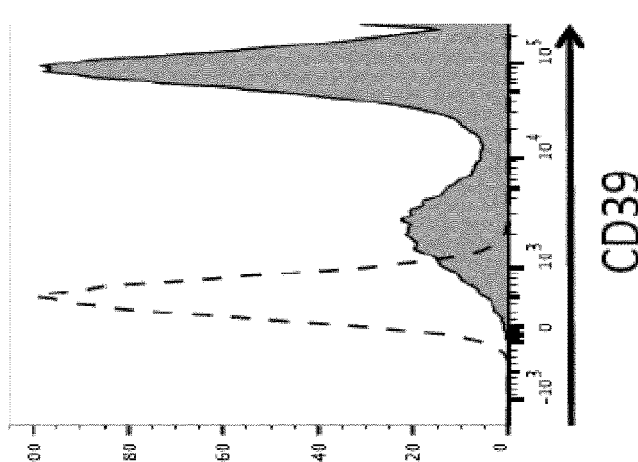
FIG. 13 shows flow cytometry results which indicate the expression of CD9, CCR3 and CD39 on the surface of expanded Vδ1 γδ T cells on day 21. The expanded skin derived Vδ1 T cells maintained high levels of the cell surface markers, CCR3, CD39 and CD9 as indicated by (dark histogram) versus the equivalent isotype staining (true negative, open histogram).
Figure 13:
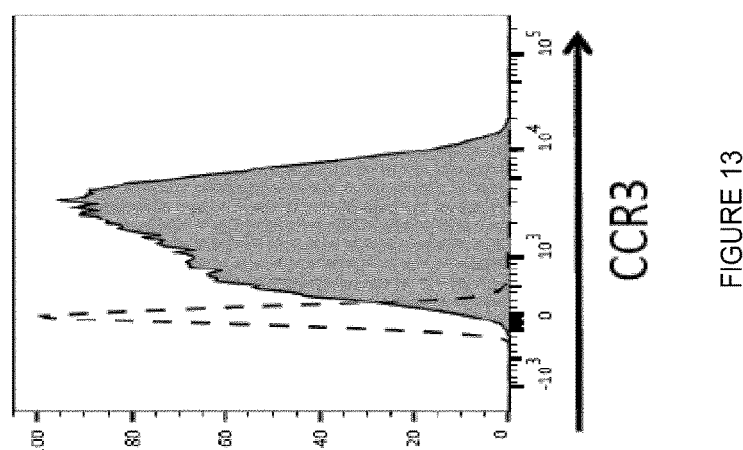
Figure 13:
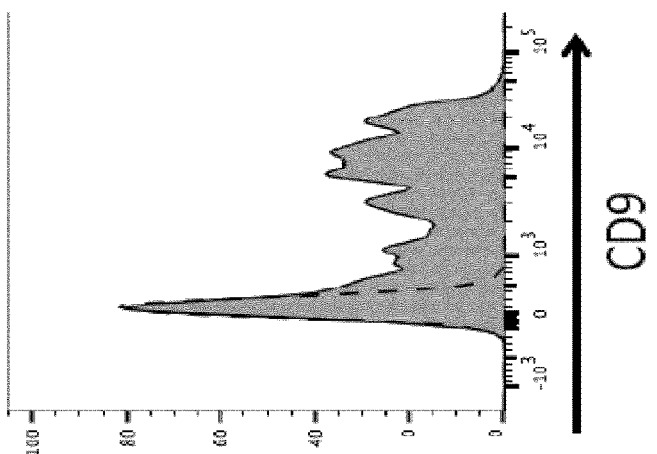
Figure 14:
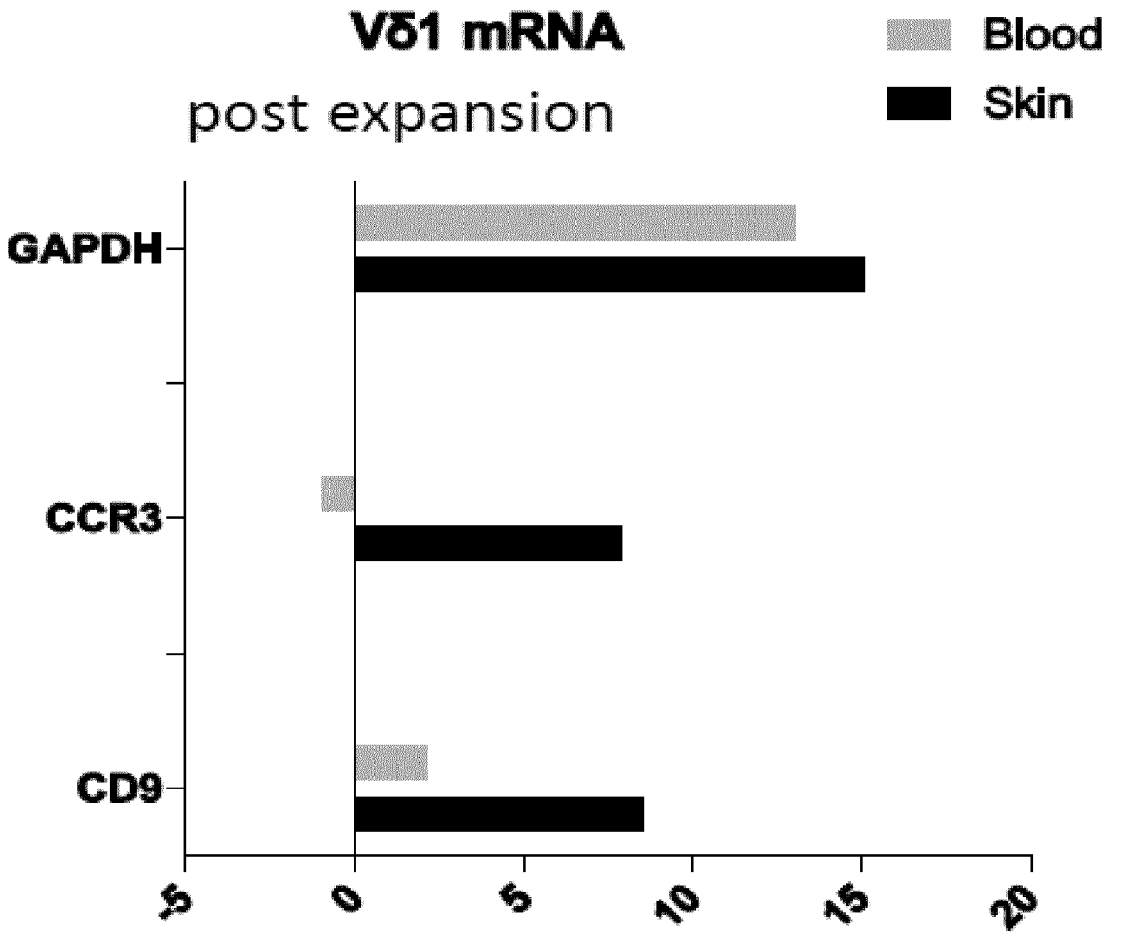
FIG. 14 shows the mRNA expression of CCR3 and CD9 in skin derived Vδ1 T cells (dark bars) and blood derived Vδ1 T cells (light bars). Skin derived Vδ1 T cells were expanded as disclosed herein, and blood derived Vδ1 T cells were expanded using plate bound antibodies for the V6 T cell receptor (20 μg/ml). After expansion, Vδ1 T cells were isolated using Fluorescence Activated Cell Sorting (FACS) and RNA was isolated from 3 donors for both groups (blood=grey vs. skin=black). Whole mRNA was sequenced and expression levels of indicated mRNAs normalised and log 2 transformed. All expression levels are shown in direct comparison, and in ratio to GAPDH, a common housekeeping gene expressed at high levels in most human cells.
Figure 15:
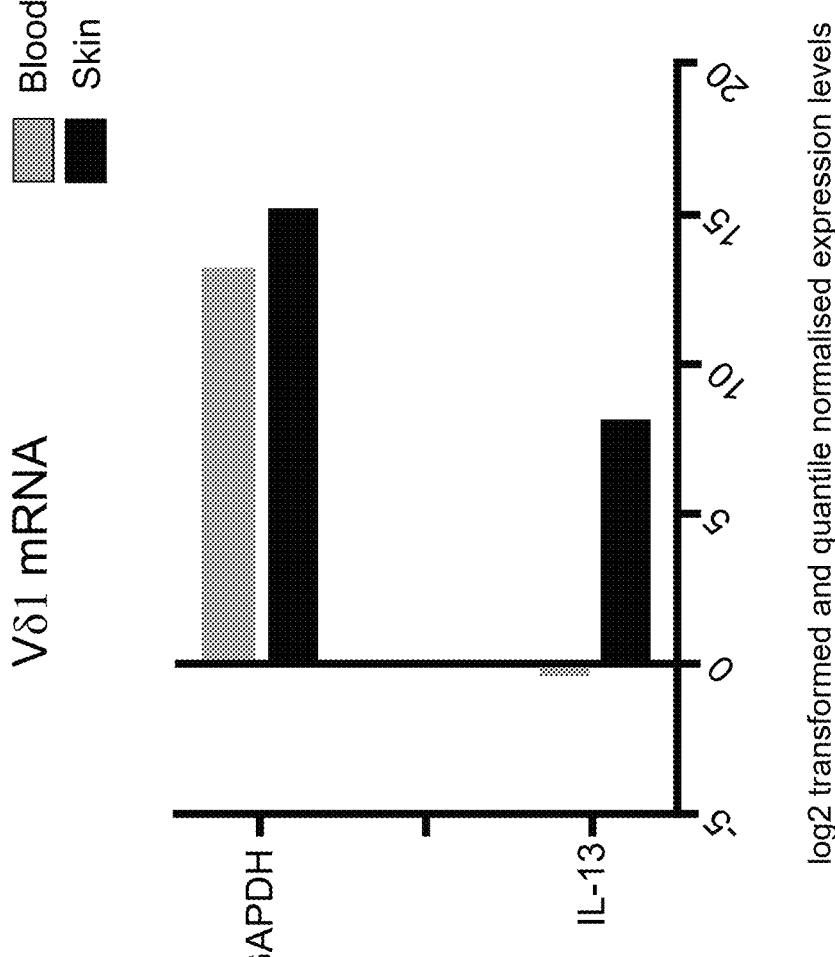
FIG. 15 shows the mRNA expression of IL-13 in skin derived Vδ1 T cells (dark bars) and blood derived Vδ1 T cells (light bars). Skin derived Vδ1 T cells were expanded as disclosed herein, and blood derived Vδ1 T cells were expanded using plate bound high dose antibodies for the V6 T cell receptor (20 μg/ml). After expansion, Vδ1 T cells were isolated using FACS and RNA was isolated from 3 donors for both groups (blood=grey vs. skin=black). Whole mRNA was sequenced and expression levels of mRNAs for IL-13 were normalised and log 2 transformed. Expression levels are shown in direct comparison, and in ratio to GAPDH.
Figure 16A:
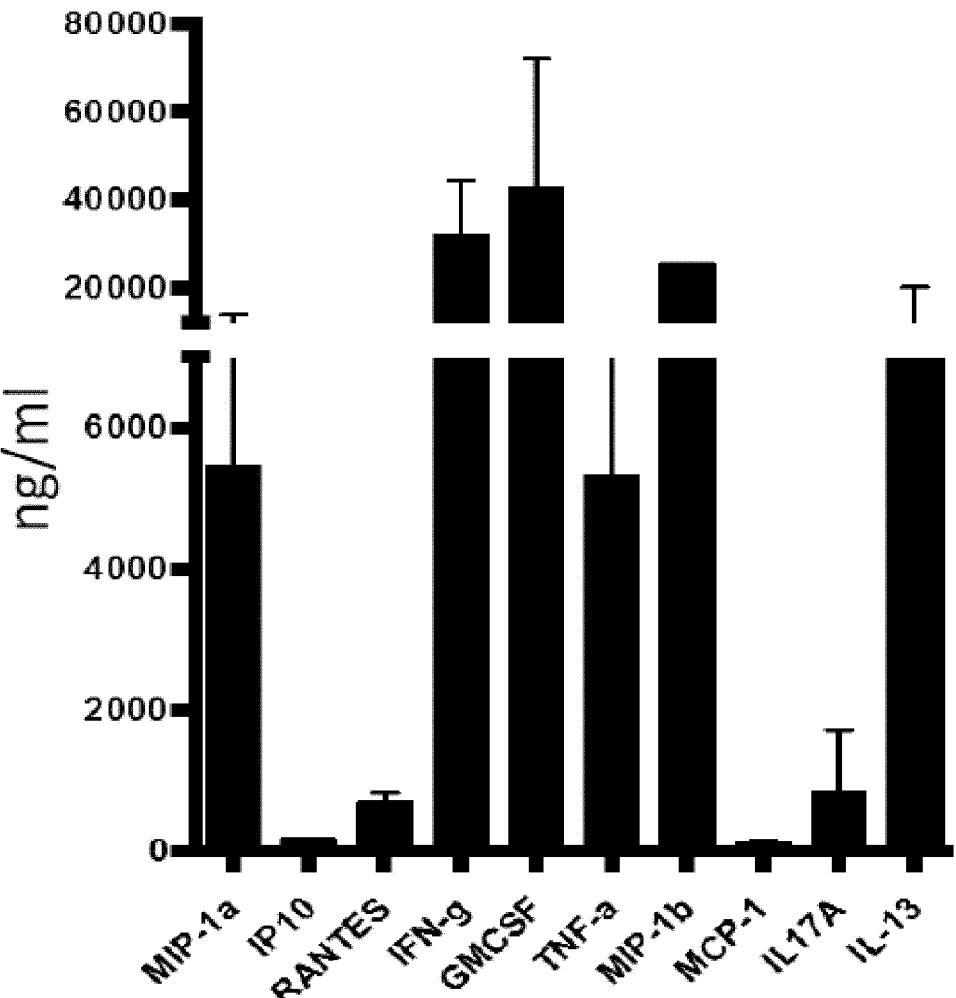
FIGS. 16A and 16B show the production of cytokines in skin derived Vδ1 T cells after TCR stimulation with PMA/Ionomycin (FIG. 16A) or anti-CD3 (FIG. 16B). Following isolation and expansion, skin derived Vδ1 T cells were purified using Fluorescence Activated Cell Sorting (FACS). 150.000 Vδ1 T cells were seeded into a 96 well flat bottom plate in duplicates for three donors and either stimulated with plate bound anti CD3 (5 μg/ml) or PMA/Ionomycin for 24 hours. Supernatants were analysed for absolute amounts of indicated cytokines using the LUMINEX® platform.
Figure 16B:
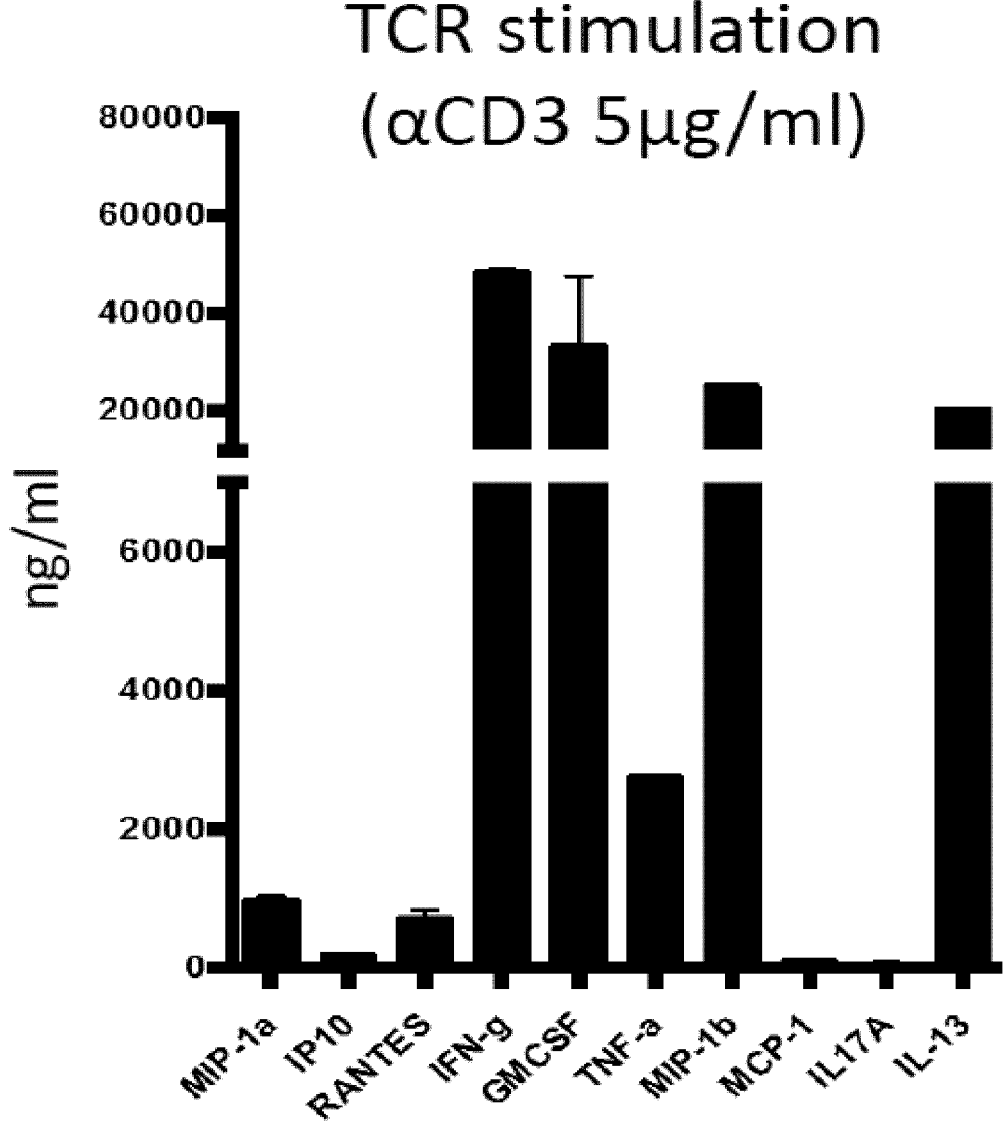

We have also identified a non-haematopoietic tissue-resident population of γδ T cells expressing a Vδ1 T cell receptor in grid cultures derived from human colon (FIG. 6). In 3 donors, we were able to expand these cells using the same methods as were employed 15 for skin cells, over a time course of 4 to 5 weeks. During expansion, colon-derived Vδ1+ and DN γδ T cells showed a similar pattern of Ki-67 up-regulation after their isolation from fibroblast-rich organotypic cell culture. Likewise colon-resident Vδ1+ and DN γδ T cells were strongly stimulated by the provision of ligands for the NKG2D receptor. It has been reported before that blood-derived γδ T cells are well equipped to execute antibody dependent cell-mediated cytotoxicity via CD16 expression proving enhanced cytotoxicity targeted against a CD20-positive B lineage lymphoma when combined with rituximab. Similarly, chronic lymphocytic leukemia (CLL) and HER2-positive breast cancer cells were killed more effectively when targeted with monoclonal antibodies (31). In order to evaluate the potential of skin derived Vδ1 T cells to target antibody opsonized target cells we checked expression levels of the three IgG1 associated Fc receptors CD16, CD32 and CD64. Skin derived Vδ1 T cells express minor levels of the FC receptor CD16 but show good expression levels for the high affinity IgG receptor CD64 (FIG. 11). Therefore tissue derived Vδ1 T cells may be well equipped to be use as an adjuvant to monoclonal antibody therapies such as CD20 or Her2 therapies as they will be guided by the antibody to sides of malignancies and metastasis, recognize opsonized tumour cells and kill targets via ADCC.

REFERENCES

1. Sensi M et al. *Cancer Research.* 2005; 65(2):632-40.
2. Gaudin C et al. *Journal of Immunology.* 1999; 162(3):1730-8.
3. Echchakir H et al. *Cancer Research.* 2001; 61(10):4078-83.
4. Karanikas V et al. *Cancer Research.* 2001; 61(9):3718-24.
5. Pieper R et al. *Journal of Experimental Medicine* 1999; 189(5):757-66.
6. Wang R F et al. *Science.* 1999; 284(5418):1351-4.
7. Topalian S L et al. *The New England Journal of Medicine.* 2012; 366(26):2443-54.
8. Brahmer J R et al. *The New England Journal of Medicine.* 2012; 366(26):2455-65.
9. Hodi F S et al. *The New England Journal of Medicine.* 2010; 363(8):711-23.
10. Robert C et al. *The New England Journal of Medicine.* 2011; 364(26):2517-26.
11. Pardoll D M. *Nature Reviews Cancer.* 2012; 12(4):252-64.
12. Fecher L A et al. *The Oncologist.* 2013; 18(6):733-43.
13. Ribas A. *The New England Journal of Medicine.* 2012; 366(26):2517-9.
14. Vantourout P, Hayday A. *Nature Reviews Immunology.* 2013; 13(2):88-100.
15. Hintz M et al. *FEBS Letters.* 2001; 509(2):317-22.
16. Freed-Pastor W A et al. *Cell.* 2012; 148(1-2):244-58.
17. Vantourout P et al. *Science Translational Medicine.* 2014; 6(231):231 ra49.
18. Wrobel P et al. *Scandinavian Journal of Immunology.* 2007; 66(2-3):320-8.
19. Todaro M et al. *Journal of Immunology.* 2009; 182(11):7287-96.
20. Gertner-Dardenne J et al. *Journal of Immunology.* 2012; 188(9):4701-8.
21. Mao C et al. *Journal of Immunol Research.* 2014; 2014:593562.
22. Godder K T et al. *Bone Marrow Transplantation.* 2007; 39(12):751-7.
23. Fournie J J et al. *Cellular & Molecular Immunology.* 2013; 10(1):35-41.
24. Curran K J et al. *Journal of Clinical Oncology.* 2015; 33(15):1703-6.
25. Hillerdal V et al. *BioDrugs.* 2015; 29(2):75-89.
26. Couzi L et al. *Journal of the American Society of Nephrology.* 2010; 21(1):181-8.
27. Zheng J et al. *Cellular & Molecular Immunology.* 2013; 10(1):50-57.
28. Deniger D C et al. *Molecular Therapy.* 2013; 21(3):638-47.
29. Clark R A et al. 2006. *Journal of Investigational Dermatology.* 126(5):1059-70.
30. Carrasco A. et al 2013. *Journal of Immunological Methods.* 389(1-2):29-37.
31. Tokuyama H. et al. *International Journal of Cancer.* 2008; 122(11):2526-34.
32. Willcox C R et al. *Nature Immunology.* 2012; 13(9):872-9.
33. Gillis and Smith. *Nature.* 1977; 268(5616):154-6.
34. Fujita et al. *Proceedings of the National Academy of Sciences USA.* 1984; 80(24):7437-41.
35. Grabstein et al. *Science.* 1994; 264(5161):965-8.
36. Helgason C et al. *Methods in Molecular Biology.* Humana Press Inc. U.S. (15 Oct. 2004) ISBN: 1588295451.
37. Picot J. *Methods in Molecular Medicine.* Humana Press Inc., U.S. (9 Dec. 2004) ISBN: 1588292223.
38. Freshney R. *Culture of Animal Cells: A Manual of Basic Technique.* John Wiley & Sons Inc., (2 Aug. 2005) ISBN: 0471453293,
39. Ho W Y et al. *Journal of Immunological Methods.* 2006; 310:40-52.
40. Fauci A S et al, eds. *Harrison's Principles of Internal Medicine.* 2001; 15th Ed., McGraw-Hill, New York.
41. Petrini I. et al. *European Journal of Clinical Investigation.* 2009; 39(9):813-8.
42. Gruenbacher et al. *Blood.* 2009; 114(20):4422-31.
43. Almeida et al Clin Cancer Res (2016) 10.1158/1078-0432.CCR-16-0597
44. Deniger D. et al. *Frontiers in Immunology.* 2014:5(636):1-10.

The invention claimed is:

1. A method for expanding non-haematopoietic tissue-resident γδ T cells in vitro, the method comprising culturing lymphocytes obtained from non-haematopoietic tissue of humans or non-human animals in the presence of interleukin-15 (TL-15) and interleukin-2 (IL-2), wherein the lymphocytes are not in direct contact with stromal or epithelial cells during culture, and wherein the lymphocytes are cultured in a γδ T cell expansion medium devoid of growth factors other than IL-2 and IL-15.

2. The method of claim 1, wherein the lymphocytes are not in direct contact with fibroblasts during culture.

3. The method of claim 1, wherein the method comprises culturing the lymphocytes in the absence of TCR activation or co-stimulation signals.

4. The method of claim 1, wherein the method comprises culturing the lymphocytes in the absence of a T cell receptor pathway agonist.

5. The method of claim 1, wherein the lymphocytes are cultured in the absence of stromal or epithelial cells.

6. The method of claim 5, wherein the stromal or epithelial cells are removed prior to culture.

7. The method of claim 5, wherein the lymphocytes are cultured in the absence of fibroblasts.

8. The method of claim 7, wherein the fibroblasts are removed prior to culture.

9. The method of claim 1, wherein the γδ expansion medium does not activate or co-stimulate T cell receptors.

10. The method of claim 1, wherein the lymphocytes have been obtained from skin, the gastrointestinal tract, mammary gland tissue, lung, liver, pancreas, or prostate.

11. The method of claim 1, wherein the γδ T cells are non-Vδ2 cells.

12. The method of claim 4, wherein the method comprises culturing the lymphocytes in the absence of an exogenously added T cell receptor pathway agonist.

13. The method of claim 10, wherein the lymphocytes have been obtained from colon.

14. The method of claim 11, wherein the non-Vδ2 cells are Vδ1 cells or double negative (DN) γδ T cells.

* * * * *